US011707397B2

United States Patent
Mangiardi

(10) Patent No.: US 11,707,397 B2
(45) Date of Patent: Jul. 25, 2023

(54) INTEGRATED OPERATING ROOM LIGHTING AND PATIENT WARMING SYSTEM—DESIGN AND COMPONENTS

(71) Applicant: Optimus Integrated Surgical Environment AG, Zurich (CH)

(72) Inventor: John R. Mangiardi, Zug (CH)

(73) Assignee: Optimus Integrated Surgical Environment AG, Zurich (CH)

( * ) Notice: Subject to any disclaimer, the term of this patent is extended or adjusted under 35 U.S.C. 154(b) by 842 days.

(21) Appl. No.: 16/676,411

(22) Filed: Nov. 6, 2019

(65) Prior Publication Data

US 2020/0085663 A1 Mar. 19, 2020

Related U.S. Application Data

(63) Continuation of application No. 16/348,457, filed as application No. PCT/EP2017/078636 on Nov. 8, 2017, now Pat. No. 11,389,361.

(Continued)

(51) Int. Cl.
*A61G 13/10* (2006.01)
*A61G 13/12* (2006.01)
(Continued)

(52) U.S. Cl.
CPC ............ *A61G 13/108* (2013.01); *A47B 96/00* (2013.01); *A47L 11/00* (2013.01); *A47L 11/282* (2013.01);
(Continued)

(58) Field of Classification Search
CPC .... A61G 13/08; A61G 13/12; A61G 2210/70; A61G 2210/90; A61G 12/002;
(Continued)

(56) References Cited

U.S. PATENT DOCUMENTS 5,966,763 A * 10/1999 Thomas ............... A47C 27/086
5/911
6,049,927 A * 4/2000 Thomas ................ A61G 13/12
607/104

(Continued)

FOREIGN PATENT DOCUMENTS

CN 201409714 Y 2/2010
CN 201676062 U 12/2010
(Continued)

OTHER PUBLICATIONS

International Provisional Opinion Accompanying the Partial Search Report, PCT/EP2017/078650 (Integrated Operating Room Sterilization System—Design and Components, filed Nov. 8, 2017), ISA/EPO, 5 pages, dated Feb. 21, 2018.
International Search Report, PCT/EP2017/078636 (Integrated Operating Room Lighting and Patient Warming System—Design and Components, filed Nov. 8, 2017), ISA/EPO, 7 pages, dated Apr. 10, 2018.

(Continued)

*Primary Examiner* — Robert G Santos
(74) *Attorney, Agent, or Firm* — Choate, Hall & Steart LLP; William R. Haulbrook; Michael D. Schmitt

(57) ABSTRACT

A patient warming system for stabilizing and/or heating and cooling a patient includes a plurality of solid-surface sections arranged for attachment to a surgical table and a warming pad layer comprising a plurality of warming pads configured for removable connection to the plurality of solid-surface sections. At least one of the plurality of solid-surface sections includes a power connector for connection to an external power source. Each warming pad of the plurality of warming pads includes a foam insulation layer, a distributed heating element layer having a warming-pad power connection for connection to the power connector, an isothermal layer, and a flexible waterproof layer. Power supplied to the warming-pad power connection of the distributed heating element layer of the respective warming pad can be used to provide a user-selected uniform temperature (Continued)

over the surface of the flexible waterproof layer in order to prevent hot spots.

8 Claims, 56 Drawing Sheets

Related U.S. Application Data

(60) Provisional application No. 62/427,773, filed on Nov. 29, 2016, provisional application No. 62/419,391, filed on Nov. 8, 2016.

(51) Int. Cl.

| *A61G 12/00* | (2006.01) |
|---|---|
| *A61F 7/08* | (2006.01) |
| *A47B 96/00* | (2006.01) |
| *A47L 11/00* | (2006.01) |
| *A61L 2/20* | (2006.01) |
| *B01L 1/02* | (2006.01) |
| *F21S 2/00* | (2016.01) |
| *F21S 8/04* | (2006.01) |
| *F21S 10/02* | (2006.01) |
| *F21V 33/00* | (2006.01) |
| *A47L 11/282* | (2006.01) |
| *A47L 11/40* | (2006.01) |
| *A61L 2/04* | (2006.01) |
| *A61L 2/10* | (2006.01) |
| *A61L 2/24* | (2006.01) |
| *B08B 3/10* | (2006.01) |
| *B08B 7/00* | (2006.01) |
| *B08B 7/04* | (2006.01) |
| *A61B 50/10* | (2016.01) |
| *A61B 90/30* | (2016.01) |
| *A61L 2/08* | (2006.01) |
| *A61B 17/00* | (2006.01) |
| *H05B 3/34* | (2006.01) |
| *H05B 3/56* | (2006.01) |
| *H05B 3/58* | (2006.01) |
| *H05B 3/52* | (2006.01) |
| *H04L 67/12* | (2022.01) |
| *G21F 7/005* | (2006.01) |
| *A61F 7/00* | (2006.01) |
| *F21W 131/205* | (2006.01) |

(52) U.S. Cl.
CPC ....... *A47L 11/4005* (2013.01); *A47L 11/4061* (2013.01); *A47L 11/4083* (2013.01); *A47L 11/4091* (2013.01); *A61B 17/00* (2013.01); *A61B 50/10* (2016.02); *A61B 90/30* (2016.02); *A61F 7/08* (2013.01); *A61G 12/002* (2013.01); *A61G 13/12* (2013.01); *A61L 2/04* (2013.01); *A61L 2/088* (2013.01); *A61L 2/10* (2013.01); *A61L 2/202* (2013.01); *A61L 2/24* (2013.01); *B01L 1/02* (2013.01); *B08B 3/10* (2013.01); *B08B 7/0057* (2013.01); *B08B 7/04* (2013.01); *F21S 2/005* (2013.01); *F21S 8/046* (2013.01); *F21S 10/02* (2013.01); *F21S 10/023* (2013.01); *F21V 33/0088* (2013.01); *H04L 67/12* (2013.01); *H05B 3/342* (2013.01); *H05B 3/52* (2013.01); *H05B 3/56* (2013.01); *H05B 3/58* (2013.01); *A47L 2201/00* (2013.01); *A47L 2201/022* (2013.01); *A47L 2201/024* (2013.01); *A47L 2201/026* (2013.01); *A47L 2201/028* (2013.01); *A47L 2201/04* (2013.01); *A61B 2050/105* (2016.02); *A61F 2007/0096* (2013.01); *A61G 2210/70* (2013.01); *A61G 2210/90* (2013.01); *A61L 2202/11* (2013.01); *A61L 2202/122* (2013.01); *A61L 2202/14* (2013.01); *A61L 2202/16* (2013.01); *A61L 2202/17* (2013.01); *A61L 2202/182* (2013.01); *A61L 2202/24* (2013.01); *A61L 2202/25* (2013.01); *B08B 2203/007* (2013.01); *F21W 2131/205* (2013.01); *G21F 7/005* (2013.01)

(58) Field of Classification Search
CPC ......... A61B 50/10; A61B 90/30; A61B 17/00; A61F 7/08; A61F 2007/0096; A47B 96/00; A47L 11/00; A47L 11/282; A47L 11/4005; A47L 11/4061; A47L 11/4083; A47L 11/4091; A47L 2201/04; H05B 3/52; H05B 3/56; H05B 3/58; H05B 3/342; A61L 2/04; A61L 2/088; A61L 2/10; A61L 2/202; A61L 2/24; B01L 1/02; B08B 3/10; B08B 7/0057; B08B 7/04; F21S 2/005; F21S 8/046; F21S 10/02; F21S 10/023; F21V 33/0088; H04L 67/12

USPC ............... 5/421, 284; 219/528, 212, 217
See application file for complete search history.

(56) References Cited

U.S. PATENT DOCUMENTS

| 6,182,316 | B1* | 2/2001 | Thomas | A61G 7/05753 |
|---|---|---|---|---|
| | | | | 607/104 |
| 6,202,360 | B1 | 3/2001 | Rattner et al. | |
| 6,401,283 | B2* | 6/2002 | Thomas | A61G 13/12 |
| | | | | 5/503.1 |
| 6,484,334 | B1 | 11/2002 | Borders et al. | |
| 6,582,456 | B1 | 6/2003 | Hand et al. | |
| 6,912,749 | B2* | 7/2005 | Thomas | A47C 27/086 |
| | | | | 5/691 |
| 8,112,942 | B2 | 2/2012 | Bohm et al. | |
| 8,876,812 | B2* | 11/2014 | Aramayo | A61B 18/16 |
| | | | | 606/41 |
| 8,905,585 | B2 | 12/2014 | Dallam et al. | |
| 9,222,257 | B2 | 12/2015 | Dallam et al. | |
| 11,389,361 | B2* | 7/2022 | Mangiardi | A61B 90/30 |
| 11,439,558 | B2* | 9/2022 | Mangiardi | A47B 96/00 |
| 2001/0000829 | A1* | 5/2001 | Thomas | A61G 7/05753 |
| | | | | 5/740 |
| 2002/0019654 | A1 | 2/2002 | Ellis et al. | |
| 2002/0112287 | A1* | 8/2002 | Thomas | A61G 13/12 |
| | | | | 5/503.1 |
| 2004/0149711 | A1 | 8/2004 | Wyatt et al. | |
| 2007/0209143 | A1 | 9/2007 | Choi et al. | |
| 2008/0056933 | A1 | 3/2008 | Moore et al. | |
| 2008/0287924 | A1 | 11/2008 | Mangiardi | |
| 2010/0217260 | A1* | 8/2010 | Aramayo | A61B 18/16 |
| | | | | 606/41 |
| 2011/0277399 | A1 | 11/2011 | Boekeloo | |
| 2012/0022620 | A1* | 1/2012 | Khodak | A61G 11/00 |
| | | | | 5/601 |
| 2013/0104907 | A1 | 5/2013 | Giap | |
| 2014/0074086 | A1 | 3/2014 | MacIntyre-Ellis et al. | |
| 2015/0290065 | A1 | 10/2015 | Augustine et al. | |
| 2016/0081846 | A1 | 3/2016 | Katzenstein | |
| 2019/0328598 | A1* | 10/2019 | Mangiardi | H05B 3/52 |
| 2020/0069500 | A1* | 3/2020 | Mangiardi | F21S 2/005 |
| 2020/0069827 | A1* | 3/2020 | Mangiardi | A61G 12/002 |
| 2020/0070214 | A1* | 3/2020 | Mangiardi | B08B 3/10 |
| 2020/0078125 | A1* | 3/2020 | Mangiardi | A61L 2/24 |
| 2020/0085662 | A1* | 3/2020 | Mangiardi | A61L 2/202 |
| 2020/0085663 | A1* | 3/2020 | Mangiardi | A61L 2/088 |

FOREIGN PATENT DOCUMENTS

| CN | 103157188 | A | 6/2013 |
|---|---|---|---|
| CN | 205268482 | U | 6/2016 |

(56) References Cited

FOREIGN PATENT DOCUMENTS

| | | | | |
|---|---|---|---|---|
| CN | 205515264 U | 8/2016 | | |
| CN | 105960194 A | 9/2016 | | |
| EP | 0821928 A2 | 2/1998 | | |
| EP | 3070627 A1 | 9/2016 | | |
| EP | 3649994 A1 * | 5/2020 | ............ | A47B 96/00 |
| KR | 2006/0027207 A | 3/2006 | | |
| WO | WO-2004/082899 A2 | 9/2004 | | |
| WO | WO-2005/006098 A2 | 1/2005 | | |
| WO | WO-2010/107724 A1 | 9/2010 | | |
| WO | WO-2016/097892 A1 | 6/2016 | | |
| WO | WO-2018/087162 A1 | 5/2018 | | |
| WO | WO-2018/087171 A1 | 5/2018 | | |
| WO | WO-2018087171 A9 * | 7/2019 | ............ | A47B 96/00 |

OTHER PUBLICATIONS

International Search Report, PCT/EP2017/078650 (Integrated Operating Room Sterilization System—Design and Components, filed Nov. 8, 2017), ISA/EPO, 6 pages, dated Apr. 23, 2018.
Partial International Search Report, PCT/EP2017/078650 (Integrated Operating Room Sterilization System—Design and Components, filed Nov. 8, 2017), ISA/EPO, 2 pages, dated Feb. 21, 2018.
Written Opinion, PCT/EP2017/078636 (Integrated Operating Room Lighting and Patient Warming System—Design and Components, filed Nov. 8, 2017), ISA/EPO, 11 pages, dated Apr. 10, 2018.
Written Opinion, PCT/EP2017/078650 (Integrated Operating Room Sterilization System—Design and Components, filed Nov. 8, 2017), ISA/EPO, 10 pages, dated Apr. 23, 2018.

* cited by examiner

320

321
Close external openings to room

322
Increase pressure of room by a predetermined amount

323
Measure the pressure of the room using a sensor in proximity to the room

324
Determine if pressure of room has exceeded a pressure change threshold

325
If not, allow sterilization procedure to proceed

488
Open of a first door of the pass-through logistics cabinet

489
Prevent at least one door from being opened using an interlock system

641
Recognize that a medical apparatus has been connected to a computing device

642
Identify the medical apparatus

643
Manipulate the medical apparatus format data received from the medical apparatus to standardized data format

644
Transmit the standardized data format to a second computing device

645
Display a standardized visualization of the standardized data on a display of the second computing device

FIG. 6D

INTEGRATED OPERATING ROOM LIGHTING AND PATIENT WARMING SYSTEM—DESIGN AND COMPONENTS

RELATED APPLICATIONS

This application is a continuation of U.S. patent application Ser. No. 16/348,457, filed on May 8, 2019, which is National Stage Entry, under 35 U.S.C. § 371, of international (PCT) patent application no. PCT/EP2017/078636, filed on Nov. 8, 2017, which claims the benefit of priority to U.S. Provisional Patent Application Ser. No. 62/419,391, filed Nov. 8, 2016, and to U.S. Provisional Patent Application Ser. No. 62/427,773, filed Nov. 29, 2016, the contents of which are incorporated herein by reference in their entirety. PCT/EP2017/078636 is also related to its sister international (PCT) patent application, PCT/EP2017/078650, entitled, "Integrated Operating Room Sterilization System—Design And Components," filed on Nov. 8, 2017, which is hereby incorporated by reference in its entirety.

TECHNICAL FIELD

This invention relates generally to components and systems for reducing risks to patients in healthcare environments. More particularly, in some embodiments, the invention is an integrated system that may be used in an operating room to minimize hazards that could otherwise produce complications from a surgical procedure.

BACKGROUND

The increasing complexity of healthcare environments with time has led to a change in the organizational structure of healthcare systems. Historically, a hospital was a small and individually independent organization with a small number of departments, staff, and information systems. A single expert or a limited number of experts could exercise effective institutional control over the entire hospital or even a modest healthcare system. Hospitals could operate as a top-down organization much like the military with a single expert or small committee acting as the commander. However, as hospitals have grown to accommodate an increasingly large number of departments, each with their own increasing complexity, the preference has been to adopt an increasingly flat organizational structure where efficiency is gained or had by allowing many mostly independent units (e.g., individual departments, clinics, campuses) to operate within the hospital ecosystem. The shift in organizational structure over time has allowed medical experts to apply their increasingly specialized and deep knowledge to treat a growing range of complex medical problems without being distracted by organizational considerations.

The transition in organizational structure from a centralized to decentralized approach in order to gain efficiency has been accompanied by continued growth in the number and frequency of medical errors that occur in healthcare environments. Many new sources of potential medical errors have been introduced by the great increase in organizational complexity resulting from the adoption of flat organizational structures in healthcare environments. The growth in medical errors from the influx of new sources of potential errors resulting from increasing organizational complexity has exceeded expected reductions in medical errors due to vast improvements in the quality of training and specialization of medical experts. This contradiction between increasing medical errors and improvements in training of medical experts is due to a difference in the type of medical error. Medical errors due to complex organizational structures must be distinguished from those that occur due to a failure of an individual medical expert.

Risks that lead to medical errors can be divided into two categories based on their source of origin: "organizational infrastructure" (OI) risks and "protocols and policies" (P&P) risks. P&P risks result from human factors. OI risks result from the particular physical and institutional organizational infrastructure of a healthcare environment. P&P risks can be mitigated by revising or supplementing existing protocols and policies and/or improving compliance, whereas 01 risks require adoption of new infrastructure into the healthcare environment. Altering existing protocols and policies and/or increasing compliance generally requires minimal cost and allows easy adoption. Adoption of infrastructure to mitigate OI risks frequently requires more extensive capital investments, but offers the potential to eliminate risks that are prone to repetition due to inherent limitations in infrastructural design without depending on attaining high compliance by staff.

P&P risks in healthcare environments are generally understood and P&P risk reduction is the subject of continued efforts in healthcare environments. Errors resulting from P&P risks usually represent a failure by staff (e.g., medical experts) to follow well-established protocols that have been proven to improve patient outcomes. Improvements in training and performance of staff lead to reductions in the number of errors resulting from P&P risks. Additionally, repeated errors due to previously unrecognized P&P risks lead to changes in protocols or policies that reduce the number and frequency of future errors. For example, the adoption and adherence to stringent hand washing protocols has greatly reduced the transmission of infections in healthcare environments over the last century. Consequently, errors resulting from P&P risks currently represent a minority of medical errors (as low as 20% in some hospital settings with high compliance). However, modern protocols and policies are highly developed. Thus, incremental improvements in current protocols and policies have low marginal return in mitigating P&P risks even if perfect compliance by staff can be attained.

OI risks are less well understood and relatively little effort has been given to addressing such infrastructural risks in healthcare environments despite the potential to significantly reduce medical errors by eliminating OI risks. Modern medical procedures and patient monitoring require a large array of equipment interacting to provide care. The more equipment that is used in a particular setting of a healthcare environment, the greater the number of OI risks present. However, modern healthcare environments frequently are not assessed to identify OI risks, despite the ever growing complex of physical and institutional components being used. Assumptions are made by organizational leaders about the quality of individual components, produced by a wide variety of vendors, without consideration for the role of those components in an integrated setting and the associated OI risks. The poor design of such individual components in dealing with complex healthcare infrastructures can lead to instances where medical staff is blamed for errors that are more appropriately categorized as infrastructural errors, resulting in a higher number and magnitude of medical malpractice claims. By addressing OI risks in healthcare environments through deliberate engineering of components for use in highly integrated settings, the trend of increasing medical errors can be reversed to reduce costs and increase efficiency and patient outcomes.

While OI risks can vary in their exact nature, potential impact, and likelihood, the majority of such risks are able to be eliminated through deliberate engineering focused on use in complex, multifunctional healthcare environments. For example, if a wire running across the floor of an operating room is eliminated or relocated, risks associated with tripping over the wire as well as with the wire being disconnected during a surgical procedure are eliminated for all future procedures. As an additional example, displaying an X-ray in an operating room electronically would eliminate risk from surgery being performed at an incorrect site on a patient due to viewing the X-ray at an incorrect orientation in a traditional operating room. Many other OI risks associated with spreading of infections, surgical complications, and misinterpretation of patient data that exist in modern healthcare environments are similarly capable of being eliminated by engineering and design of multifunctional components for use in highly integrated settings. The lessons of "safety by design" learned in other industries such as aeronautics, automobile, and industrial manufacturing have yet to be applied to many components and systems of healthcare environments.

Currently, most components used in modern healthcare environments are each designed by a unique vendor. Consequently, these components are designed to optimize individual performance without consideration for the potential OI risks that result when such components are integrated into settings of the healthcare environments. While, no modern-day operating room can be considered "simple," complexity can be managed through design. There is a continued need for components and systems for use in healthcare environments that are engineered to reduce infrastructural risks.

SUMMARY OF INVENTION

Described herein are components, systems, and methods of use of an integrated lighting and air plenum, a patient warming ad system, an integration system of these components into an operating room with wireless control, and systems for controlling such components. An integrated operating room will allow mitigation or elimination of risks (e.g., infrastructural risks (e.g., OI risks)) that may otherwise be associated with a setting in a healthcare environment. The elimination of clutter, control of major components under a unified and intuitive user interface, and the logical elimination of potential accumulated risk events (e.g., OI risks) are deliberately addressed, in whole or in part, by the present disclosure. The present disclosure describes the following: integrated lighting and air plenums, patient warming pad systems and components, systems for integrating such components into an operating room and with wireless control, and systems for controlling such components.

It is an objective of certain embodiments of the present invention to reduce OI risks in certain settings (e.g., operating rooms, emergency rooms, exam rooms, patient rooms) of healthcare environments by engineering of components and systems to be integrated and multifunctional. Components and systems of healthcare environments can be engineered to mitigate or eliminate OI risks, for example, by reducing clutter or integrating many needed functionalities into a single component. Common components and/or functionalities that are present or desirable in modern healthcare environments are, for example, organized storage of medical supplies, air flow, sterilization and sterilizability, ambient and patient lighting, and biometric tracking.

Described herein are components, systems, and methods of their use that allow risks (e.g., infrastructural risks (e.g., OI risks)) that may otherwise be associated with a setting in a healthcare environment to be mitigated or eliminated. The elimination of clutter, control of major components under a unified and intuitive user interface, and the logical elimination of potential accumulated risk events (e.g., OI risks) are deliberately addressed, in whole or in part, by the present disclosure. In some embodiments, the deliberate elimination of physical and visual clutter by multiple apparatus, such as recessed lighting, displays, and service connections allows a clear line-of-sight across the room. Embodiments described herein create a psychologically more comfortable and efficient room to be in, enhancing the sense of simplicity for medical staff and patients.

In some embodiments of the present disclosure, various devices and equipment are removed from the working space of an operating room by recruiting in-wall, in-ceiling, and in-floor spaces to physically situate such devices out of the immediate operating room environment. In some embodiments, building a surrounding space (e.g., a wall-within-a-wall) would allow for devices as visual monitors, audiovisual recording and conference cameras, trash units, logistics cabinets, ambient lighting and ozone sterilization technologies to be physically located out of the room, while remaining available for direct use. This efficient construction concept allows not just recessed components and systems but also the use of multifunctional walls, such as backlit walls or walls with additional safety or security features, for example. In some embodiments, utilizing available above ceiling space to house devices such as robotic surgical lighting fixtures, laminar plenum airflow units, audio and visual recording and playback devices, as well as sensor systems would effectively eliminate these devices from the immediate working space. In some embodiments, utilizing the below and through floor space for such things as medical gas, vacuum, electrical wiring and communications and audiovisual connections such as Ethernet and photo-optic cabling, allows for the reduction in the number of exposed wires and hoses in the working space of the operating room. In some embodiments, this equipment can retract completely from the environment when not in demand or use. This is as opposed to the increasing number of ceiling "boom" systems that currently act as permanent spatial challenges in the modern operating room.

In most healthcare environments, air flow and lighting in a room are handled as two separate systems. Frequently, air outlets are mounted in the ceiling as are various lighting fixtures. In healthcare environments, the quality of air flow and lighting provided to a room can have profound effect on the ability of medical staff to properly perform their duties. For example, in an operating room, highly laminar airflow around the operating theater is highly desirable to maintain the sterility of the area immediately surrounding a patient. Further, adequate lighting on the patient is required during the course of a surgery to ensure medical errors are not made. Many surgical lighting and laminar airflow systems exist to provide lighting and air flow for operations that is highly adjustable to the needs of a patient (e.g., to the location or orientation of the patient). However, both of these conventional systems suffer from certain flaws of engineering that result in a suboptimal experience for medical staff and increased risks to the patient. In certain embodiments, described herein is an integrated and modular air and lighting plenum that is the primary directional lighting mounting apparatus and laminar flow diffuser of an HVAC system in a healthcare setting. The plenum provides laminar air flow from the ceiling to the room in which it is located in accordance with HVAC requirements for healthcare environment settings, by using a plurality of cylindrical airflow outlets. The use of cylindrical airflow outlets promotes laminar airflow by reducing sharp boundaries that induce turbulence (e.g., the corners of rectangular or square outlets) and creates a highly sterile environment around the patient and staff in the operating room. The surgical lights used in the integrated air and lighting plenum allow the beam direction, spot size, focal point, brightness, and color temperature of the emitted light to be controlled. The air and lighting plenum allows the lighting in the operating room to be controlled by the medical staff in terms of the light orientation and optical properties (e.g., color temperature, spot size, brightness), thus providing the needed light for staff to perform necessary functions while ensuring that medical errors are not made due to lighting issues in the operating room.

Patient warming is a significant concern in many medical situations. For example, many trauma patients admitted to a hospital emergency room are hypothermic, and if their hypothermia is not addressed, such patients can go into shock. Methods for preventing intra-operative temperature decline in surgical patients are known, and include pre-warming a blanket using a blanket warming device and then placing the warmed blanket over the patient, a convection heating device that blows heated air through a duct into a nonwoven blanket placed over the patient. Such devices have proven to be inefficient and ineffective, and can also be expensive. Moreover, blankets can limit clinical access to the patient from the topside. In certain embodiments, described herein is a patient warming system that heats from the operating table below the patient, and that can be controlled using a medical-user-interface ("MUI") in which a plurality of multiple-layer pads are adapted to operate at a low-voltage and moderate current to warm a body part of a patient. Each of the plurality of warming pads may correspond to a different area of a patient, for example, a warming pad for the head and a different warming pad for leg of the patient. Such a system allows a user, such as an anesthesiologist, doctor or nurse, to utilize the MUI to select a desired temperature for each pad, over a user-selected time period to result in a change in temperature for a chosen warming pad or pads. In some embodiments, an integrated temperature sensing system that operates to transmit signals to the MUI running on a handheld device to alert the user visually and/or audibly of monitored temperatures above or below a pre-set limit, and that further allows the user to set such limits from a graphical menu. In some embodiments, the MUI may also be configured to graphically display a time-based history of prior temperature readings from each of the plurality of warming pads, and may also display a time-based history (or trend line) of temperatures obtained from temperature sensors attached to a patient. Such an integrated patient warming system allows the medical staff to continuously and efficiently monitor the body temperature of the patient, while not limiting clinical access to the patient from the topside.

Additionally, while a number of medical device and audiovisual companies offer partial integrations solutions for the management of proprietary single devices (e.g. endoscopic surgical equipment) and management of in-room audiovisual devices, such as controllers, video management units and processing systems, as well as video recording and signal modification devices, none has developed a solution that will allow for the control of all devices, including medical devices, in an operating room. The net result has been an increase in the number of video displays (up to 8 per room), audiovisual management devices and complexity of both variety of devices and number of manufacturers' MUIs. The differences between MUIs from different vendors are a growing cause for medical errors in the operating room space, as devices and their user interfaces proliferate both in number and complexity. In some embodiments, described herein is a control system for controlling all electronic and electromechanical components of a healthcare setting (e.g., all of the electronic and electromechanical components disclosed herein) using a custom operating software. A non-exhaustive list of components and systems that may be controlled by the control system includes, for example:

Medical devices (both proprietary and any $3^{rd}$ party devices);
Electromechanical devices (e.g., robotic floor cleaner, ozone sterilization system, ambient lighting solutions etc.);
Healthcare environment information systems ("HIS");
Radiology picture archiving and communications systems ("PACS");
Audiovisual displays, control systems and conferencing systems; and
HVAC (e.g., air conditioning, heating and humidity controls).

Such an integrated control system for controlling all components of a healthcare setting allows standardization of MUI and non-medical user interfaces in the modern operating room, reducing the number of risk events for MUI errors proportionately. Using a standardized MUI provides clarity to medical staff on the inputs they are providing to medical equipment without requiring the staff to acclimate themselves to the particular equipment being used (and controlled using the MUI).

In some embodiments, integrated operating rooms can be assembled according to the present disclosure at a cost comparative to traditional operating room designs; however, the return on investment can be much higher due to savings from reducing infrastructural risks to the patient (e.g., the number of infections and diseases resulting as complications in surgery are reduced). Efficiencies gained with such an integrated operating room can allow for an extra procedure to be performed in that room each day, thereby increasing revenue to the hospital and, consequently. Thus, the ten year running cost of such an integrated operating room may be far below other traditional rooms.

Details described with respect to one feature of the invention may be applied, in certain embodiments, with respect to another feature of the invention. For example, details described with respect to a method of the invention may also be applied, in certain embodiments, with respect to a system of the invention.

Furthermore, in certain embodiments, various components, apparatus, systems, and methods described in the sister international (PCT) patent application, entitled, "Integrated Operating Room Sterilization System—Design And Components", filed on the same date herewith, and described in U.S. Provisional Patent Applications No. 62/419,391, filed Nov. 8, 2016, and No. 62/427,773, filed Nov. 29, 2016, all of which are incorporated herein by reference, can be combined with the components, apparatus, systems, and methods described herein.

In one aspect, the present invention is directed to an integrated air and lighting plenum comprising: a first (e.g., outermost) ring-shaped unit comprising general illumination lighting with translucent cover panels, wherein the first unit is modular; a second ring-shaped unit (e.g., interior to the first unit) comprising modular panels and a plurality of groups of surgical lights (e.g., two groups, three groups, four groups) each group comprising a plurality of surgical lights (e.g., wherein each group has at least three surgical lights therein), wherein: each modular panel comprises: a plurality of gas outlets (e.g., rounded holes, e.g., wherein each outlet forms a cylinder), and at least one housing for mounting a surgical light therein (e.g., a surgical light from the plurality of groups of surgical lights), the plurality of surgical lights of each group of surgical lights are equally spaced in the second unit (e.g., the surgical lights in a group of three surgical lights are spaced apart by 120 degrees relative to the center point of the second unit), and the plurality of groups of surgical lights form a first arrangement concentric to (e.g., and circumscribed by) the first unit (e.g., wherein the center of the arrangement and the center of the first unit are coincident); a third unit (e.g., interior to the second unit) (e.g., wherein the third unit is modular) concentric to (e.g., and circumscribed by) the second unit, the third unit comprising at least one group of interior surgical lights, wherein the interior surgical lights are equally spaced in the third unit forming a second arrangement concentric to the second unit (e.g., the interior surgical lights in each group are spaced apart by 120 degrees relative to the center of the units (e.g., the first unit, the second unit, and the third unit)); and one or more accessories removably mounted to the plenum (e.g., webcams, cameras, microphones, speakers, sensors), wherein the one or more accessories are for monitoring a procedure and/or providing feedback and are mounted to the plenum using a removable mounting component (e.g., a removable mounting plate, a removable housing). In certain embodiments, the plurality gas outlets produce laminar flow when gas flows therethrough. In certain embodiments, the integrated air and lighting plenum is mounted in an operating room ceiling and connected to a hospital HVAC system. In certain embodiments, the integrated air and lighting plenum comprises a flange that connects to a hospital HVAC system and directs gas through the cylindrical gas outlets. In certain embodiments, the surgical lights are removably mounted. In certain embodiments, each surgical light attaches to the integrated air and lighting plenum by an attachment that engages and disengages the respective surgical light from the housing for the surgical light by rotation of the respective surgical light (e.g., by rotation of 10 degrees, 15 degrees, 20 degrees, less than 90 degrees, more than 90 degrees). In certain embodiments, the color of the general illumination lighting is automatically changeable by a processor of a computing device (e.g., can be changed to red, blue, green, purple, orange, yellow by a processor of a server using input provided by a processor of a computing device). In certain embodiments, at least one surface comprises $TiO_2$. particles. In certain embodiments, the surgical lights comprise LEDs. In certain embodiments, lifetime of the surgical lights is extended by reducing operating temperature of the surgical lights due to gas flow through the integrated air and lighting plenum (e.g., wherein the gas flow through the cylindrical gas outlets cools the surgical lights). In certain embodiments, the first arrangement has a diameter of no less than 60 inches (e.g., no less than 70 inches, no less than 80 inches, no less than 84 inches, no less than 90 inches). In certain embodiments, the second arrangement has a diameter no more than 40 inches (e.g., no more than 30 inches, no more than 26 inches, no more than 20 inches).

In another aspect, the present invention is directed to an integrated air and lighting plenum comprising: a first (e.g., outermost) ring-shaped unit comprising general illumination lighting with translucent cover panels, wherein the first unit is modular; a second ring-shaped unit (e.g., interior to the first unit) comprising modular panels and housings for mounting a plurality of groups of surgical lights (e.g., two groups, three groups, four groups) each group of the plurality of groups comprising a plurality of surgical lights (e.g., wherein each group has at least three surgical lights therein), wherein: each modular panel comprises: a plurality of gas outlets (e.g., rounded holes, e.g., wherein each outlet forms a cylinder), and at least one housing for mounting a surgical light (e.g., a surgical light from the plurality of groups of surgical lights), and the housings for mounting the plurality of surgical lights of each group of surgical lights are equally spaced in the second unit (e.g., the housings for surgical lights in a group of three surgical lights are spaced apart by 120 degrees relative to the center point of the second unit), and the housings for mounting the plurality of groups of surgical lights form a first arrangement concentric to the first unit (e.g., wherein the center of the arrangement and the center of the first unit are coincident); a third unit (e.g., interior to the second unit)(e.g., wherein the third unit is modular) concentric to the second unit comprising housings for mounting at least one group of interior surgical lights, wherein the housings for the interior surgical lights are equally spaced in the third unit forming a second arrangement concentric to the second unit (e.g., the interior surgical lights in each group are spaced apart by 120 degrees relative to the center of the third unit); and housings for removably mounting one or more accessories to the plenum (e.g., webcams, cameras, microphones, speakers, sensors), wherein the accessories are for monitoring a procedure and/or providing feedback. In certain embodiments, the gas outlets produce laminar flow when gas flows therethrough. In certain embodiments, the integrated air and lighting plenum is mounted in an operating room ceiling and connected to a hospital HVAC system. In certain embodiments, the integrated air and lighting plenum comprises a flange that connects to a hospital HVAC system and directs gas through the cylindrical gas outlets. In certain embodiments, surgical lights are removably mounted to the housings. In certain embodiments, the surgical lights mount to the housings of the integrated air and lighting plenum by a mount that engages and disengages the respective surgical light from the housing for the surgical light by rotation of the respective surgical light (e.g., by rotation of 10 degrees, 15 degrees, 20 degrees, less than 90 degrees, more than 90 degrees). In certain embodiments, the color of the general illumination lighting is automatically changeable by a processor of a computing device (e.g., can be changed to red, blue, green, purple, orange, yellow by a processor of a server using input provided a processor of a computing device). In certain embodiments, at least one surface comprises $TiO_2$. particles. In certain embodiments, lifetime of surgical lights mounted in the housings are extended by reducing operating temperature of the surgical lights due to gas flow through the integrated air and lighting plenum (e.g., wherein the gas flow through the cylindrical gas outlets cools the surgical lights). In certain embodiments the first arrangement has a diameter of no less than 60 inches (e.g., no less than 70 inches, no less than 80 inches, no less than 84 inches, no less than 90 inches). In certain embodiments, the second arrangement has a diameter no more than 40 inches (e.g., no more than 30 inches, no more than 26 inches, no more than 20 inches).

In another aspect, the present invention is directed to a surgical light for lighting a patient, comprising: a housing having a transparent cover (e.g., made of plastic, acrylic, glass); an outer circular arrangement of outer lighting arrays each comprising a plurality of lights, wherein the outer circular arrangement is adjustable; an inner circular arrangement of inner lighting arrays comprising a plurality of lights, wherein the inner circular arrangement is adjustable; a power connection; a data connection (e.g., Ethernet, Bluetooth, Wi-Fi, fiber optics); a multi-axis (e.g., two-axis, three-axis) gimbal apparatus disposed within the housing and connected to the outer circular arrangement and the inner circular arrangement; and at least one motor disposed within the housing to manipulate the gimbal system in order to adjust the outer circular arrangement and/or the inner circular arrangement (e.g., tilting and rotating the outer circular arrangement and/or inner circular arrangement) (e.g., to change the spot size (e.g., beam diameter)). In certain embodiments, spot size of the surgical light is adjustable (e.g., wherein the spot size of the outer lighting arrays and/or inner lighting arrays is adjustable). In certain embodiments, the spot size of the surgical light is adjustable from 3.5 to 18 inches. In certain embodiments, color temperature of the surgical light is adjustable (e.g., wherein the color temperature of the outer lighting arrays and/or inner lighting arrays is adjustable). In certain embodiments, the color temperature of the surgical light is adjustable from 3000 to 7000 Kelvin at a constant brightness. In certain embodiments, brightness, color temperature, beam diameter, and beam direction are adjustable. In certain embodiments, the surgical light is adjusted using input to the data connection by a remote device. In certain embodiments, the housing is sealed to provide a hermetic seal. In certain embodiments, the outer circular arrangement comprises at least 16 outer lighting arrays. In certain embodiments, the outer lighting arrays in the outer circular arrangement can be turned off while inner lighting arrays in the inner circular arrangement remain on. In certain embodiments, the outer lighting arrays in the outer circular arrangement and the inner lighting arrays in the adjustable inner circular arrangement comprise LEDs.

In another aspect, the present invention is directed to a system (e.g., a spot-group) for lighting an operation, comprising: three surgical lights arranged to form the vertices of an equilateral triangle such that shadows are reduced or eliminated when the three surgical lights focus on a common point in space. In certain embodiments, the surgical lights are individually addressable by the data connection (e.g., to adjust brightness, color temperature, beam direction, focal point, and power state (e.g., on or off)). In certain embodiments, light from each of the surgical lights is adjusted (e.g., adjusting brightness and/or color temperature) individually (e.g., to accentuate the appearance of tissue in a surgical incision). In certain embodiments, the system comprises a fourth surgical light focused on the common point in space.

In another aspect, the present invention is directed to a method for controlling an array of surgical lights corresponding to a surgical lighting system for an operation, the method comprising: providing, by a processor of an electronic device, for display on a screen, a graphic representation of a plurality of surgical lights corresponding to the surgical lighting system; receiving, by the processor, from a user interface of the electronic device, a selection of at least one of a direction to point at least one surgical light of the plurality of surgical lights corresponding to the surgical lighting system and a setting of the at least one surgical light of the plurality of surgical lights corresponding to the surgical lighting system. In certain embodiments, the selection is of the setting of the at least one surgical light, and the setting is at least one member selected from a group consisting of: spot size, color temperature and brightness. In certain embodiments, the at least one surgical light is a spot-group comprising three surgical lights. In certain embodiments, the method comprises: providing, by the processor of the electronic device, for display on the screen, a graphic representation of a field-of-view of an overhead monitoring camera. In certain embodiments, the user interface comprises at least one coarse adjust icon and at least one fine adjust icon for adjusting the focal point of the at least one surgical light.

In another aspect, the present invention is directed to a system for controlling an array of surgical lights, the system comprising: a plurality of surgical lights; an overhead monitoring camera; an electronic device, comprising a processor, and a memory having instructions stored thereon, wherein the instructions, when executed by the processor, cause the processor to: provide, for display on a screen, a graphic representation of the plurality of surgical lights and field-of-view of the overhead monitoring camera, and receive, from a user interface, a selection of at least one of a focal point of at least one surgical light of the plurality of surgical lights and a setting of the at least one surgical light. In certain embodiments, the system comprises a wireless computing device, wherein the user interface is displayed on the wireless computing device. In certain embodiments, the selection is of the setting of the at least one surgical light, and the setting is a member selected from the group consisting of: spot size, color temperature, and brightness. In certain embodiments, the electronic device is a server. In certain embodiments, the at least one surgical light is a spot-group comprising three surgical lights. In certain embodiments, the user interface comprises at least one coarse adjust icon and at least one fine adjust icon for adjusting the focal point of the at least one surgical light. In certain embodiments, the color temperature ranges is in a range from 3000 Kelvin (K) to 7000 K at a constant brightness. In certain embodiments, the spot size is in a range from 3.5 inches to 18 inches.

In another aspect, the present invention is directed to a patient warming system for stabilizing and/or heating and cooling a patient, comprising: a plurality of solid-surface sections arranged for attachment to a surgical table, that form a solid-surface layer, wherein at least one of the plurality of solid-surface sections comprises a power connector for connection to an external power source; and a warming pad layer comprising a plurality of warming pads configured for removable connection to the plurality of solid-surface sections, wherein each warming pad of the plurality of warming pads comprises: a foam insulation layer; a distributed heating element layer having a warming-pad power connection for connection to the power connector; an isothermal layer (e.g., for maintaining an even distribution of heat throughout the warming pad to prevent hot spots from forming); and a flexible waterproof layer that covers the foam insulation layer, distributed heating element layer, and isothermal layer, wherein power supplied to the warming-pad power connection of the distributed heating element layer of the respective warming pad is used to provide a user-selected uniform temperature over the surface of the flexible waterproof layer in order to prevent hot spots. In certain embodiments, the patient warming system comprises: a heat sensor embedded in each warming pad of the plurality of warming pads for detecting temperature, wherein the heat sensor is adjacent to the isothermal layer; a heat sensor data connector connected to the heat sensor, wherein the heat sensor data connector is located on a side of the one of the plurality of warming pads; and a data connector in the solid-surface layer for connection to the heat sensor data connector for obtaining temperature data about the isothermal layer for use in adjusting the temperature of the respective warming pad. In certain embodiments, each warming pad of the plurality of warming pads comprises a cooling layer comprising an arrangement of cooling liquid conduit.

In another aspect, the present invention is directed to a patient warming pad for stabilizing and/or heating and cooling a patient, the patient warming pad comprising: a foam insulation layer for contacting a surgical table; a heating element layer coupled to the foam insulation layer, the heating element layer comprising a heater power connector; an isothermal layer for maintaining uniform temperature across its surface area (e.g., to prevent the formation of hot spots), wherein the isothermal layer is positioned between the heating element layer and the patient when the patient is laying on the patient warming pad; and a flexible waterproof cover layer coupled to the isothermal layer. In certain embodiments, the patient warming pad comprises an electronic insulation layer located at a location of at least one of above and below the isothermal layer. In certain embodiments, the patient warming pad comprises a disposable cover configured to fit around the patient warming pad. In certain embodiments, the patient warming pad comprises a cooling layer comprising an arrangement of cooling liquid conduit.

In another aspect, the present invention is directed to a patient warming pad system for alerting a user of a patient's abnormal skin surface temperature, the system comprising: one or more patient warming pads; a processor; a memory having instructions stored thereon, wherein the instructions, when executed by the processor, cause the processor to: automatically display a graphic wireframe representation of portions of a patient's body and a graphical representation corresponding to each of the one or more patient warming pads showing a temperature from each of the one or more patient warming pads; automatically determine that the temperature from at least one of the one or more patient warming pads is above or below a predetermined temperature; and at least one of: automatically alerting the user that the temperature of at least one of the one or more patient warming pads is above or below the predetermined temperature; and automatically controlling power to the at least one of the one or more patient warming pads to decrease or increase the temperature.

In another aspect, the present invention is directed to a patient warming pad system for alerting a user of abnormal skin surface temperature of a patient, the system comprising: one or more patient warming pads; one or more skin surface temperature sensors for monitoring the patient's skin surface temperature (e.g., by attaching the one or more skin surface temperature sensors to the patient), wherein each of the one or more skin surface temperature sensors corresponds to a respective warming pad of the one or more patient warming pads; a computing device (e.g., desktop computer, tablet, smartphone, laptop computer) comprising a processor, and a memory having instructions stored thereon, wherein the instructions, when executed by the processor, cause the processor to: display a graphic wireframe representation of portions of a patient's body and a graphical representation corresponding to each of the one or more patient warming pads showing a skin surface temperature for each of the one or more patient warming pads as measured by the corresponding at least one skin surface temperature sensors; automatically determine that the skin surface temperature for at least one of one or more patient warming pads is above or below a predetermined temperature; and at least one of: automatically alerting the user that the skin surface temperature for the at least one of the one or more patient warming pads is above or below the predetermined temperature; and automatically controlling power to the at least one of the one or more patient warming pads to decrease or increase its temperature. In certain embodiments, the graphical representation indicates a warming pad temperature for each of the one or more patient warming pads. In certain embodiments, the plurality of solid-surface sections comprise a surface made from a material with a low dielectric constant to reduce electrostatically attracted substances. In certain embodiments, the patient warming pad system comprises one or more sensors for attaching to the patient's skin in order to monitor the patient's skin temperature for a reduced likelihood of the patient developing skin burns.

In another aspect, the present invention is directed to an integrated control system for controlling components of a setting of a healthcare environment, the integrated control system comprising: one or more wireless computing devices (e.g., tablets, mobile phones, laptops); one or more displays (e.g., high definition displays); a plurality of components of the setting, wherein at least one component of the plurality of components is a member selected from the group consisting of: an ozone sterilization system, an integrated air and lighting plenum, a surgical lighting system, a pass-through logistics cabinet, and a floor sterilization robot; and a server comprising: a connection for connecting to a remote healthcare environment information system (e.g., database), and a receiver and a transmitter for communicating data (e.g., input data) between the plurality of components of the setting, medical equipment connected to one of the plurality of components, the remote healthcare environment information system, the one or more wireless computing devices and the one or more high definition displays. In certain embodiments, the server transmits a plurality of feeds of data to a first display of the one or more displays such that each of the plurality of feeds of data is displayed simultaneously on a portion of the first display. In certain embodiments, the system comprises a plurality of different operational states (e.g., a normal operational state, a systems configuration state, a systems testing state) (e.g., wherein each of the plurality of operational states allows some functionalities to remain operable while inhibiting other functionalities).

In another aspect, the present invention is directed to a method for displaying data received from a medical apparatus from an outside vendor on a computing device in a standardized data format using generalized software, the method comprising: recognizing, by a processor of a computing device (e.g., a server), that a medical apparatus has been connected (e.g., directly or indirectly) to the computing device; identify, by the processor, the medical apparatus; manipulating, by a device bridge module, data received from the medical apparatus from an apparatus format to the standardized data format (e.g., data formatted in a standardized way), thereby creating standardized data; transmitting, by the processor, the standardized data to a second computing device (e.g., a tablet, wireless computing device, mobile phone); and displaying, by a view model bridge module, on a display of the second computing device, a standardized visualization of the standardized data. In certain embodiments, the second computing device is the first computing device.

In another aspect, the present invention is directed to a system for displaying standardized data received from medical apparatus from an outside vendor on a computing device using generalized software, the system comprising: a user interface for providing a standardized visualization; a computing device for communicating with a medical apparatus;

a processor; a memory having instructions stored thereon, wherein the instructions, when executed by the processor, cause the processor to: recognize, by the processor, that the medical apparatus has been connected (e.g., directly or indirectly) to the computing device; identify, by the processor, the medical apparatus; manipulate, by the processor, data received from the medical apparatus from an apparatus format to the standardized data format (e.g., data formatted in a standardized way) using a device bridge module, thereby creating standardized data; and transmitting, by the processor, the standardized data to a second computing device (e.g., a tablet, wireless computing device, mobile phone); and the second computing device for displaying on a display of the second computing device, a standardized visualization of the standardized data using a view model bridge module. In certain embodiments, the second computing device is the first computing device.

In another aspect, the present invention is directed to a system for communicating between a user interface of a computing device and a medical apparatus, the system comprising: a device bridge module that manipulates data between an apparatus format for the medical apparatus and a standardized format for the computing device; a generalized software that enables the user interface to communicate with the medical apparatus, wherein the generalized software receives and transmits standardized data between the device bridge module and the view model bridge module; and a view model bridge module that receives data in the standardized format from the device bridge module and provides the data in the standardized format for display on the computing device and provides commands from the user interface of the computing device to the device bridge module for manipulation and communication to the medical apparatus.

In another aspect, the present invention is directed to a system for displaying medical data (e.g., video) on one or more monitors in a setting of a healthcare environment, the system comprising: a plurality of high definition monitors (e.g., 4K 3D monitors) (e.g., for mounting in/on one or more walls of the setting of the healthcare environment); a router for routing a plurality of input medical data feeds (e.g., medical data feeds from a plurality of hardware components of a healthcare environment, e.g., cameras, microphones, conference line, ENZO, anesthesia system, HIS, graphical interface (e.g., iPad) mirror); and a plurality of medical data feed splitters, wherein: the router routes the plurality of input medical data feeds to at least one of the plurality of medical data feed splitters, each medical data feed splitter combines the input medical data feeds received by the respective medical data feed splitter into a data output feed, and each of the medical data feed splitters is connected to one of the high definition monitors such that the data output feed from the respective medical data feed splitter is displayed on the high definition monitor (e.g., to consolidate data from multiple sources for organized display on a common screen). In some embodiments, the medical data is a member selected from the group consisting of a video, an image, an audio, a text file, and any combination thereof. In some embodiments, connections between the one or more high definition monitors and the one or more medical data feed splitters and connections between the one or more medical data feed splitters and the router and connections that provide the one or more input medical data feeds are 12G SDI connections. In some embodiments, connections between the one or more high definition monitors and the one or more medical data feed splitters and connections between the one or more medical data feed splitters and the router and connections that provide the one or more input medical data feeds are 25G SDI connections.

DEFINITIONS

In order for the present disclosure to be more readily understood, certain terms used herein are defined below. Additional definitions for the following terms and other terms may be set forth throughout the specification.

In this application, the use of "or" means "and/or" unless stated otherwise. As used in this application, the term "comprise" and variations of the term, such as "comprising" and "comprises," are not intended to exclude other additives, components, integers or steps. As used in this application, the terms "about" and "approximately" are used as equivalents. Any numerals used in this application with or without about/approximately are meant to cover any normal fluctuations appreciated by one of ordinary skill in the relevant art. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Proximity: As the term is used herein, any object, device, component, system, part thereof, or subpart thereof is "proximal" to or in "proximity" to any other object, device, component, system, part thereof, or subpart thereof when they are physically close. In some embodiments, a part of a system may be in proximity to an object when it is inside the same room as the object. In some embodiments, an object may be in proximity to another object when both objects are on the same wall. In some embodiments, an object may be in proximity to a component when it is outside the room the component is in, but no more than some physical distance away from the component (e.g., apart by no more than 5 centimeters, no more than 10 centimeters, no more than 1 meter, no more than 2 meters, no more than 10 meters). The physical distance which objects may be separated while being in proximity to each other may depend on the size and function of the objects.

Supplies: As used herein, the term "supplies" refers to medical items, equipment, or instrumentation used to treat, monitor, or perform a procedure on a patient. In some embodiments, supplies are disposable. In some embodiments, supplies are non-disposable and may require sterilization after use. The term "supplies" may refer to a single item, instrument, or piece of equipment or it may refer to multiple items, instruments, or pieces of equipment, or combinations thereof.

Conduit: As used herein, conduit refers to cables, hoses, tubes, or wires that provide one or more utilities to a device. In some embodiments, conduit is routed through a floor or ceiling to provide a connection from a main utility line of a healthcare environment or setting within a healthcare environment to a system or component of the present invention. In some embodiments, conduit connects to a system or component of the present invention to allow medical staff to perform one or more functions of a treatment or procedure (e.g., a surgical procedure). Conduit is used to transport one or more utilities needed for a treatment or procedure. Utilities may be gas, electricity, fluids (e.g., water), vacuum, light, video, data (e.g., provided by USB, Bluetooth, Ethernet, fiber optics), or other similar utilities required to operate medical equipment for the treatment of procedures (e.g., surgical procedures).

Healthcare environment: As used herein, a healthcare environment is a location where healthcare is given to a patient. In some embodiments, a healthcare environment is a hospital, a clinic, a health emergency facility, an urgent care facility, a doctor's office, or a group of one or more rooms designed for surgery or patient treatment. A setting of a healthcare environment may be a room, a group of rooms, a ward, a department, or a general space in which medical care such as treatments or procedures is administered or performed. In some embodiments, a setting of a healthcare environment is an operating room or operating suite.

Wireless computing device: As used herein, a wireless computing device is a portable device that connects to other computing devices wirelessly. In some embodiments, a wireless computing device comprises a battery such that it can be operated without a physical power connection. A wireless computing device may be a tablet, a laptop, a mobile phone, a personal digital assistant, a mobile device with a touchscreen (e.g., an iPod™), or other similar mobile computing devices that communicate wirelessly. In certain embodiments, a wireless computing device is an iPad™. A wireless computing device may communicate with other computing devices, sensors, or electronic components using any wireless protocol known in the art. For example, a wireless computing device may communicate using Wi-Fi (e.g., using an 802.11 standard), 3G, 4G, LTE, Bluetooth, or ANT. In some embodiments, a wireless computing device is a stationary computer that connects to other computing devices wirelessly (e.g., using a wireless card).

BRIEF DESCRIPTION OF THE DRAWINGS

Drawings are presented herein for illustration purposes, not for limitation. The foregoing and other objects, aspects, features, and advantages of the invention will become more apparent and may be better understood by referring to the following description taken in conjunction with the accompanying drawings, in which:

FIG. 3E shows a block diagram of a method for verifying a hermetic seal of one or more rooms prior to allowing a sterilization procedure to proceed, according to an illustrative embodiment of the invention;

FIG. 4H shows the results of the pack search of FIG. 4G, according to an illustrative embodiment of the invention;

FIG. 4M shows a detailed view of the two dimensional "cabinet view" array in FIG. 4L, according to an illustrative embodiment of the invention;

FIG. 4O shows the graphical user interface when the "Shelf Display" option is selected, wherein the search results panel shows all settings of the healthcare environment with pass-through logistics cabinets installed, according to an illustrative embodiment of the invention;

FIG. 4Q shows the graphical user interface when a supply (located in location C3) has been delivered to an operating room but removed from its location prior to the scheduled surgery in which it was intended to be used, wherein that supply is denoted by red location text, according to an illustrative embodiment of the invention;

FIG. 4T shows a block diagram of a method of using a pass-through logistics cabinet to reduce spread of contamination from the pass-through logistics cabinet, according to an illustrative embodiment of the invention;

FIG. 6D shows a block diagram of a method for displaying data received from a medical apparatus from an outside vendor on a computing device in a standardized data format using generalized software, according to an illustrative embodiment of the invention;

DETAILED DESCRIPTION

It is contemplated that systems, devices, methods, and processes of the claimed invention encompass variations and adaptations developed using information from the embodiments described herein. Adaptation and/or modification of the systems, devices, methods, and processes described herein may be performed by those of ordinary skill in the relevant art.

Throughout the description, where articles, devices, and systems are described as having, including, or comprising specific components, or where processes and methods are described as having, including, or comprising specific steps, it is contemplated that, additionally, there are articles, devices, and systems of the present invention that consist essentially of, or consist of, the recited components, and that there are processes and methods according to the present invention that consist essentially of, or consist of, the recited processing steps.

It should be understood that the order of steps or order for performing certain action is immaterial so long as the invention remains operable. Moreover, two or more steps or actions may be conducted simultaneously.

The mention herein of any publication, for example, in the Background section, is not an admission that the publication serves as prior art with respect to any of the claims presented herein. The Background section is presented for purposes of clarity and is not meant as a description of prior art with respect to any claim. Headers are provided for the convenience of the reader and are not intended to be limiting with respect to the claimed subject matter.

The present disclosure describes the following: pass-through logistics cabinets, ozone sterilization systems, integrated lighting and air plenums, patient warming pad systems and components, floor cleaning and sterilization robots, systems for integrating such components into an operating room and with wireless control, and software for controlling such components. In some embodiments, multiple components and systems of the present disclosure are present in one setting (e.g., an operating room) and are controlled by a single wireless device (e.g., a tablet) or a group of wireless devices connected to all the components and systems through a server. In certain embodiments, a single component or subset of the components are integrated into an existing setting (e.g., a small operating room or an emergency room) to reduce some risks otherwise present in the room. For example, in some embodiments, a patient warming pad is used in an emergency room to monitor and stabilize patient temperature to reduce the risk of hypothermia, hyperthermia, and skin burns associated with a schedule of periodic monitoring by emergency room staff.

Real-Time Patient Warming and Total Body Heat Loss Monitoring System

Figure 1A:
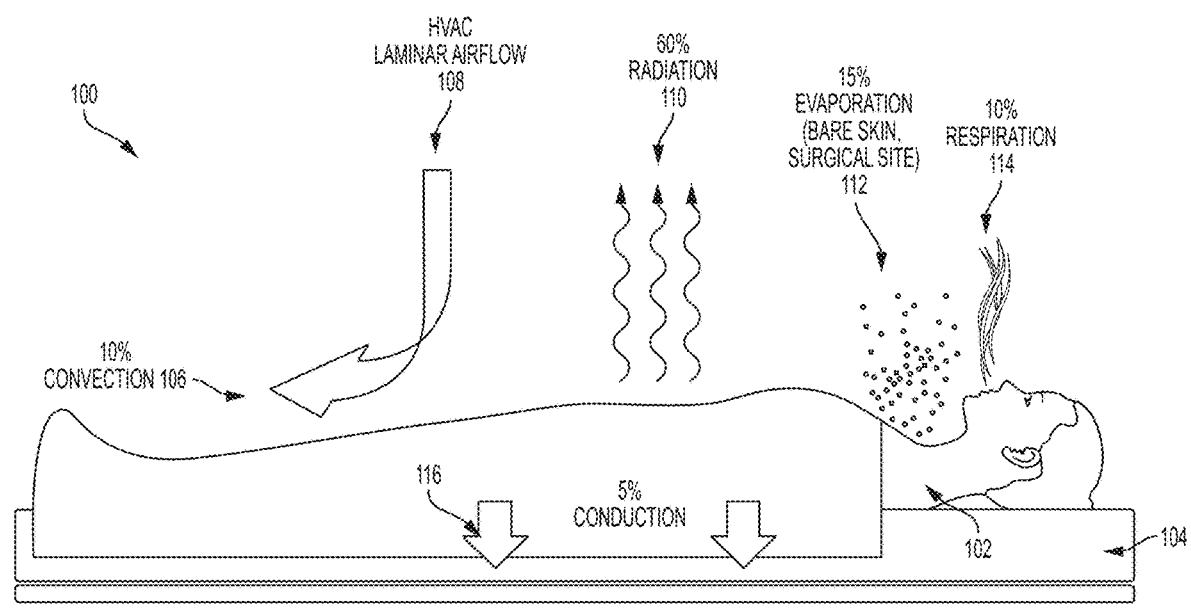
FIG. 1A shows a side view of a patient on an operating table, and the various types of heat loss occurring during surgery.
Figure 1B:
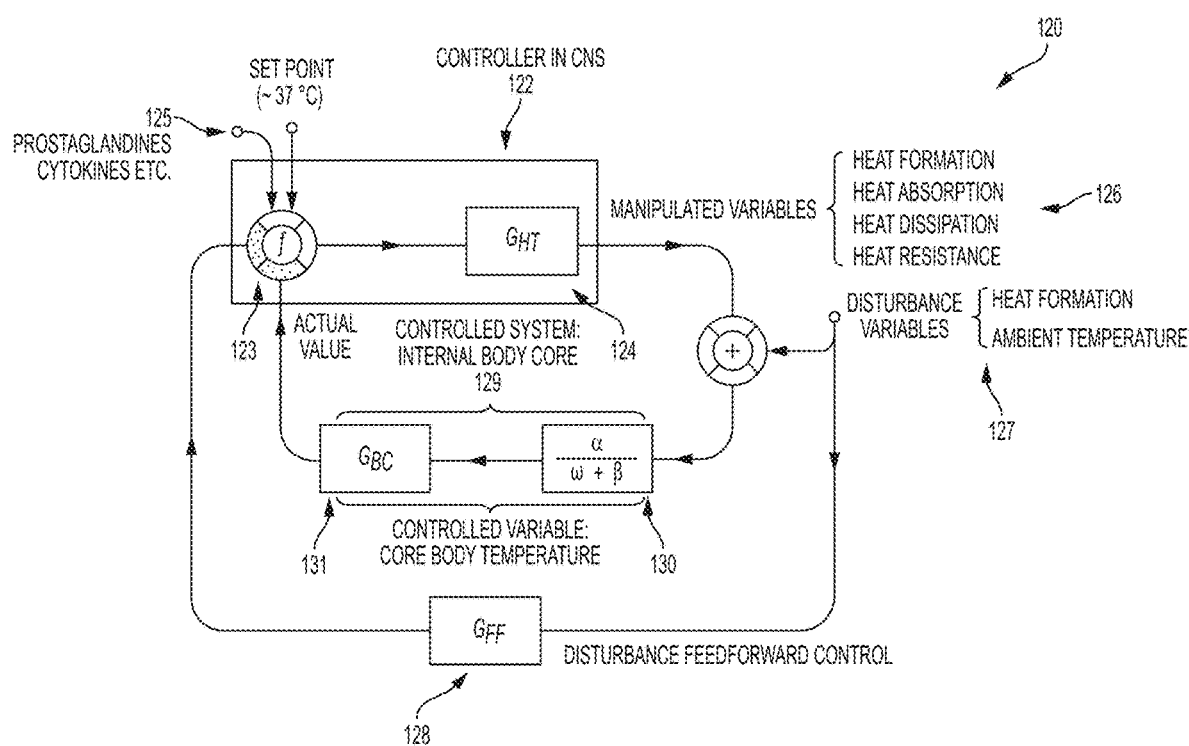
FIG. 1B shows a thermoregulation diagram depicting a patient's internal control feedback system that regulates core heat loss and gain as a result of external heat sources and sinks.

The human body has an internal control mechanism to monitor and regulate the core temperature of the body. The thermoregulation diagram of FIG. 1B shows the body's internal control feedback system that regulates internal body core heat loss and gain as a result of external heat sources and sinks. An example of an external heat source is heater that increases the temperature of a room. Examples of heat sinks include but is not limited to, the ambient air (convection (106 of FIG. 14)), radiation (110 of FIG. 1A), evaporation (112 of FIG. 14), respiration (114 of FIG. 1A), and conduction (116 of FIG. 14). The human thermoregulation control system (as shown in FIG. 1B) has two major interacting physical elements. The first is a controller in the Central Nervous System (CNS), also known as the CNS controller, 122 (for example, the human brain), and the second is a controlled system 129 (for example, the internal human body core). The two physical elements of the control system interact with each other directly, or through a disturbance feedforward control 128. Other elements to the thermoregulation control are the disturbance variables 127, manipulated variables 126, and physiological inputs to the CNS controller 125. The disturbance feedforward receives the disturbance variables, or external variables (e.g. outside the human body) as input. Examples of disturbance variables include the ambient temperature of a room, heat formation in the room etc. . . . . . Thus the output of the disturbance feedforward control that serves as an input to the CNS controller is a signal to increase or decrease the core body temperature based on the current state of the disturbance variables. The second input to the CNS controller are internal inputs (e.g. from inside the human body). These are physiologically active compounds like prostaglandins, cytokines, and so forth that play a direct or indirect role in core temperature regulation. Finally, the CNS controller is also provided with a set point to determine the target temperature to be achieved (for example, 37° C. for the human body), and the current core body temperature. Based on the aforementioned four inputs, the CNS controller decides if the human body needs to produce or dissipate heat. This is denoted as the manipulated variables in the thermoregulation diagram. Examples of manipulated variables are heat formation, heat absorption, heat dissipation, and heat resistance. The manipulated variables, along with the disturbance variables are fed as inputs to the controlled system (for example, the human body core), which provides a signal to the core body to either increase heat production or dissipation in order to achieve the set point temperature.

The above described feedback control is not active in many instances, for example during surgery. Thus, patient warming is a significant concern in many medical situations. For example, many trauma patients admitted to a hospital emergency room are hypothermic, and if their hypothermia is not addressed, such patients can go into shock. Similarly, patients may experience hypothermia during or after surgery in a hospital operating room environment with detrimental physiological consequences. Hypothermia is a natural defense mechanism of the body that reduces the blood flow to the appendages in order to protect the vital organs, and can be treated by warming the patient.

It is generally known that the risk of unintentional hypothermia in a surgical patient is greater after inducing general anesthesia as the patient's core body temperature generally drops up to two degrees Centigrade (2° C.) during the first hour of surgery, and may fall another 1° C. to 1.5° C. thereafter. During surgical procedures, under either regional or general anesthesia, normal heat preservation mechanisms are lost and consequent loss of both body heat and temperature occur. The most important measure of body heat is called "core temperature," and is usually monitored by various methods during surgical anesthesia. Normal core temperature is around 37 degrees centigrade (98.8 Fahrenheit). Negative effects to the body begin to occur when core temperature drops below 36° C. These effects include cardiovascular (reduced cardiac output, arrhythmias, increased risk of cardiac infarcts), reduced immunity function and infection resistance (20° C. drop results in a tripled risk of surgical site infection), kidney effects (reduced urinary output), reduced oxygen delivery to tissues, increased blood clotting problems, and increase risk of pressure sores due to reduced blood circulation in the skin. Decreased heat production by the body during hypothermia causes a circular negative feedback resulting in yet increased temperature drop due to this loss of heat production. Workflow efficiency effects include an increased time-to-wake, confusion, and prolonged time spent in the recovery room. Increased recovery room time often results in the domino effect of creating workflow chokepoints for patients who are ready to leave the operating room, causing an increase in so-called "on hold" times. Furthermore, delayed wound healing or significant renal or cardiac events may lead to prolonged hospital stays for patients who experience significant surgical decreases in core body temperature.

Core temperature usually drops about 10° C. during the first hour of surgery, due to redistribution of body heat after anesthesia induced loss of the body's heat retention mechanisms (peripheral vasoconstriction, pilo-erection, closure of skin pores and muscular heat production due to shivering) that take effect in normal conditions of exposure to cold environments. Thereafter heat loss increases at a rate of about 1-20° C. over the next 2 hours (and beyond during longer surgeries) as the combination of events (cool intravenous fluids, exposure, low room temperature etc.) contribute to the increasing disassociation between heat loss and reduced body heat production during anesthesia. The various types of heat loss during surgery of a patient are shown in FIG. 1A.

Preventing unintentional hypothermia helps avoid many postoperative complications and their associate costs. For example, in one study, the incidence of culture-positive wound infections was three times higher in hypothermic patients as compared to normothermic patients. Studies also show that hypothermic patients were up to three times more likely to have ECG events, myocardial ischemia and ventricular tachycardia. In addition, patients with hypothermia were shown to have significantly higher incidences of organ dysfunction and death, and bleeding at the end of surgery is more common in such patients. It is thus increasingly evident that maintaining normothermia in patients undergoing surgery improves outcomes and shortens recovery and healing times. It is also known that "time-to-wake" times are extended for hypothermic patients, and this period can extend anywhere from minutes in short time cases, to 12 hours in operations that last more than 10 hours (e.g., prolonged neurosurgical and organ transplant operations). The converse is of immense value to hospitals, when time-to-wake times approach zero for patients who are normothermic at the end of an operation, both in operational time costs (less time in the operating theater and in the recovery room, thus avoiding "On Hold" type delays common in larger hospital operating room settings), and the attendant respiratory and surgical site infection risks associated with delayed times-to-wake.

Methods for preventing intra-operative temperature decline in surgical patients are known, and include pre-warming a blanket using a blanket warming device and then placing the warmed blanket over the patient. A convection heating device is also available that blows heated air through a duct into a nonwoven blanket placed over the patient. Such nonwoven blankets have channels for the heated air to circulate in, and some are disposable so that cleaning is unnecessary. But the high temperatures often reached by the heated air duct that feeds hot air to the blanket, which is usually in close proximity to an anesthetized patient, has raised concerns. In addition, the convection heating device and the pre-warmed blankets both warm a patient inefficiently from above. Moreover, blankets can limit clinical access to the patient from the topside. Such devices have proven to be inefficient and ineffective, and can also be expensive due to the costs involved with replacing the disposable nonwoven blankets, supplying relatively large amounts of energy, and providing maintenance in the clinical environment.

Other heating apparatus using convection currents or central air-conditioning have been used, but such heating devices and methods have numerous drawbacks including overheating or under-heating the patient. Convection heating devices may also excessively heat the surrounding environment resulting in overheating the surgical or hospital room staff, and which may also waste energy. In addition, air convection units are bulky and take up considerable and valuable space in an operating room, for example, due to the required extended conduit, which can also create obstacles to free movement around the patient during surgery. Furthermore, due to the lack of real-time temperature feedback from the patient such heating units may cause the patient to suffer localized overheating and/or exposure to a burn injury.

Typically, anesthesiologists measure only core temperature (by various means), or surface temperature, utilizing a single local device on the forehead. They have no means to accurately calculate total body heat loss, as measuring methodologies and devices for this are not currently available. If core temperature drops one degree, this knowledge usually come to be know well after an hour of progressive total body heat loss.

Therefore an inherent design and use problem with conventional heating systems is that they lack the ability to measure local regional skin temperature, resulting in unexpected skin burns when a heating unit overwarms regional skin areas, for instance in patients who lack the ability to move heat away from the area of exposure to deeper tissues by way of disturbed capillary flow or transduction. This is particularly troublesome in patients with chronic skin disorders associated with such diseases as diabetes mellitus, obesity, scleroderma and others, as well in patients who are malnourished (e.g. cancer and chronic infection patients), in patients undergoing cardiac standstill or vascular bypass or replacement, and in small children in whom core temperature can fluctuate quite rapidly.

It is also known that heating from below is more efficient and safer that heating from above, as most conventional heating systems do.

There is a need for a low-maintenance, real-time feedback warming pad system for warming surgical patients to a desired temperature that avoids high temperatures, is energy efficient and quiet, provides real-time feedback of local skin temperatures, and otherwise overcomes the problems associated with conventional devices. Such a warming system should also provide a minimal footprint so as not to impede operating room personnel, and should be capable of maintaining the strict hygiene requirements of a hospital environment.

Figure 1C:
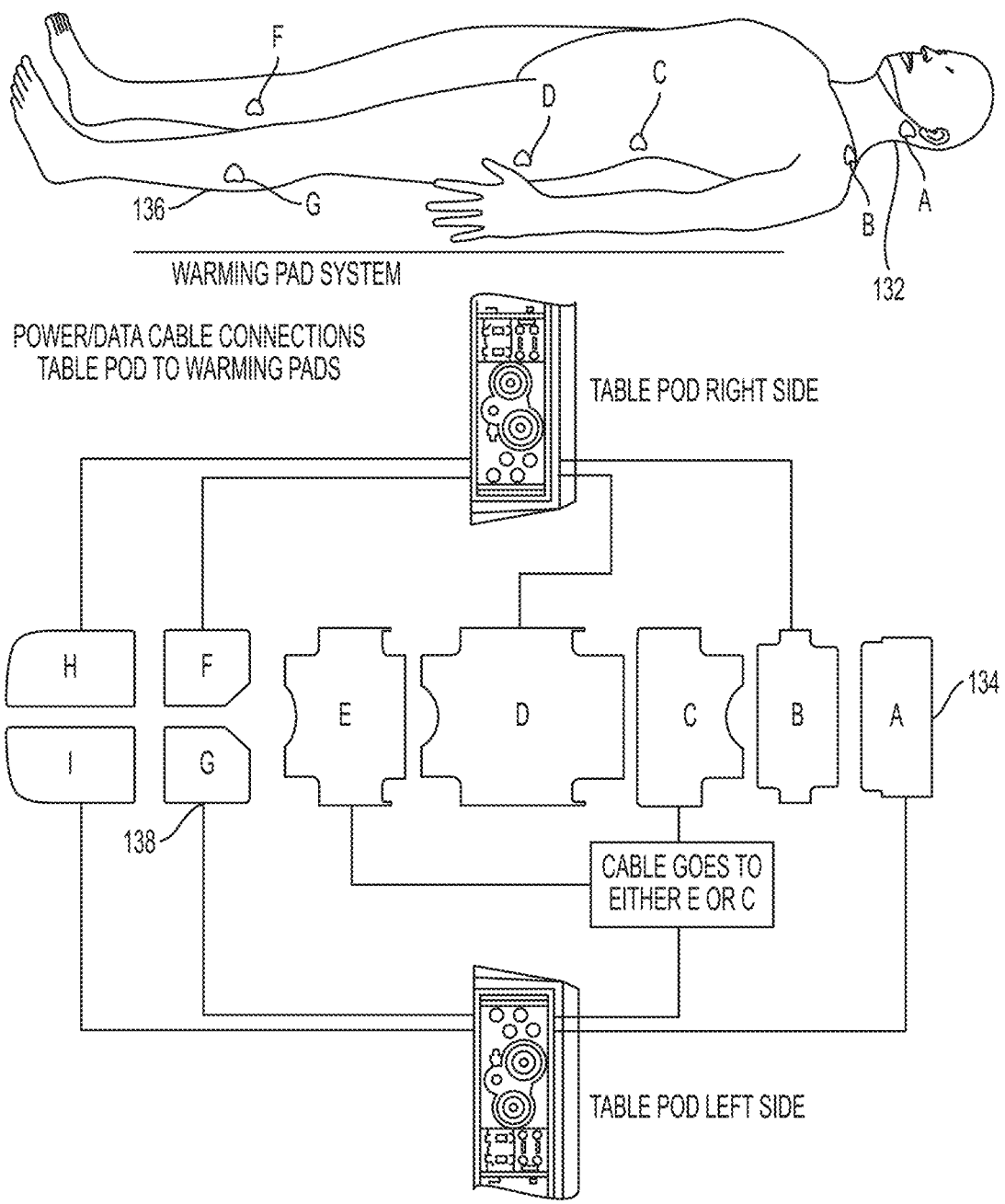
FIG. 1C shows a side view of a patient and a top view of a patient warming pad system, wherein the letters A-G are used to show the correspondence between different parts of the patient's body and different warming pads in the system, according to an illustrative embodiment of the invention.

In certain embodiments, described herein is a patient warming system that can be controlled using a medical-user-interface ("MUI") in which a plurality of multiple-layer pads are adapted to operate at a low-voltage and moderate current to warm a body part of a patient. Each of the plurality of warming pads may correspond to a different area of a patient, as shown in FIG. 1C where pads A-G each correspond to a limb or region of the patient. For example, the patient's head 132 corresponds to head pad A 134 and the patient's left leg 136 corresponds to left leg pad G 138. In certain embodiments, the multiple layer composition of each warming pad includes a foam insulation layer, a heating element layer, an isothermal layer, sensors for monitoring the temperature of the isothermal layer, a flexible waterproof cover layer and a disposable, sterile and waterproof outer envelope. The multiple-layer warming pads transmit and receive signals concerning the temperature of each pad, and, in some embodiments, the medical user interface may be a graphical computer interface (e.g., a graphical user interface (GUI)) provided on, for example, a wireless computing device display screen for a user to manipulate in order to control the warming pads. In some embodiments, the GUI is configured to operate wirelessly and provides graphical displays of the patient's body and a current temperature and the intended temperature of each warming pad, and the current skin temperature of each body part from temperature sensors attached to a patient. A user, such as an anesthesiologist, doctor or nurse, can utilize the GUI to select a desired temperature for each pad, and may do so over a user-selected time period to result in a change in temperature for a chosen warming pad or pads. In some embodiments, the patient warming pads are capable of supplying a surface heating temperature in the range of approximately ninety-two degrees Fahrenheit (92° F.), which is about 33.3° Celsius (C)) to about 106° F. (41.1° C.). In certain embodiments, an integrated temperature sensing system that operates to transmit signals to the GUI running on a handheld device to alert the user visually and/or audibly of monitored temperatures above or below a pre-set limit, and that further allows the user to set such limits from a graphical menu. In some embodiments, the GUI may also be configured to graphically display a time-based history of prior temperature readings from each of the plurality of warming pads, and may also display a time-based history (or trend line) of temperatures obtained from temperature sensors attached to a patient.

In certain embodiments, a patient warming system may comprise subsections such as a head segment, a shoulder segment, a chest segment, an abdomen segment, a right leg segment and a left leg segment. These segments are supported by a surgical table. The surgical table may be motorized, and each of the segments may be movably connected to at least one other segment. In addition, each segment may be individually supported by a movable support structure that may include one or more servo-motors that are controllable to, for example, raise, lower and/or tilt one or more of the segments to move a corresponding body part of a patient. Thus, the surgical table may be designed to allow for a wide range of tilting and height configurations to accommodate the positioning of a patient for various surgical procedures, and to move into a comfortable orientation for a surgeon. In particular, some or all of the segments of the surgical table can be lowered, elevated, tilted and/or otherwise positioned or adjusted to accommodate and position a particular patient's body for a procedure, and/or to accommodate a particular surgeon's preferences. In certain embodiments, a tethered, hand-held controller is provided that includes buttons and/or knobs or other controls for use by an operator (such as a doctor or nurse) to position the surgical table segments so that the patient can be oriented on the surgical table in a desired and/or customized position.

In certain embodiments, the warming pad system includes a solid-surface layer and a low-voltage warming pad layer. The solid-surface layer includes a plurality of solid-surface sections that are configured and/or sized to conform to, or match up with, the surgical table segments. In particular, the solid-surface layer includes a head surface section, a shoulder surface section, a chest surface section, an abdomen surface section, a right leg surface section and a left leg surface section. In some embodiments, the solid-surface sections are semi-permanently affixed to a corresponding surgical table segment. In certain embodiments, each of the solid-surface sections may be approximately half an inch to three inches thick (e.g., approximately one centimeter to about seven and one-half centimeters thick). Each sold-surface section, in some embodiments, is non-porous, has a low thermal conductivity closed-cell construction (e.g., to minimize the accretion of dust and other electro-statically attracted substances), and is made of a material that discourages bacterial or microbial growth. For example, each of the solid-surface sections may be composed of an acrylic resin material that includes one or more antibacterial substances, such as titanium dioxide, in order to retard, inhibit, or prevent bacterial growth. Furthermore, in some embodiments, each of the solid-surface sections may be permanently affixed to the surgical table segments via, for example, an epoxy resin or by traditional joining components such as screws, nuts and bolts. In some embodiments, some or all of the solid-surface sections may be removably attached to a corresponding surgical table segment by, for example, hook and loop fasteners such as Velcro™ fasteners and the like. The solid-surface sections can be removed, for example, if and when maintenance and/or replacement become necessary. In some embodiments, each of the solid-surface sections additionally comprises a wiring harness embedded in one or more side portions for providing power and data connections to the warming pads, which will be explained below.

In some embodiments, the warming pad layer comprises a plurality of warming pads that are configured and/or sized to conform to and mate with the plurality of solid-surface sections. For example, the warming pad layer may comprise a head warming pad, a shoulder warming pad, a chest warming pad, an abdomen warming pad, a right leg warming pad and a left leg warming pad. Each of the warming pads may be separate from each other and configured to be removably affixed to a corresponding solid-surface section. In some embodiments, each warming pad section can be separately controlled to warm to a temperature in the range of about ninety-eight degrees Fahrenheit (92° F.) to 106° F., and also may be controlled so that several or all of the warming pads are at the same temperature. Also, in some embodiments, each of the warming pads may be removably attached to a corresponding solid-surface section, for example, by mechanical latches, by a magnetic capture system, by hook and loop fasteners such as Velcro™ fasteners and the like, such that one or more power and data contacts of each warming pad is operably connected to a corresponding power and data contact of a solid-surface section.

In some embodiments, the warming pads are operably connected to (e.g., mated with) corresponding non-porous solid-surface sections, and the solid-surface sections have been semi-permanently attached to the surgical operating table segments. In some embodiments, a physical support structure for moving the surgical table segments and thus the warming pad system configuration is utilized to move and/or position each of the warming pads for patient comfort and support for undergoing a surgical procedure. Such a physical support structure may be a conventional support system used with operating tables or other patient beds that the patient warming system attaches to.

Patient warming pads comprise a plurality of layers. In some embodiments, the warming pad comprises a relatively thick thermal insulator foam layer, a heating element layer, a first electronic insulation layer, an isothermal layer, a second electronic insulation layer and a waterproof cover. In some embodiments, a disposable cover layer is also used, and this cover layer may be in the form of an envelope (e.g., similar to a pillowcase) that wraps around or encases the entire warming pad section, but permits power, data and/or latching connections to be made. The cover layer may be made of a surgical fabric, for example, of a type that is used in surgical gowns and drapes which are intended to protect both the patient and surgical team. Such a fabric may be a woven or non-woven, waterproof fabric, and may be a cotton or a cotton blend (e.g., a 65% polyester and 35% cotton blend). The cover layer is capable of transferring heat to the skin of a patient lying on top of (and thus contacting) the waterproof cover layer, such that heat passes through the disposable cover layer on the warming pad to the patient's body part. In some embodiments, the cover layer may be configured for easy removal and disposal after a surgical procedure. In some embodiments, the cover layer may be capable of reuse after being washed and/or sterilized.

The isothermal layer is characterized by having the capability of maintaining a uniform temperature across its entire surface area, which acts to prevent localized burning of a patient's skin. For example, if a patient's skin temperature rises in the middle of a warming pad, the isothermal layer will act to draw heat away or conduct heat away from that area to maintain a uniform, constant temperature across its surface area, which prevents a "hot spot" from forming. Heat is provided by the heating element layer, and the isothermal layer maintains a virtually fixed temperature under closed-loop feedback control. In some embodiments, a plurality of thermal sensors are positioned within the warming pad adjacent to or near the isothermal layer. In certain embodiments, one thermal sensor is positioned in the approximate middle or center of the isothermal layer, and thermal sensors are also positioned in each of four outside sections or corners of the warming pad to provide heat measurements of the surface of the isothermal layer in those positions. Another thermal sensor may be positioned in the approximate middle of, and adjacent to, the isothermal layer within the warming pad. These thermal sensors are operable to provide data concerning the isothermal layer temperatures within the warming pad to ensure that the temperature distribution is uniform across the surface area of the isothermal layer, and thus to ensure that "hot spots" do not form on the waterproof cover layer by limiting transverse thermal gradients. In certain embodiments, the temperatures from each of the thermal sensors are compared to each other to ensure that they are within an acceptable range of similarity (e.g., each sensor must be within 1° F. of another sensor). If the sensors differ by more than an acceptable amount, then a warning message may be provided to an operator to either decrease the temperature to that warming pad, or to replace that warming pad because it is defective in some way.

Preventing such hot spots protects against localized burns on the skin of a patient. Thus, the temperature sensors or thermal sensors provide information to ensure that the isothermal layer has not been compromised in some manner (such as being torn, punctured or otherwise damaged) so that an even or uniform heat distribution is being maintained to the entire surface of the warming pad (e.g., via the waterproof cover and/or the disposable cover). Such operation prevents hot spots from forming against the patient's skin, which results in keeping the patient safe from localized burns.

In some embodiments, the thickness of a warming pad may vary from approximately two to twelve inches, wherein the thickest layer may be the thermal insulator foam layer. The insulating foam layer provides cushioning support and thus comfort to a body part of a patient who may be reclining thereon during a surgical procedure. The thermal insulator foam layer is also heat resistant and may, in some embodiments, prevent heat loss downwards (towards the surgical table) and may reflect or direct heat upwards (in the direction of the waterproof cover layer). In some embodiments, the heating element layer is relatively thin, and the heating element may be composed of, for example, a medical grade stainless steel mesh material or an aluminum material. The heating element layer can be made of other resistive heat structures, such as a copper mesh material, or a carbon fiber cloth, or a thin foil or the like. Such a heating element layer is operable to efficiently produce heat over its entire surface area when power is supplied to one or more connector elements.

In some embodiments, the isothermal layer is sandwiched between two relatively thin electrical insulation layers. These insulation layers may be made of an acetate, fiberglass or a composite material, for example, that does not conduct electricity but that does conduct heat, and each of these layers may be relatively thin (on the order of about one-eighth of an inch or about three millimeters thick). Lastly, the flexible waterproof cover layer may be positioned above the electrical insulation layer (e.g., between a patient and the insulation layer), and may be composed of a tough, cutresistant and/or tear resistant, thin material that can repel fluids and other detritus that may contact it during a surgical procedure. The flexible waterproof layer may be made out of a durable rubberized or plastics material or vinyl material, for example, that conducts heat, is resistant to abrasions, and that can be cleaned and/or sanitized easily.

In some embodiments, the heating element layer is made of a carbon fiber woven fabric (e.g., a carbon fiber mesh material) and the isothermal layer is made of a multilayer thermally conductive carbon fiber material. Such materials will not interfere with the X-Rays generated by imaging devices such as an X-Ray machine or a CT scanner. Thus, any of such imaging devices can be utilized while a patient is lying on the warming pad system to obtain clear images of a patients organs, bones and/or tissues near or in the surgical site, for example. However, such carbon fiber mesh materials are not as thermally conductive as other material choices and therefore the isothermal layer is a bit less efficient.

The insulating foam layer provides cushioning support and thus comfort to a body part of a patient who may be reclining thereon during a surgical procedure. The thermal insulator foam layer is also heat resistant and may, in some embodiments, restricts downwards heat flow while reflecting or directing heat upwards in the direction of the waterproof cover layer. The heating element layer and isothermal layer are made of a carbon fiber material. The insulation layers may be made of an acetate, fiberglass or a composite material, for example, that does not conduct electricity, and each of these layers is relatively thin (on the order of one-eighth inch thick). Lastly, a tough, durable and flexible waterproof cover layer above the electrical insulation layer resists cuts and punctures, and is configured to repel fluids and other detritus that may contact it during a surgical procedure. As also mentioned above, the flexible waterproof layer may be made out of a durable rubberized, an engineered plastic flexible sheet (e.g., a vinyl sheet) that conducts heat and is resistant to abrasions.

Figure 1D:
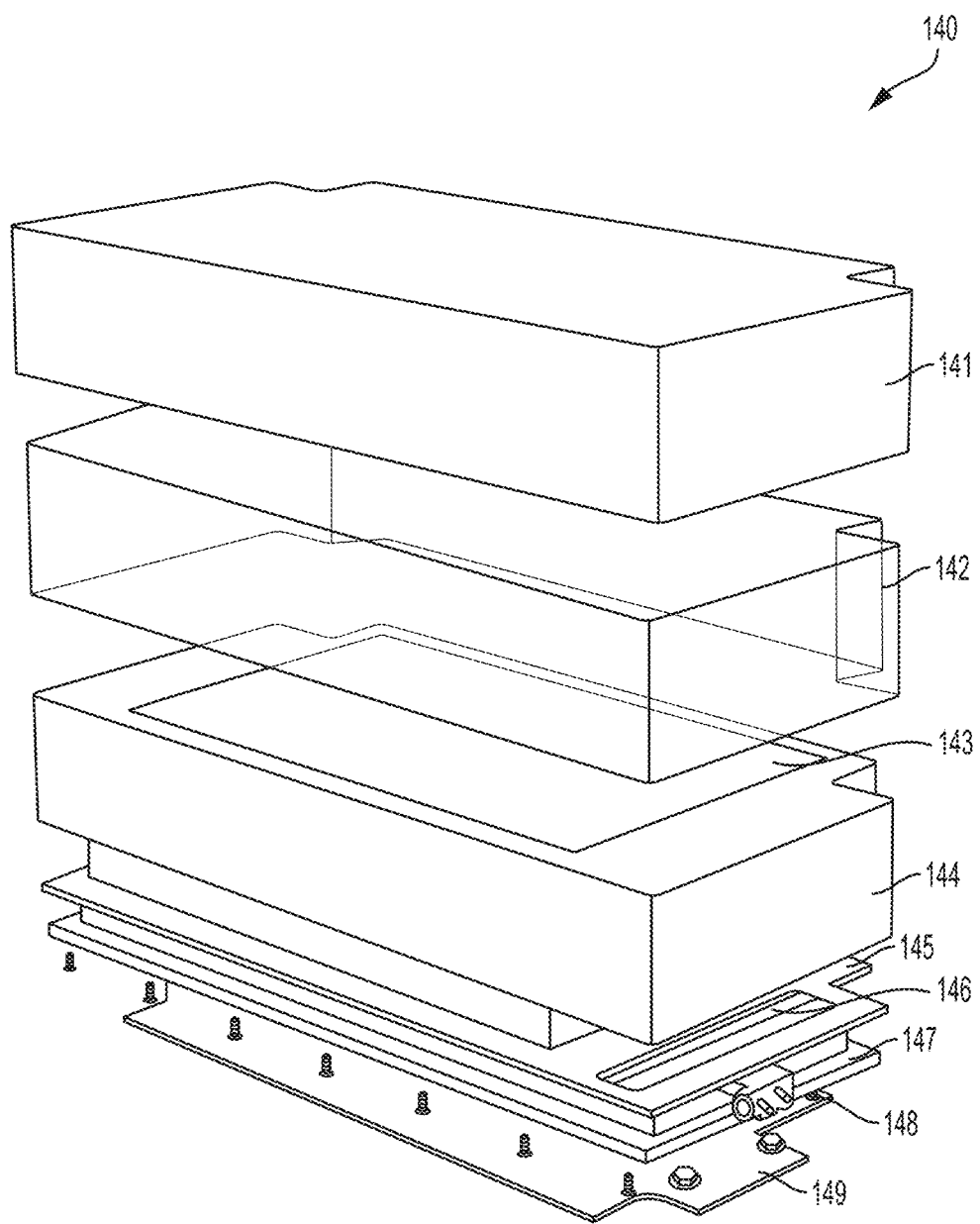
FIG. 1D shows an exploded view of a patient warming pad system, according to an illustrative embodiment of the invention.

An illustrative embodiment of a patient warming pad system with a single pad is shown in FIG. 1D. Warming pad system 140 comprises bedding cover 141, expanded mesh 142, warming pad 143, foam layer 144, rigid tray 145, electronic components 146, retaining strap 147, and ratchet fastener 148 attached to operating table plate 149. Bedding cover 141 provides a protective barrier between the system and a patient. Expanded mesh 142 is an isothermal layer. Warming pad 143 provides heat for patient warming. Foam layer 144 insulates and isolated warming pad 143. Rigid tray 145 acts as a rigid support section for warming pad 143 and other supporting layers. Electronic components 146 provide power and sensor connections and control to warming pad system 140 and may be externally connected to a floor equipment, table equipment, or other utility providing interface in order to provide appropriate utilities to patient warming pad system 140. Retaining strap 147 and ratchet fastener 148 are used to affix rigid tray 145 such that warming pad 143 and other associated components are temporarily affixed to operating table plate 149.

In some embodiments, the warming pad system is powered by a low-voltage system, such as a 24 volt system. A low-voltage may be defined as a voltage that is sufficient to power the heating element layer so as to provide a non-negligible warming of the surface layer of the warming pad, but no higher than a voltage that would be considered unsafe if a patient were exposed to such a voltage.

In certain embodiments, a patient warming pad system or patient warming pad comprises a cooling layer. An externally cooled liquid tubing pattern may be located adjacent to or below the heating element layer to permit bidirectional heating/cooling control. Such a cooling layer would be utilized when the heating layer is turned off (or not being used), to cool down a body part of a patient lying on the warming pad.

In some embodiments, utilities needed for the patient warming system are connected to both the solid surface sections and warming pad sections. For illustrative purposes only, the following description refers to solid sections and warming pads for the abdominal area; a solid section and corresponding warming pad for any area of the patient could be equivalently used. A bottom portion of the abdomen warming pad includes a latching, power and data contacts area positioned near an outside edge. The area includes latching or connector apparatus, power input/output connections, and data input/output connectors. Similarly, a top surface portion of the abdomen solid-surface section includes a latching, power and data contacts area near an outside edge. The area includes latching or connector apparatus, power input/output connections, and data input/output connectors. Consequently, when the abdomen warming pad and the corresponding portion of an abdomen solid-surface section are joined together, the latching apparatus of the warming pad connect to the latching apparatus of the solid-surface section in a removable manner (e.g., the connection may be made by mechanical latches, by magnetic capture, or by utilizing a hook and loop fastener, such as a Velcro™ fastener). In addition, when the abdomen warming pad and the corresponding portion of an abdomen solid-surface section are connected together, the power input/output connections are mated with the power input/output connections, and the data input/output connectors mate with the data input/output connectors. In some embodiments, the latching, power and data contacts areas are located on an outside edge of each of the warming pads and the solid-surface sections so as to facilitate their alignment and connection. In addition, such positioning may also serve to provide easy access to power and input/output lines that can be provided from an embedded system in the surgical table. However, in some other embodiments, another power and/or data source, such as a cart, may be positioned at, near or below the surgical table and provide the required data and power connections.

In some embodiments, the latching, power and data contacts area has a top surface portion and a side surface portion, and the latching, power and data contacts area has a top surface portion and a side surface portion. The top surface portions are configured for connecting to corresponding latching, power and data contact areas of a warming pad. In some embodiments, the side surface portions may be configured for accepting power and data inputs supplied from the surgical table or some other power and/or data supply device in the operating room. In some embodiments, power and data connectors on the underside of the solid-surface panels are configured for mating with power and data connectors of the surgical table sections. In addition, one or more internal wiring harnesses, which may be imbedded in one or more of the solid-surface panels and/or the surgical table sections, may be utilized to make connections between, for example, power input terminals and power output terminals, and between data input terminals and data output terminals. In certain embodiments power, data and wiring harness components are located along an edge portion of a warming pad, solid-surface section and surgical table segment to ensure that a minimal internal wiring shadow will be cast when an X-Ray is taken of a body part of a patient.

In some embodiments, a temperature sensor comprises a plug (e.g., a standard phono plug-type connector or "Molex" style connector), a data lead and a sensor (e.g., a pressed disc ceramic sensor, or a thermistor). Such temperature probes may be disposable, single-use products or may be reusable. For example, the temperature sensor may be a reusable skin surface probe sold by various companies, such as YSI Incorporated, which provides continuous patient monitoring of skin surface temperatures. In some embodiments, the plug is configured for insertion into the socket located in the side wall portion of the solid-surface section, and the sensor is designed to be attached to a skin area of the patient that generally corresponds to the solid-surface section to which it is connected. For example, during a surgical procedure involving a patient's shoulder area, the shoulder warming pad may be selected to provide 99° F. to the patient, and the temperature sensor would be plugged into the socket with the sensor connected to the patient's skin in the shoulder area. The sensor would then transmit real-time temperature data to a control circuit, which also collects temperature data from the thermal sensors within the shoulder warming pad which are operable to sense temperatures associated with the isothermal layer within the shoulder warming pad. Thus, a user, such as an a anesthesiologist, would be provided with real-time feedback concerning the skin temperature of the patient in relation to the temperature of the warming pad and could use the measurements to make adjustments accordingly.

In some embodiments the warming pad system is powered by a low-voltage system, such as a 24 Volt system. The power supply, and thus the warming pads may be regulated via a software graphical user interface (GUI) control system that allows manual control as well as the automatic regulation of temperature. Snapshots of an illustrative embodiment of a GUI are shown in FIGS. 1E-1J. In some embodiments, the GUI control system is configured to run on a wireless computing device (e.g., a laptop computer, a tablet computer, a personal digital assistant, or a mobile phone). During use of the patient warming system, current flows through the heating element layer within one or more warming pads (between negative and positive contacts) resulting in an increase in temperature which is directed upwards toward the waterproof cover layer of each warming pad. In some embodiments, a control circuit that includes at least one microprocessor controls the power and data outputs to the warming pad system, and receives temperature data from the various temperature sensors and/or thermistors of the system. For example, the control circuit may receive instructions from a user to maintain a chest warming pad temperature of 99° F., and thus when the chest temperature sensor transmits data to the control circuit that the temperature in the chest area of the patient has decreased below that predetermined limit, the control circuit may automatically increase the current to the chest warming pad to increase the temperature.

The GUI may be configured for use on a display screen of a wireless computing device. In some embodiments, skin temperature sensors are applied directly to an arbitrary location on the patient's skin that roughly corresponds to each warming pad location (which corresponds to a particular body part of the patient) so that the patient's skin temperature in each such region (such as the head, shoulders, chest, abdomen and legs) can be monitored before, during and/or after a surgical procedure. Data from these temperature sensors can be interpreted by control circuitry to provide a graphical indication to a user in real-time on a display screen so that changes can automatically or manually be made, for example, during a surgical procedure.

When initializing the GUI, a user may be prompted to make selections regarding the configuration of the system that will be controlled using the GUI. FIG. 1F shows a first screen of a GUI for selecting the number and layout of pads to be used. Different configurations that may be used comprise a whole body configuration 171 and a torso configuration 170. Other configurations may be designed for particular types of surgical procedures or treatment protocols. Once a configuration is selected, the system may check that all pads used in the selected configuration are connected. FIG. 1G shows a GUI after a "6-Pad Normal Configuration" is selected wherein pad B is disconnected. The pad B icon 172 color changed to orange and an error message 173 alerts a user to the situation with options to proceed regardless or change the configuration. FIG. 1H shows the GUI of FIG. 1G after the pad has been (re)connected. The pad B icon 172 color changed back to blue and a new "status OK" message 174 appeared. Additionally, the system may be configurable to the size or particular anatomy of a patient. FIG. 1I shows a GUI after the configuration has been selected. The selected configuration 176 is graphically displayed and options to choose between youth 177, adult female 178, and adult male 179 versions of the selected configuration are displayed for selection.

Figure 1E:
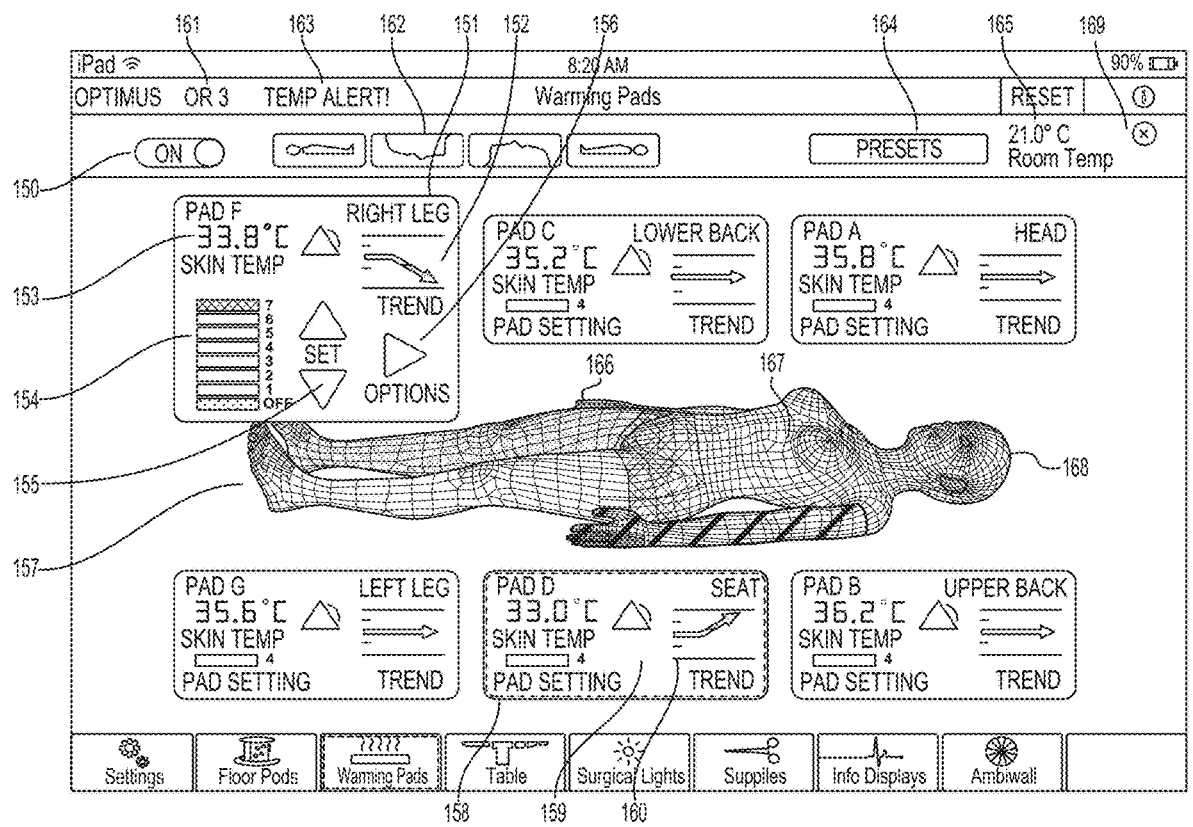
FIG. 1E shows an exemplary graphical user interface for controlling a warming pad system, wherein the identifying pad letters are consistent with the system shown in FIG. 1B, according to an illustrative embodiment of the invention.
Figure 1F:
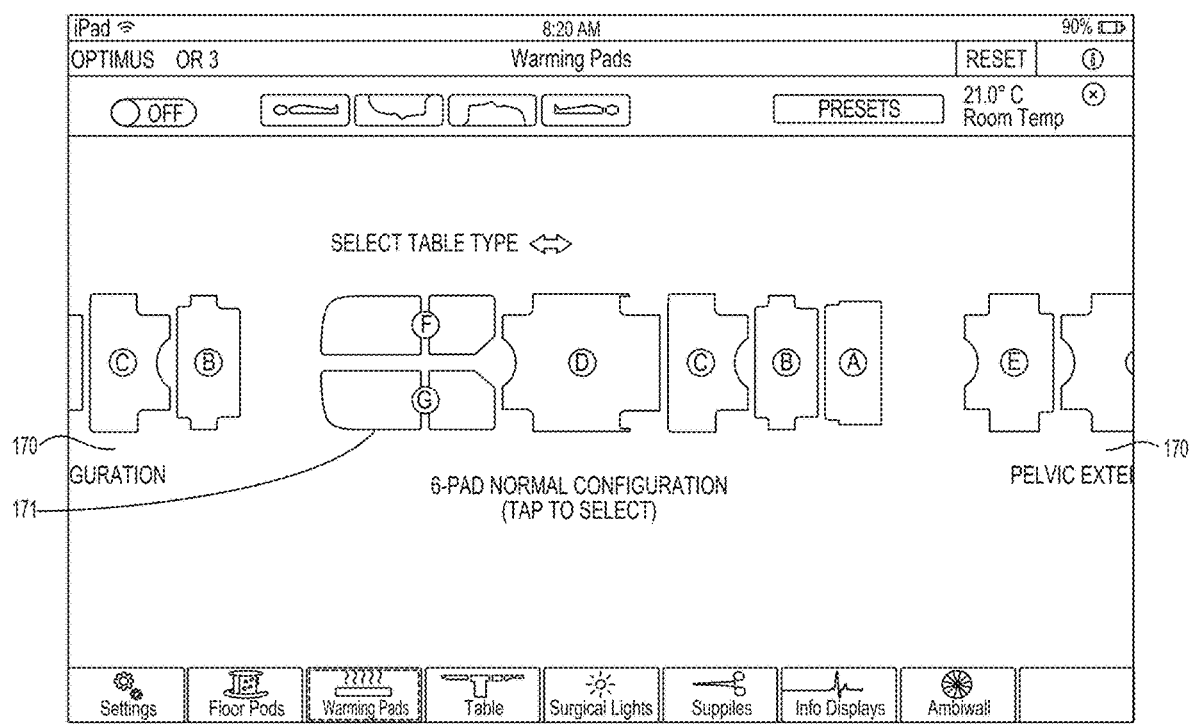
FIG. 1F shows a graphical user interface when selecting a patient warming pad system configuration, according to an illustrative embodiment of the invention.
Figure 1G:
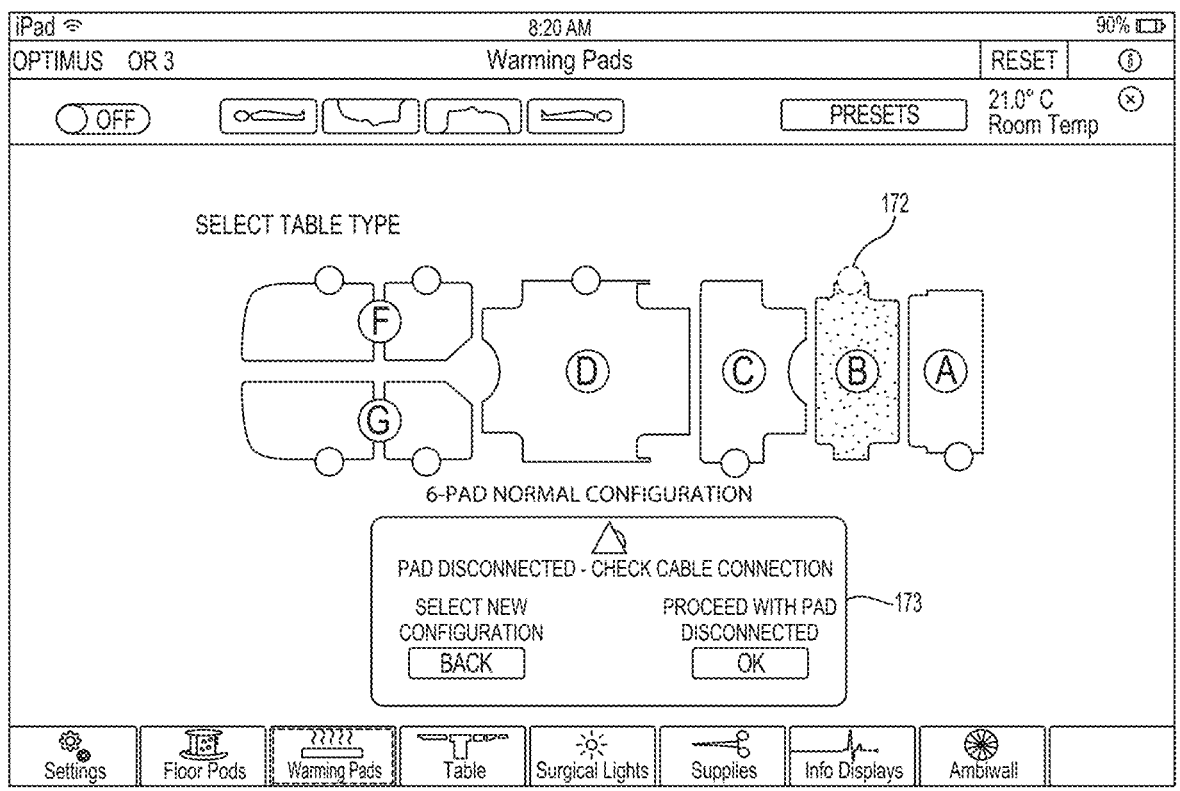
FIG. 1G shows a warning on the graphical user interface when one of the warming pads in the system is not connected, according to an illustrative embodiment of the invention.
Figure 1H:
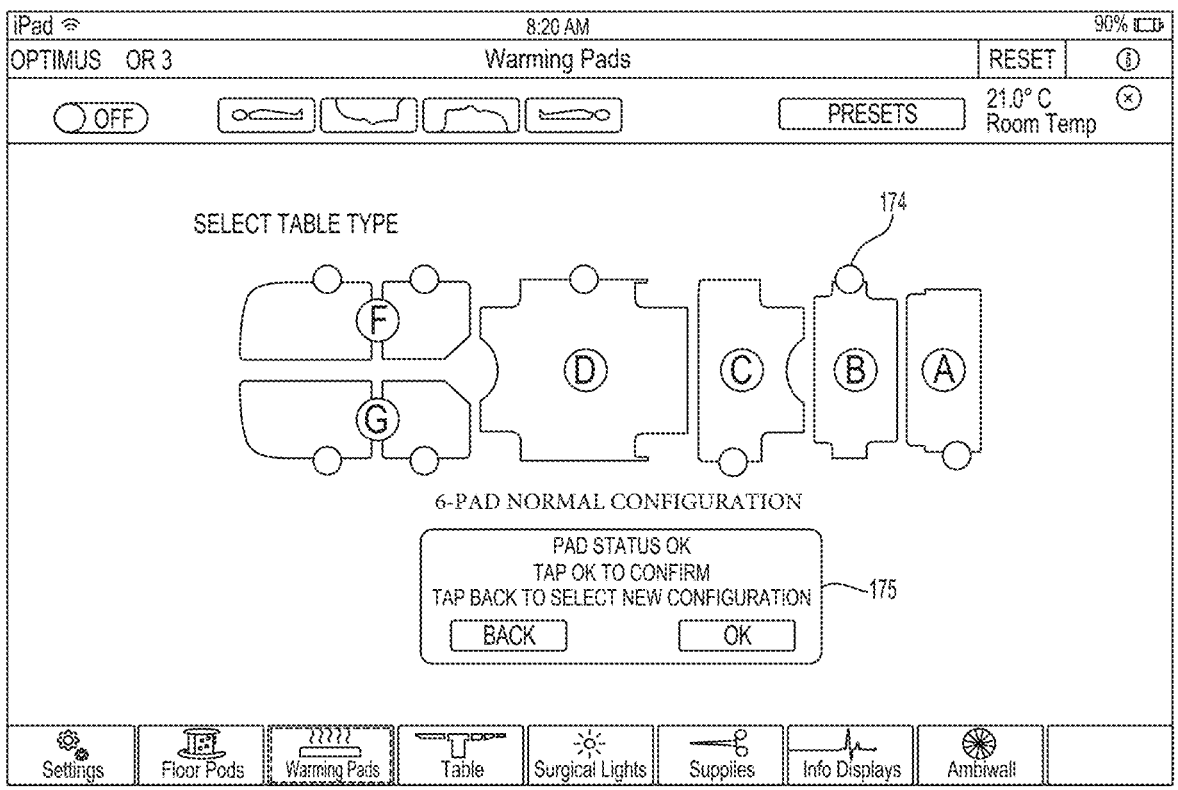
FIG. 1H shows a confirmation on the graphical user interface that is shown when a previously disconnected warming pad is properly connected, according to an illustrative embodiment of the invention.
Figure 1I:
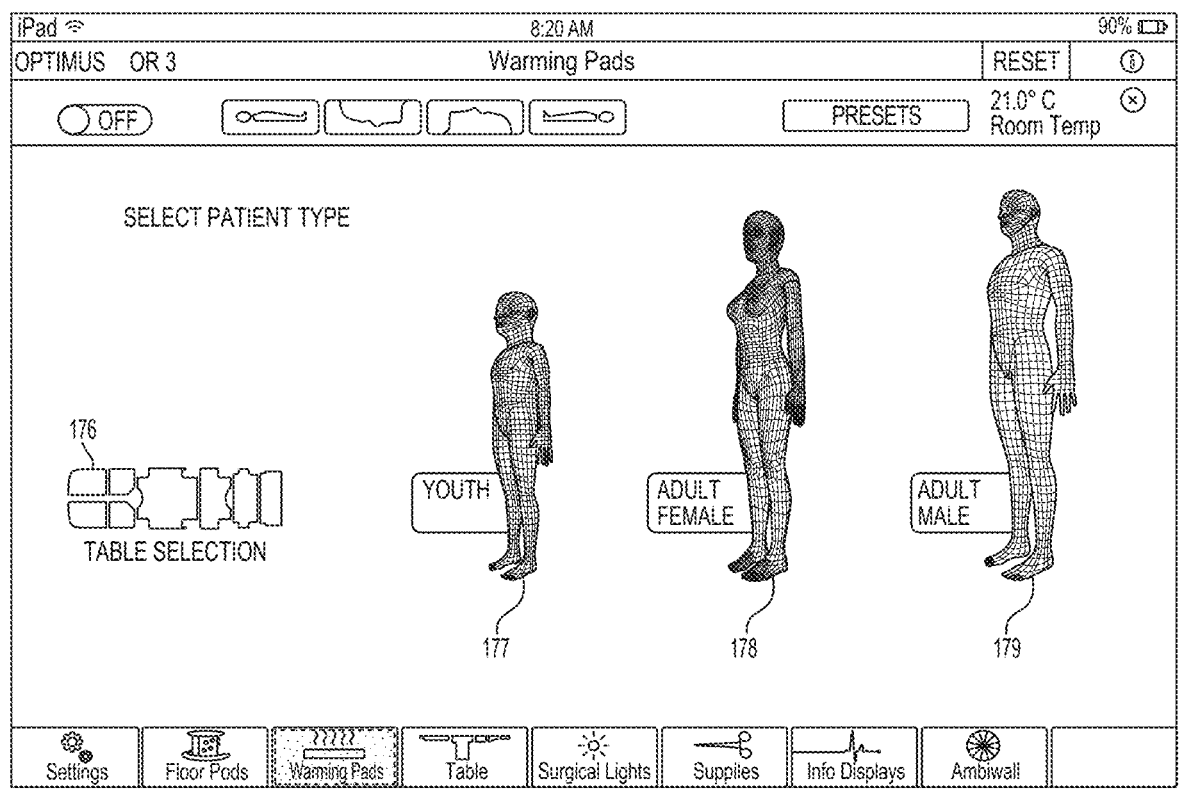
FIG. 1I shows a graphical user interface when selecting the patient type for a patient, according to an illustrative embodiment of the invention.

After initialization, the patient warming pad system GUI enters a control screen, as shown in FIG. 1E. The patient warming pad system GUI shown in FIG. 1E shows a wireframe patient graphic 157 that includes color variations that help a user to determine which regions of the patients' skin are warmer or cooler than others. For example, a red area 167 may indicate a temperature above the limit set by the user, a blue area 166 may indicate a temperature below the limit set by the user, and a green area 168 may indicate that the temperature is within the limits set by the user and/or within preset limits. The GUI also includes graphical displays of each of the warming pad sections comprising a temperature trend indicator portion and a skin temperature reading. For example, the seat warming pad display 158 shows an up-trending temperature trend indicator 160 and a skin temperature reading of 38.0° C. A selected panel (e.g., selected by using a computer cursor, or by touching in the screen of a touchscreen device) shows an expanded set of controls appears in the warming pad display. For example, the selected graphical display 151 permits the user to make adjustments via temperature control arrows 155 and an options button 156 as well as shows a graphical indication of the temperature setting of the pad 154. Based on the down-trending temperature trend indicator 152 and low skin temperature reading 153 shown in the GUI of FIG. 1E, a user may utilize the temperature adjustment arrows 155 to increase the set temperature of the right leg warming pad in order to warm the patient in this area.

When the skin temperature readout is above or below the set temperature, an alert icon appears. The alert icon may be a bright color, flashing on and off, and/or include one or more other graphical devices to attract the attention of the user to the temperature situation. Warning indications could additionally take the form of numerical temperature readouts, textual messages, graphic icons, color-coded icons or messages, and audible tones to alert a user of one or more skin temperature readings that are too high and/or too low, based on one or more set temperature. An alert (audible or visual or both) may also be provided that indicates when the target temperature is reached. A textual alert may also be provided that may be prominently displayed on the display screen, or otherwise made conspicuous, and more generally may be shown in other screens that are being utilized to control other operating room components, so that a user will notice and take appropriate action. In the present illustrative embodiment, a first indicator 159 shows that the skin temperature reading at the seat pad is outside the set range and a second global indicator 163 shows that one or more of the skin temperature readings is outside of its set range.

The GUI of FIG. 1E additionally displays general information relevant to the patient warming system such as the setting of the patient warming system being currently controlled 161, a current temperature of the setting 165, an on/off toggle 150, orientation buttons 162, a close button 169, and a presets button 164. Orientation buttons 162 permit the user to define how the patient is oriented on the warming pad system, for example, whether the patient is lying face-down towards the warming pads or is lying face-up (with his or her back in contact with the warming pads). The presets button 164 allows the user to access and apply previously saved temperature settings and alarm limits to the current GUI, and in some embodiments allows current settings to be saved to a database for future use. The close button 169 allows the user to close the GUI without turning the warming pads off or altering their settings, which, in some embodiments, allows access to controls for other operating room components. A user can turn the warming pad system ON and OFF via the on/off toggle 150. A power switch may also be provided so that a user can switch off his or her handheld device and/or close or terminate the GUI. An "Options" menu (not shown) may also be provided that permits the user to, for example, choose a preset to control a pad warming pattern over a set time-span, to apply a uniform temperature setting to all of the warming pads, and/or to choose Fahrenheit or Celsius temperature scales. In certain embodiments, additional screens or pop-up menus of the GUI may be provided to save settings as preset for future use, to search and select presets to be used for a current surgery, to control a time-span view of a temperature history graph for one or more warming pads, and/or to save current temperature history graph data to a patient records storage location (e.g., a database).

In certain embodiments, the thermal inertia (e.g., thermal time constant) is sufficiently long (e.g., on the order of many seconds) such that an on/off control is acceptable to turn on and to turn off the heating element. In particular, it is unnecessary to utilize proportional control circuitry in order to lower the temperature or to increase the temperature, so a simple on/off control can be used with a low driver temperature rise and minimum electrical noise generation.

Figure 1J:
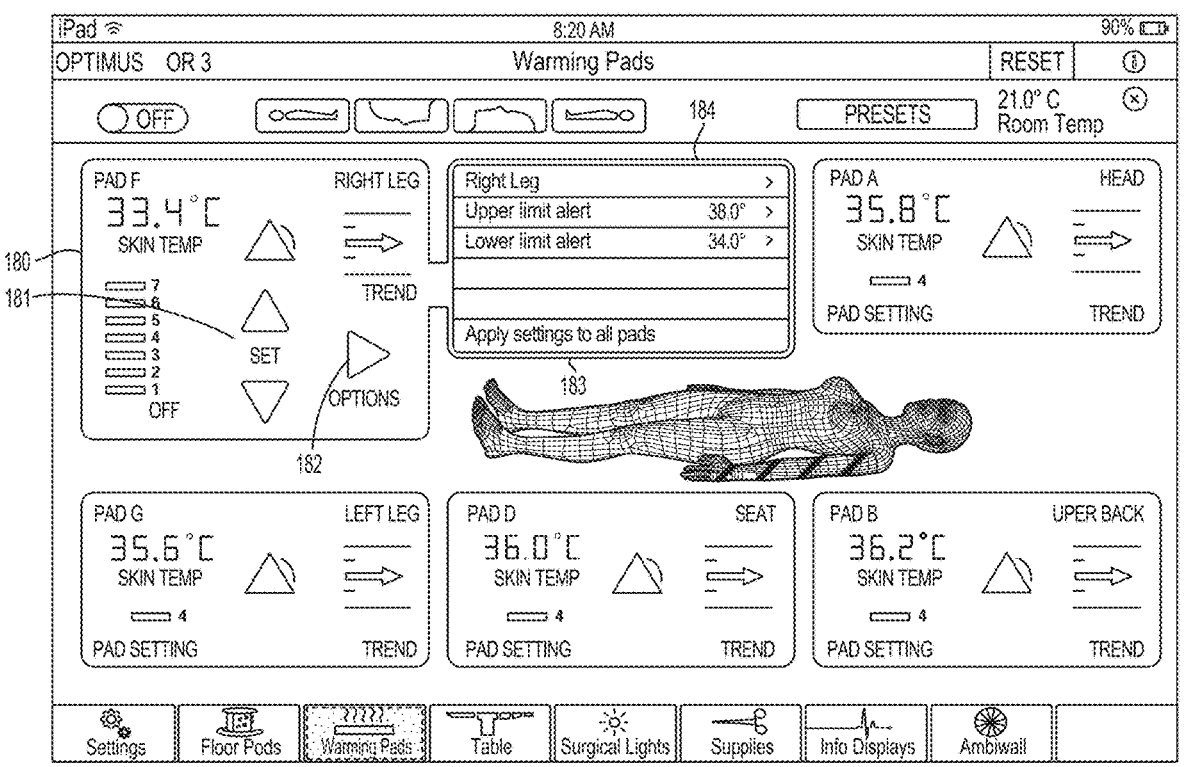
FIG. 1J shows a graphical user interface when adjusting the temperature settings of a warming pad in the system, according to an illustrative embodiment of the invention.

In certain embodiments, displays of temperature and controls for raising or lowering the temperature are provided for each individual warming pad of the warming pad system. In the GUI of FIG. 1J, when a specific warming pad display is selected, icons for controlling the set temperature 181 and options 182 for changing temperature are provided. An option to apply a uniform temperature to all of the warming pads simultaneously can be included, and options to change a Fahrenheit readout to a Celsius scale readout (and vice-versa) may also be provided. In FIG. 1J, the user applies presets for set temperatures from the pop-up display 184 that controls setting of a desired target temperature by selecting "Right Leg" from the pop-up display, to in effect control how much power is applied to any particular warming pad. The pop-up display 184 additionally permits the user to set upper and lower temperature limits that will trigger alarms.

The user may select button 183 to apply the current settings of the selected pad to all pads currently being controlled with the GUI.

In certain embodiments, when complying with instructions from medical staff, or according to set-up procedures for a scheduled surgery, the user may do any one or more of the following:

Turn the warming pads on or off;
Set any number of individual pads to a specific temperature;
Set the upper and lower temperature limits that will trigger alarms;
Choose a preset to control pad temperature upper and lower limits;
Choose a preset to control pad warming over a set time-span;
Apply a uniform temp setting to all pads;
Respond to an alert;
Respond to establishment of proper/improper electrical and data connections;
Use a secondary screen or pop-up menu to search and select presets to be used for current surgery; and
Use a secondary screen to view a temperature history graph, control time-span of the view, and/or save current temperature history graph to patient records.

In some embodiments, as explained above, the warming pads comprise a secondary high-temperature monitor to provide a warning if any or all of the warming pads has reached a critically high temperature, or if the skin temperature (monitored by a skin thermistor) has reached a high temperature. The controller includes software that is capable of lowering and/or shutting down power to any of the warming pads that have gone beyond a predetermined temperature threshold (or if the skin temperature of the patient has exceeded the temperature threshold for that warming pad). In addition, diagnostic functions may be provided that include providing an indication that a particular warming pad has established the proper electrical and data connections. Warming pad performance and fault detection history may also be saved and accessed. Additional functionality may also be provided, such as recording, storing and graphically displaying patient and pad temperature trends over time. In some embodiments, each warming pad includes a unique identifier, such as an internal serial number, that may be utilized, for example, to track the heating history of that particular warming pad.

Integrated Air and Lighting Plenum and Surgical Lighting

In most healthcare environments, air flow and lighting in a room are handled as two separate systems. Frequently, air outlets are mounted in the ceiling as are various lighting fixtures. In healthcare environments, the quality of air flow and lighting provided to a room can have profound effect on the ability of medical staff to properly perform their duties. For example, in an operating room, highly laminar airflow around the operating theater is highly desirable to maintain the sterility of the area immediately surrounding a patient. Additionally, many surgical lighting systems exist to provide lighting for operations that is highly adjustable to the needs of a patient (e.g., to the location or orientation of the patient). These systems are mounted in into the ceiling using booms or articulated arms that offer various degrees of manipulability. However, both of these conventional systems suffer from certain flaws of engineering that result in a suboptimal experience for medical staff and increased risks to the patient.

Certain interior environments, such as clean rooms and hospital like operating rooms, radiology rooms, and dental suites, require unusually clean air for the protection of the work that takes place in them. Specifically, many infections in patients are contracted during surgical procedures in an operating room environment. The surgeons, nurses and other personnel may take some precautionary steps but they are typically not enough to keep bacteria and other organisms away from the open wounds.

Such rooms may also have disparate heating or cooling needs at different points in the room. For instance, electronic equipment may produce excess heat, therefore requiring that cooled air be concentrated in its vicinity. Surgeons may also find it prudent to have available additional heated or cooled air in the immediate vicinity of an operating table, to hold a patient at a stable temperature or dissipate the excess heat created by bright lamps or a team of doctors and nurses surrounding the patient. However, the needs of a given room can change over time, as new technology replaces what was originally installed or the room is converted to uses or configurations other than the original. Additionally, when multiple parties provide equipment for these spaces, there is significant coordination required during the design and construction phase to avoid conflicts and interferences in product and schedule. Ensuring an adequate amount of airflow that can be adjusted given the dynamism of the operating room is a fundamental concern for the surgical staff.

Several surgical apparatuses and methods have been developed in the past using different mechanisms to provide air flow in the vicinity of an area to be protected. These units were originally designed to provide layered airflow in an effort to reduce turbulence around the patient and surgical staff. However, with the ever increasing number of ceiling mounted pendants introduced into the area of surgery, true laminar flow has proven to be nearly impossible to achieve due to turbulence introduced by each new pendant mounted modality. Typical laminar flow systems are a source of increased operating room noise, surgical site infections (especially the plastic "flow skirt" hanging around many laminar flow units), and increased turbulence at the rectangular corners of airflow units. None of them, however, includes an apparatus that maintains laminar airflow away from the protected area to minimize infection probabilities by aerobic pathogens around the area of surgery. Another issue is that no laminar flow system covers the entire area of surgical interest, including the entire patient and operating table (approximately 7 feet in length), the surgical scrub staff, and surgical instrument trays.

In part, this is due to the presence of significant overhead-supported equipment such as light and equipment booms and automated material handling systems. Typically, such equipment is hung from the building structure and descends through the ceiling in order to preserve valuable floor space. However, this arrangement is subject to the similar problems as hard-wired ventilation: it is expensive, requires a custom installation during building construction, and may limit the possible room configurations and final functionality of the system based on the nature of the underlying building frame and various booms and/or articulated arms associated with the lights. Thus, the aforementioned lighting systems are not conducive to integration with an airflow system.

These lighting systems further require extreme care to be taken in their adjustment, not only to ensure that adequate light remains focused on the patient, but also to ensure that medical errors are not made due to the movement of the light. Risks associated with such infrastructure comprise risks to sterility of the patient and room; risks of surgical errors due to untimely and uncoordinated movement of a light during a procedure; and risks of complications due to the increased amount of time spent adjusting lights to properly illuminate the intended location of a procedure. Additionally, such surgical lights necessitate long operational downtimes in the event that one of the lights malfunctions due to their hardwired installation into elaborate support structures such as booms or articulated arms. Although unlikely, the occurrence of a malfunction during a surgical procedure could additionally cause a range of complications for the patient as the surgical staff is required to work around the malfunction. Moreover, for procedures or treatments where a patient is conscious, harsh lighting conditions may prohibit the patient from entering a relaxed state, which has been shown to increase the likelihood of complications.

In general, a surgical operation requires lighting systems having specific light-technological properties. For example, shadows must be eliminated or else they will interfere with a surgeon's ability to properly visualize the surgical site. During a surgical operation, a doctor usually needs to expand the light field to get a better vision of the target area. Conventional surgical lights are cumbersome and arcane, and some represent a safety hazard to the surgical staff. In some cases, the surgical lights are mounted on dollies so as to be movable about the surgical field in an attempt to reduce the risks associated with conventional in-ceiling mounted lighting, but such surgical lights are difficult to maneuver, compete for precious space needed for other surgical equipment, and poorly illuminate the surgical field.

Surgical operations involving deep tissue wounds present a particular challenge for surgical staff. Deep tissue wounds often occupy small areas of the body and lie between or underneath other layers and/or organs, requiring a lighting system simultaneously capable of intensity (to prevent areas of darkness/shadows) and accuracy (bright and intense lights can wash out visual contrast). Color temperature is a key factor in this equation. For example, while warm white lights allow you to look at skin color, they do not display surgical detail and physiology as well as cool white lights do.

Presently, surgical lighting does not possess the versatility to accommodate this wide range of lighting needs. For example, as the intensity of a light beam increases, the ability to distinguish texture and color decreases as does the spot size the beam illuminates. Conversely, large spot sizes (i.e., lowered intensity) poorly illuminate the area of significance, preventing a surgeon from focusing on a particular spot for surgery, and often distort clear visualization from reflection off of the illuminated area. The ability to accurately and easily customize these variables has not been available for surgeons to more efficiently and safely perform their tasks, particularly for the complex nature of deep tissue wounds.

Figure 2A:
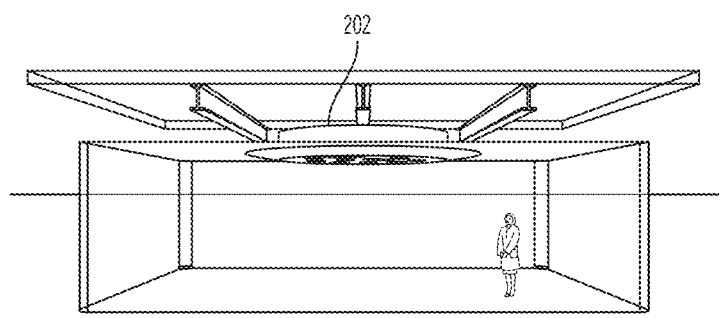
FIG. 2A shows an integrated air and lighting plenum attached to the ceiling of a healthcare setting, according to an illustrative embodiment of the invention.
Figure 2B:
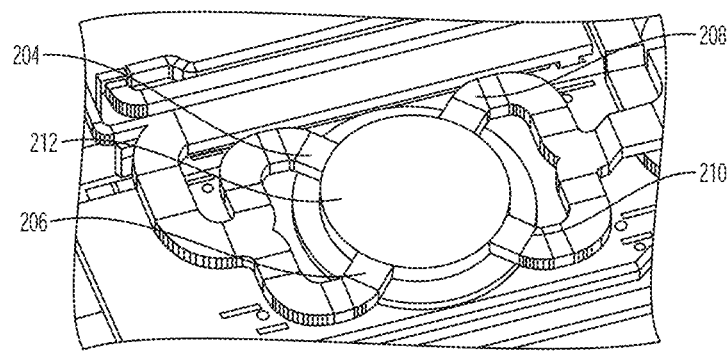
FIG. 2B shows how an integrated air and lighting plenum would attach to the duct work of a healthcare environment's HVAC system, according to an illustrative embodiment of the invention.

In certain embodiments, described herein is an integrated air and lighting plenum that is the primary directional lighting mounting apparatus and laminar flow diffuser of an HVAC system in a healthcare setting. In some embodiments, the integrated air and lighting plenum can be installed in a convenient, cost-effective, and modular manner. In certain embodiments, the integrated air and lighting plenum comprises integrated surgical lighting, general room lighting (scrub lighting), cyclic circadian lighting, video cameras, and microphones as an integrated unit that is suspended from the ceiling of a room in a healthcare environment (e.g., an operating or clean room). In some embodiments, the plenum comprises mounts for lighting fixtures, but not the lights themselves, allowing a user to install lights of their choosing. FIG. 2A schematically represents such an integrated air and lighting plenum 202 installed in the ceiling of a room. FIG. 2B shows a top view of such an integrated air and lighting plenum 212 connected to the HVAC system of the healthcare environment by four input ducts 204-210.

Figure 2C:
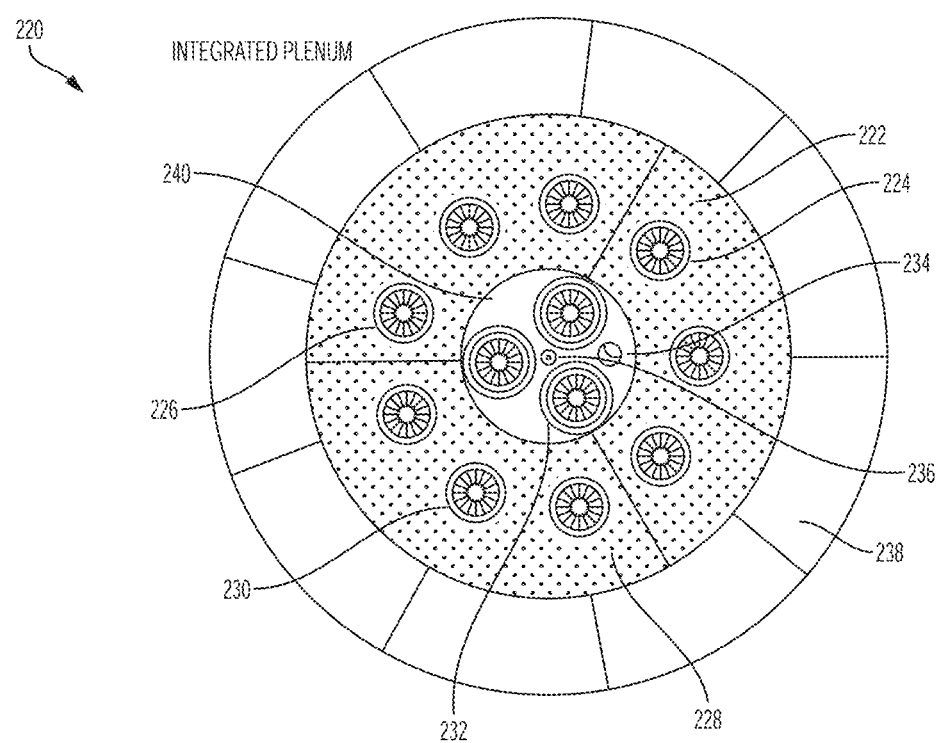
FIG. 2C shows a schematic of an integrated air and lighting plenum comprising, general illumination lighting, airflow outlets, two circular arrangements of directional lighting (e.g., surgical lighting), and two accessory cameras, according to an illustrative embodiment of the invention.

In some embodiments, the integrated air, and lighting plenum is a circular apparatus comprising three concentric units. FIG. 2C shows an exemplary embodiment of an integrated air and lighting plenum 220. A first ring-shaped unit on the periphery of the plenum can be made to include general lighting 238 for the room (e.g., scrub lighting). Such general lighting can provide sufficient, diffuse light necessary for staff to perform necessary functions. The light may be made diffuse by using translucent cover panels for the general illumination light sources. Optionally, the lighting components used for the general lighting may be chosen such that their color is adjustable. The color may be adjusted to the preference of a patient or staff member in order to provide a calming environment or improve visibility for a certain task, for example. A second ring-shaped unit located interior to the first unit comprises a plurality of surgical lights 224-228 and/or a plurality of housings for surgical lights (not shown in FIG. 2C). Such surgical lights or housings for surgical lights may be arranged in a circle having a diameter of up to 84". In order to provide laminar air flow from the ceiling to the room in which the plenum is located in accordance with HVAC requirements for healthcare environment settings, the second ring-shaped unit may comprise a plurality of airflow outlets 222. Having many surgical lights located in the arrangement allows multiple surgical lights (e.g., 224, 226, and 228) to be used in a coordinated manner (e.g., as a system) to illuminate a patient or work area while also providing redundancy as well as the ability to tailor illumination to fit particular needs (e.g., by coordinating more surgical lights (e.g., 230)). A third unit 240 located interior to the second ring-shaped unit comprises additional surgical lights 232 or housings for surgical lights (not shown in FIG. 2C) to increase the range of lighting orientations achievable by the plenum in order to satisfy the needs of staff in lighting a surgical site or work area. The surgical lights or housings for surgical lights of the third unit may be arranged in a circle having a diameter of up to 26". Additionally, such an integrated air and lighting plenum may further comprise one or more accessories such as a webcam 234, a camera 236, a microphone, sensors, or speakers, to provide additional functionality to the plenum, for example, for monitoring a room or patient or to assist in controlling the surgical lights. Optionally, surfaces of the plenum can be coated or impregnated with formulations of titanium dioxide ($TiO_2$) that inhibit the growth of bacteria under full-spectrum lighting in order to enhance sterility of the room in which the plenum is located.

Figure 2D:
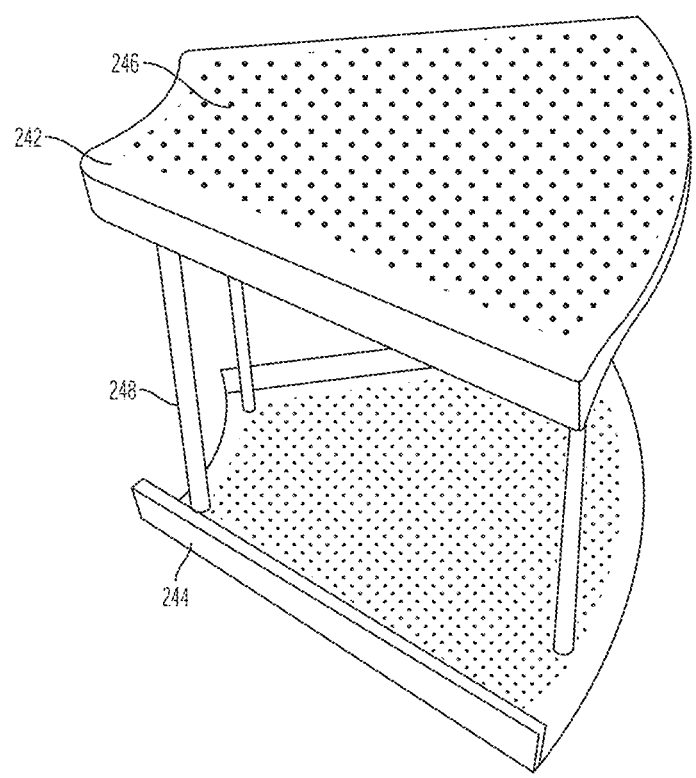
FIG. 2D shows a modular panel, comprising cylindrical airflow outlets, that forms part of an integrated air and lighting plenum, according to an illustrative embodiment of the invention.
Figure 2E:
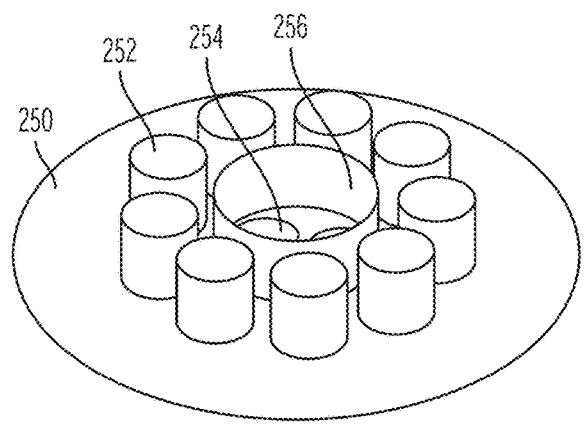
FIG. 2E shows a schematic of the housings for an arrangement of directional lighting in an integrated air and lighting plenum, according to an illustrative embodiment of the invention.
Figure 2F:
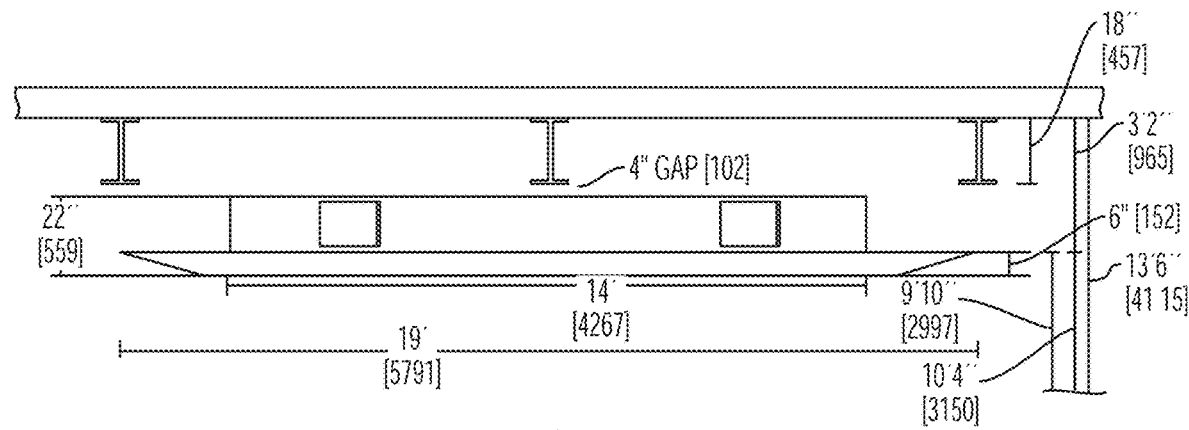
FIG. 2F shows a schematic of a side view of an integrated air and lighting plenum, according to an illustrative embodiment of the invention.

FIG. 2F shows a schematic side view of an integrated air and lighting plenum that lists the various overall dimensions of the plenum. As shown in FIG. 2F, in some embodiments the integrated air and lighting plenum is housed in an operating room of total height 13 feet 6 inches. In such operating rooms, the back side of the integrated air and lighting plenum is located about 22 inches from the ceiling, such that the front side of the integrated air and lighting plenum is 9 feet 10 inches from the floor of the operating room. The total thickness of the integrated air and lighting plenum is about 22 inches and the largest diameter of the integrated air and lighting plenum is 19 feet. The inner diameter of the integrated air and lighting plenum without the general lighting (238 of FIG. 2C) is about 14 feet, thereby covering the entire area of surgical interest, including the entire patient and operating table (approximately 7 feet in length), the surgical scrub staff, and surgical instrument trays. The thickness of the general lighting is about 6 inches and it hangs at about 3 feet 2 inches from the ceiling of the operating room.

FIG. 2E shows a schematic top view of an integrated air and lighting plenum 250 wherein the plenum comprises an outer plurality of surgical light housings 252 and an inner plurality of surgical light housings 254. The surgical light housings may provide a hermetic seal to isolate the surgical lights from the airflow of the plenum. The innermost unit of a plenum may be a modular part 256 that isolates the entire innermost unit from the airflow of the plenum.

Figure 2G:
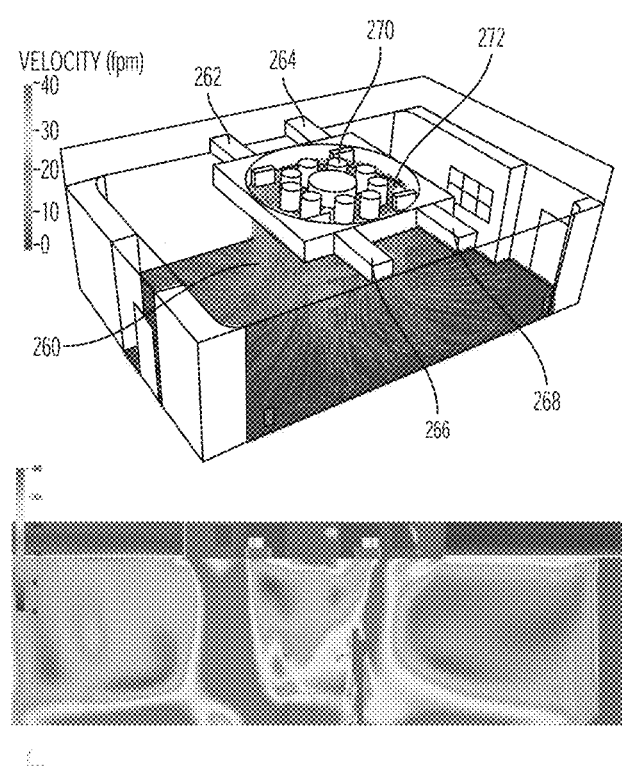
FIG. 2G shows a simulated illustration (3D and side view) of the laminar airflow around an operating theater that can be supplied by an integrated air and lighting plenum, according to an illustrative embodiment of the invention.
Figure 2H:
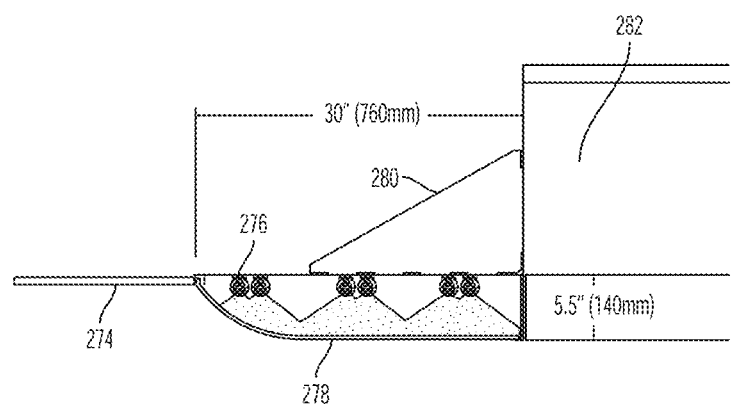
FIG. 2H shows a detail of the general illumination lighting arrangement of an integrated air and lighting plenum (e.g., 238 in FIG. 2C), according to an illustrative embodiment of the invention.

FIG. 2H shows a side view of an integrated air and lighting plenum mounted in a ceiling 274. The general illumination lighting is provided by a plurality of LEDs 276. A translucent panel 278 diffuses the light throughout the setting the integrated air and lighting plenum is installed in. One or more support fins 280 may be used to produce structural support to the plenum body 282.

In some embodiments, the airflow outlets are cylindrical outlets located in the panels of the second arrangement. The use of cylindrical airflow outlets promotes laminar airflow by reducing sharp boundaries that induce turbulence (e.g., the corners of rectangular or square outlets). FIG. 2G shows air 260 from the HVAC system ducts 262-268 forced through a plenum with cylindrical outlets 272. The air also flows around the housings that mount the surgical lights 270. By integrating outlets for airflow around or in proximity to the surgical lights and other electronic components, the flowing cool air from the HVAC system must flow past the lighting housings, simultaneously cooling the surgical lights and other electronic components, which can increase their longevity. For example, the longevity of LED lighting used in the surgical lights of the plenum can be improved when the flow of cool air through the plenum provides convective cooling that reduces the temperature of the LEDs below their standard operating temperatures. For example, the LEDs may be cooled from a standard operating temperature of 100 degrees Celsius (° C.) to an operating temperature of 75° C. In some embodiments, this increases the operational lifetime of LEDs to up to approximately 15 years.

In some embodiments, the integrated air and lighting plenum is modular such that installation involves mounting a plurality of subsections of the plenum in the ceiling to form the completed plenum. Such modular installation allows for easier installation given the size and weight of a typical integrated air and lighting plenum. The plenum structure can be brought into a room as a set of prefabricated sub-sections, then assembled and lifted into place where it can be joined to the HVAC system ducting. Sub-components, such as surgical light-heads and cameras, can be installed after the plenum is in place. An exemplary embodiment of a modular panel of a plenum that provides airflow is shown in FIG. 2D. The panel of FIG. 2D has a top 242 and bottom 244 panel joined by supports 248. Both the top and bottom panel comprise a plurality of cylindrical airflow outlets 246. The use of a double layer modular panel may provide additional structural stability to large sized plenums. A modular plenum allows for easy repair and replacement throughout the serviceable lifetime of the plenum by requiring only the removal of the effected parts without disassembly or removal of unaffected parts.

Figure 2I:
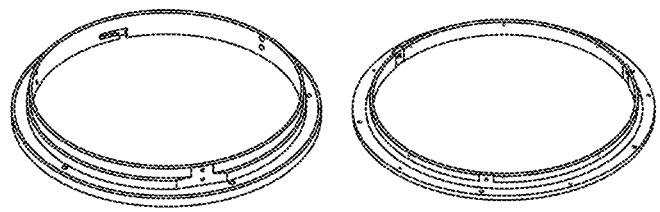
FIG. 2I shows mounts that may be used in housings to mount directional lighting (e.g., surgical lighting) in an integrated air and lighting plenum, according to an illustrative embodiment of the invention.

The modularity of a plenum can include not only the use of modular panels, but also the use of surgical lights and accessories that are easy to remove and replace, in contrast to currently available lighting systems. In certain embodiments, surgical lights are held in place by a fixation fastener and push-and-turn receiver. The two parts of such a push-and-turn receiver are shown in FIG. 2I. One part would be mounted to a surgical light and one part would be mounted to a housing of the plenum such that they interlock when the light is mounted in the housing. Removing the fixation fastener and rotating the surgical light slightly (e.g., 15 degrees) allows a malfunctioning surgical light to be removed and replaced by a properly functioning surgical light. This would allow for repair of the surgical light to take place outside of the room in which the plenum is located, thus limiting disruption to patients and staff. The light may be removed using a tool with a telescopic retaining ring unit that acts receive the light as it is released from the housing. A plenum comprising a plurality of modular surgical lights provides further redundancy to limit the impact of a malfunctioning surgical light and any associated disruptions. Accessories may be made modular by housing them such that they are secured by a mounting plate accessible from the exterior of the plenum. Such a mounting plate may provide a hermetic seal for the accessory.

Figure 2J:
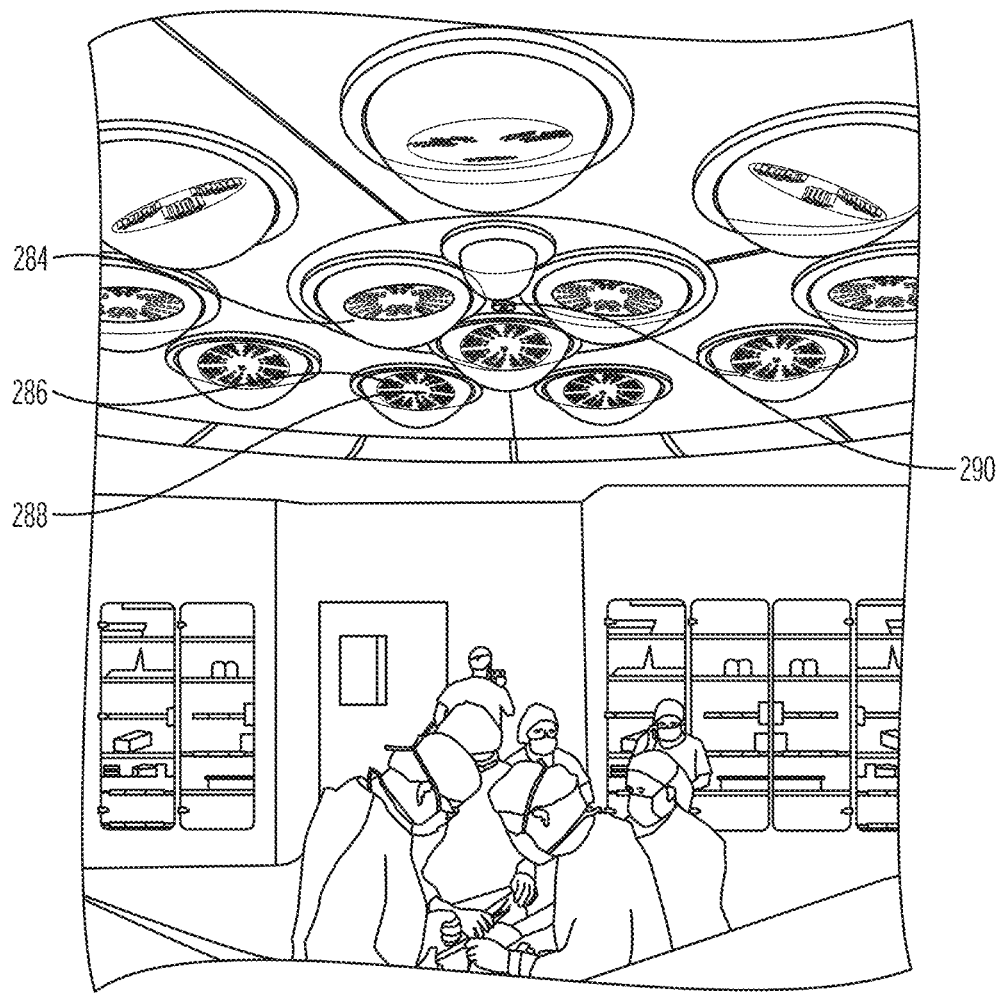
FIG. 2J shows surgical lights comprising an outer arrangement of outer lighting arrays and an inner arrangement of inner lighting arrays, according to an illustrative embodiment of the invention.
Figure 2K:
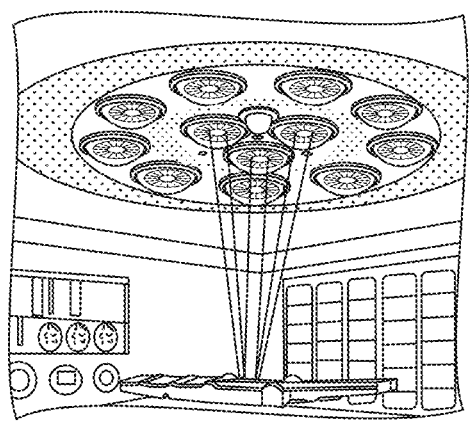
FIG. 2K shows an integrated air and lighting plenum where one spot-group of surgical lights is focused on a single focal point, according to an illustrative embodiment of the invention.
Figure 2L:
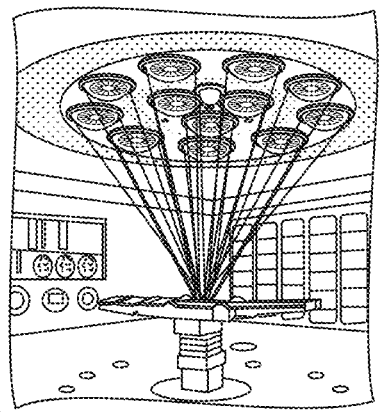
FIG. 2L shows an integrated air and lighting plenum where multiple spot-groups of surgical lights are focused on a plurality of focal points, according to an illustrative embodiment of the invention.
Figure 2M:
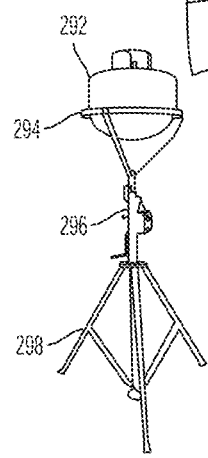
FIG. 2M shows a tool for removing surgical lights from an integrated air and lighting plenum, wherein a surgical light is resting in the retaining ring of the tool, according to an illustrative embodiment of the invention.
Figure 2N:
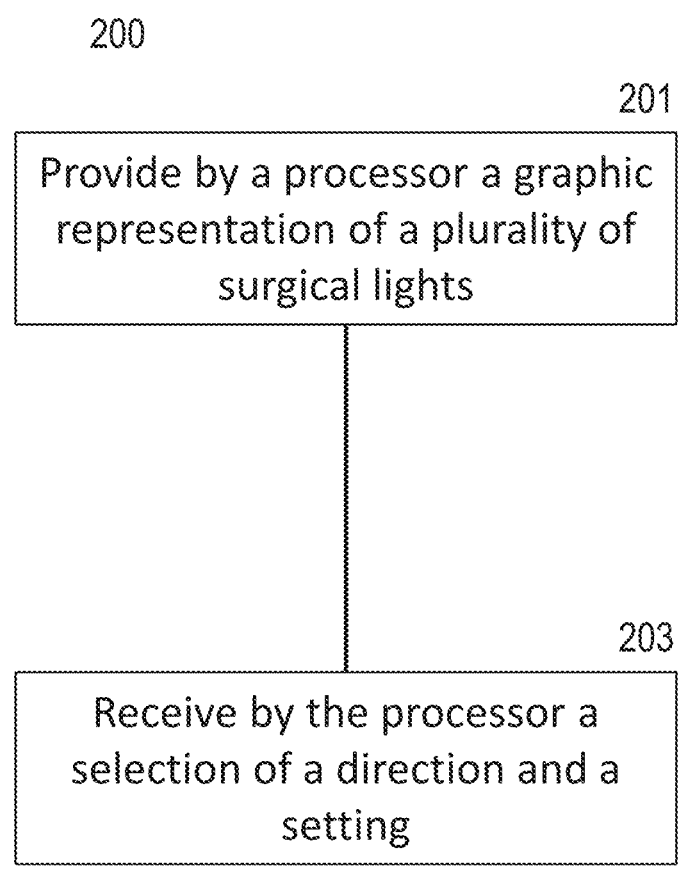
FIG. 2N shows a block diagram of a method for controlling an array of surgical lights corresponding to a surgical lighting system for an operation, according to an illustrative embodiment of the invention.
Figure 2O:
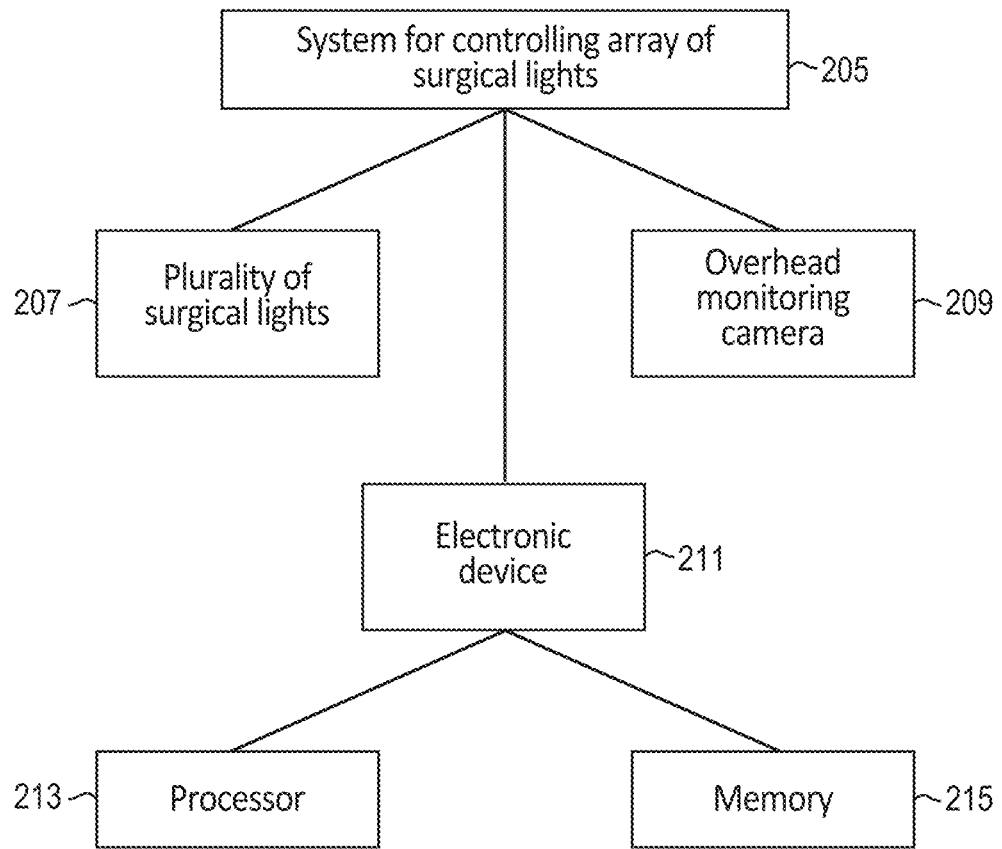
FIG. 2O shows a block diagram of a system for controlling an array of surgical lights, according to an illustrative embodiment of the invention.

A schematic of an illustrative embodiment of the tool for removing surgical lights is shown in FIG. 2M. A surgical light 292 that may have been recently removed from a plenum or is awaiting installation is held on the unit using a retaining ring 294 engineered to hold the light without interfering with any mounting hardware (e.g., a push-and-turn receiver) used to mount to a housing of the plenum. The telescoping feature of the tool may be accomplished using a telescoping unit 296 that attaches the retaining ring to a support base 298. The telescoping unit may using any type of telescoping mechanisms known in the art, such as a crank lever type mechanism that allows the surgical light to be raised in the air by turning a handle on the telescoping unit. The support base may be a tripod or other similar structure that provides stable support for the tool and surgical light during installation and removal through multiple points of contact with the ground.

Standard healthcare lighting fixtures limit the degree of control medical staff may exercise in terms of the light's orientation and optical properties (e.g., color temperature, spot size, brightness). Surgical lights used in the integrated air and lighting plenum allow the beam direction, spot size, focal point, brightness, and color temperature of the emitted light to be controlled. In some embodiments, surgical lights comprise two concentric adjustable arrangements of lighting arrays for providing directional lighting that are housed within a hermetically sealed (e.g., sterile) housing comprising a transparent cover, as shown in FIG. 2J. The transparent cover 284 of the housing may be constructed of any material suitable for maintaining the hermetic seal and limiting interference of the cover with the optics of the surgical light. A connection for power is used to power the surgical light. A connection for data is used to provide inputs to the surgical light to control and adjust the various optical properties of the surgical light (e.g., beam orientation, spot size, color temperature, brightness). The connection for data may be a connection for Ethernet, Bluetooth, Wi-Fi, fiber optics, or another type of connection for data known in the art. The use of a reduced number of connections (e.g., only one for data and one for power) for the surgical lights facilitates the easy removal and replacement of the surgical light for servicing.

In some embodiments with two concentric arrangements of lighting arrays, the use of two distinct arrangements of lighting arrays allows properties such as spot size and color temperature to be controlled more precisely. An outer arrangement 286 comprises a plurality of lighting arrays wherein each lighting array comprises a plurality of individual lights. Each lighting array in the outer arrangement may comprise two subarrays: one subarray comprising warmer lights and one subarray comprising cooler lights. The combination of separate warm white lights and cool white lights can allow for more precise control over the quality of light provided. An inner arrangement 288 also comprises a plurality of lighting arrays each comprising a plurality of lights. A multi-axis gimbal system disposed within the housing can be used to orient the lighting arrays such that the beam of light from the lighting arrays is positioned in a desired orientation. A motor disposed within the housing can be used to adjust the arrangements of lighting arrays in order to control the spot size of the beam and the focal plane of the light. In some embodiments, spot size can be adjusted between 3.5 and 18 inches. In some embodiments, the outer arrangement of lighting arrays can be turned off independently of the inner arrangement of lighting arrays. In some embodiments, the color temperature and/or brightness of one arrangement of lighting arrays can be adjusted independently of the other arrangement. Color temperature can range between 3000 and 7000 Kelvin. The maximal brightness achieved by a surgical light can be engineered to exceed regulatory requirements regarding lumens of light for a given setting of a healthcare environment (e.g., an operating room). In some embodiments, changing the color temperature of the lighting arrays does not alter the brightness.

In some embodiments, a group of three surgical lights (such as 224, 226, and 228 in FIG. 2C), herein referred to as a "spot-group," has each light of the group separated by an angular distance of 120 degrees from one another (e.g., is arranged to be equally spaced around a circle), the purpose of which is to illuminate a target area from multiple directions so as to eliminate shadows. The properties of light emitted from each surgical light, such as brightness and color temperature, may be altered individually in order to accentuate features of interest such as tissue in a surgical incision, for example. In some embodiments, additional surgical lights may be temporarily used as supplementary light sources for a spot-group. For example, a fourth surgical light 230 may be added to a group for a certain surgical procedure to in order to accurately illuminate the surgical site. Alternatively, any surgical light within a group may be turned off individually. An integrated air and lighting plenum comprising multiple spot-groups provides redundancy and allows multiple focal points to be selected at the same time. For example FIG. 2K shows a single spot-group focused on one point of an operating table while FIG. 2L shows a plurality of spot-groups focused on a plurality of points of an operating table.

Control software with a graphical user interface on a mobile computing device can be used to control and interact with individual surgical lights or spot-groups. In some embodiments, each surgical light and spot-group is individually addressable by a user. This allows complete control to obtain optimal lighting. In some embodiments, the position of the beam(s) of light produced by a spot-group can be controlled in two ways within the graphical user interface: by dragging a target icon on the interface for large-scale positioning and by tapping a virtual joystick for fine positioning. Using one or more cameras (290 in FIG. 2J and 236 in FIG. 2C) located in an integrated air and lighting plenum, the graphical user interface of the control software can display a live video overlay of the field-of-view of the cameras to allow medical staff to position or reposition the light from the surgical lights in a desired location remotely. For example, a nurse in an operating room can reposition the light coming from a surgical light or spot-group using the graphical user interface without entering the surgical zone around the patient.

Ozone Sterilization System for Efficient Sterilization of Healthcare Environments Maintaining the sterility of healthcare environments is of critical importance to reducing the risk of spreading infections and diseases amongst patients and medical staff. In certain settings of healthcare environments, the ability to maintain sterility can be quite difficult. For example, the surfaces of operating rooms and objects therein are frequently contaminated due to the spread of bodily fluids, cellular matter, or other matter from a patient during the surgical procedure. Additionally, airflow in such settings can facilitate the transfer and/or deposition of infectious matter (e.g., bacteria or viruses) throughout a setting in a healthcare environment. Typical sterilization procedures rely on strict adherence by one or more medical staff to clean (e.g., by scrubbing with hot water and/or sterilization chemicals) the desired area as they are able throughout the day. This approach is insufficient for modern healthcare environments given the complexity of surfaces within a given setting as well as the prevalence of various so-called "super bugs" that require special attention to avoid the spread of. Frequently, settings of healthcare environments, such as operating rooms, are left only partially sterilized. Additionally, areas such as duct work, corners at the intersection of two walls and the floor, and other difficult to reach areas serve as locations for culturing germs that will continue to spread throughout the setting or entire healthcare environment for a prolonged period given the difficulty and infrequency of their cleaning. Ozone and UV light based systems are known approaches to sterilization that circumvent at least some of the issues associated with traditional cleaning methods. These are commonly applied on a small scale, for example, to sterilize laboratory equipment, such as safety glasses, glassware, or probes. UV light is insufficient for scaling to a room sized space given its inability to wrap around corners. For example, a UV light located in the ceiling of an operating room cannot sterilize the floor or other surfaces located underneath an operating table given that the table surface blocks those surfaces from exposure to the light. Ozone gas can easily be permeated into a room for a period of time to allow sterilization of all surfaces exposed to the gas. However, a system utilizing such an ozone approach must ensure that ozone permeated into the room is sufficiently removed prior to re-occupancy of the room by humans, given that ozone is highly toxic. While attempts have been made to sterilize operating rooms using ozone generation, previous techniques have not been able to efficiently and sufficiently generate concentrations of ozone to kill detectable levels of potential contaminants. Furthermore, providing for an efficient and convenient removal of ozone in the operating has proven difficult given the design, structure, and often archaic technology of traditional operating rooms.

Figure 3A:
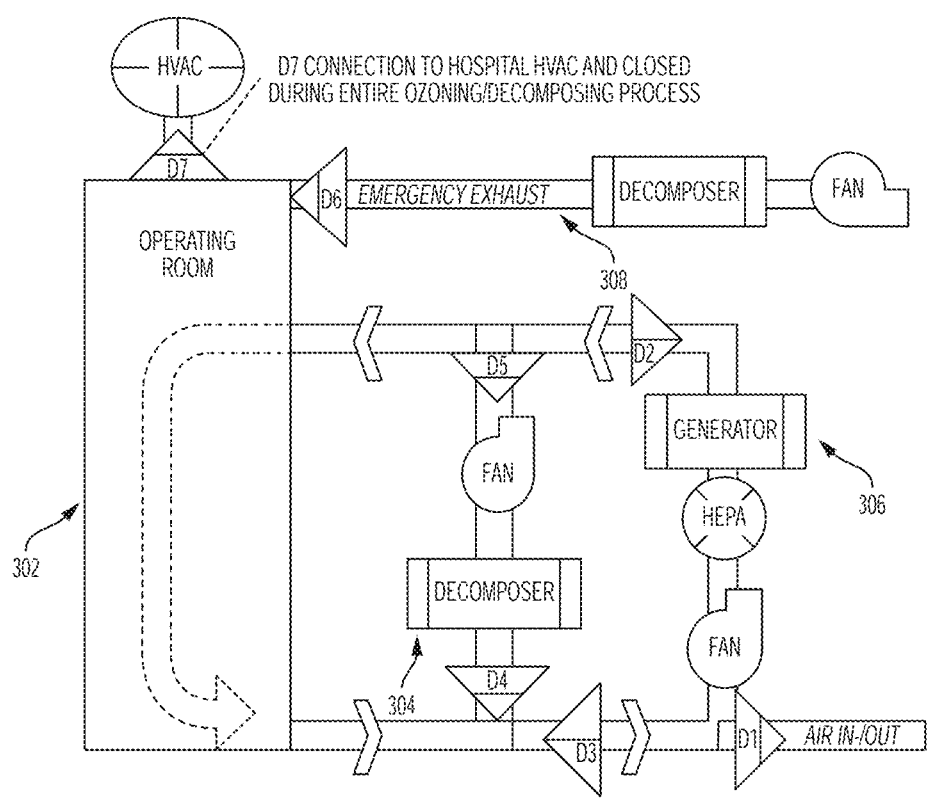
FIG. 3A shows a schematic diagram of the generation and exhaust components of an ozone sterilization system used to sterilize settings in healthcare environments, according to an illustrative embodiment of the invention.
Figure 3B:
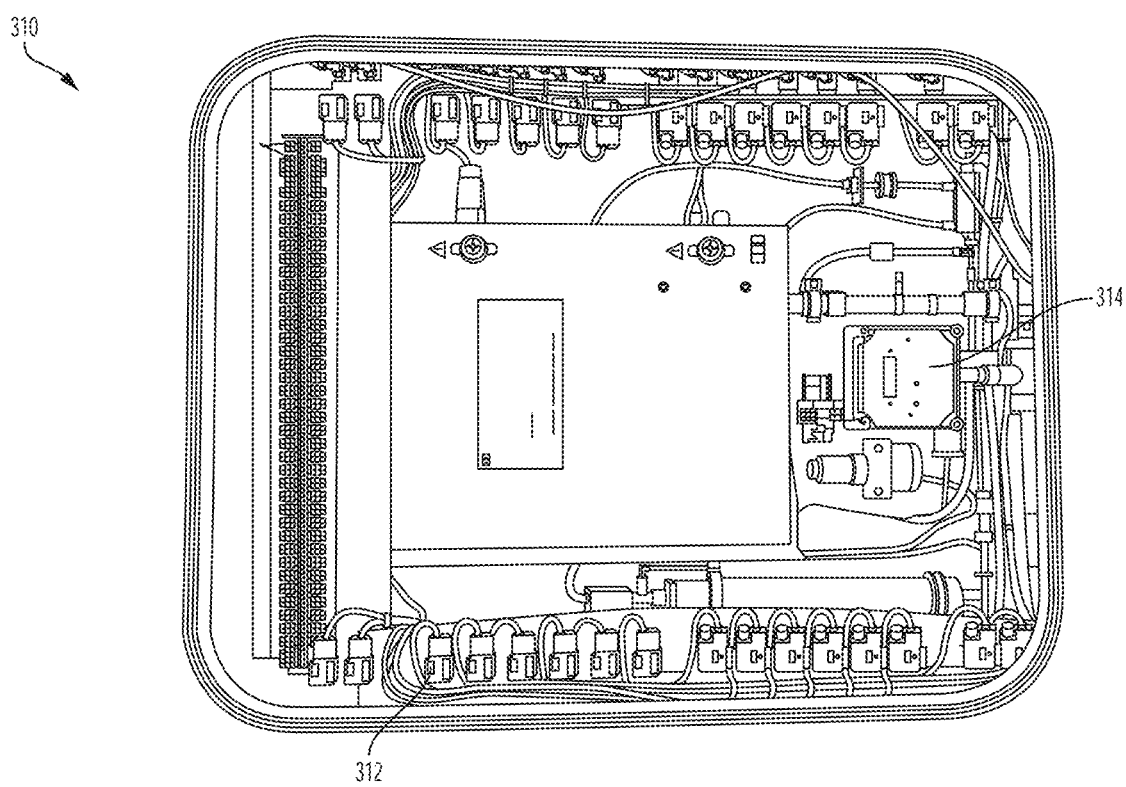
FIG. 3B shows an ozone sensing system that utilizes a plurality of "sniffers" located throughout a setting and connected by conduit to draw gas into a main sensing unit for detection of ozone, according to an illustrative embodiment of the invention.
Figure 3C:
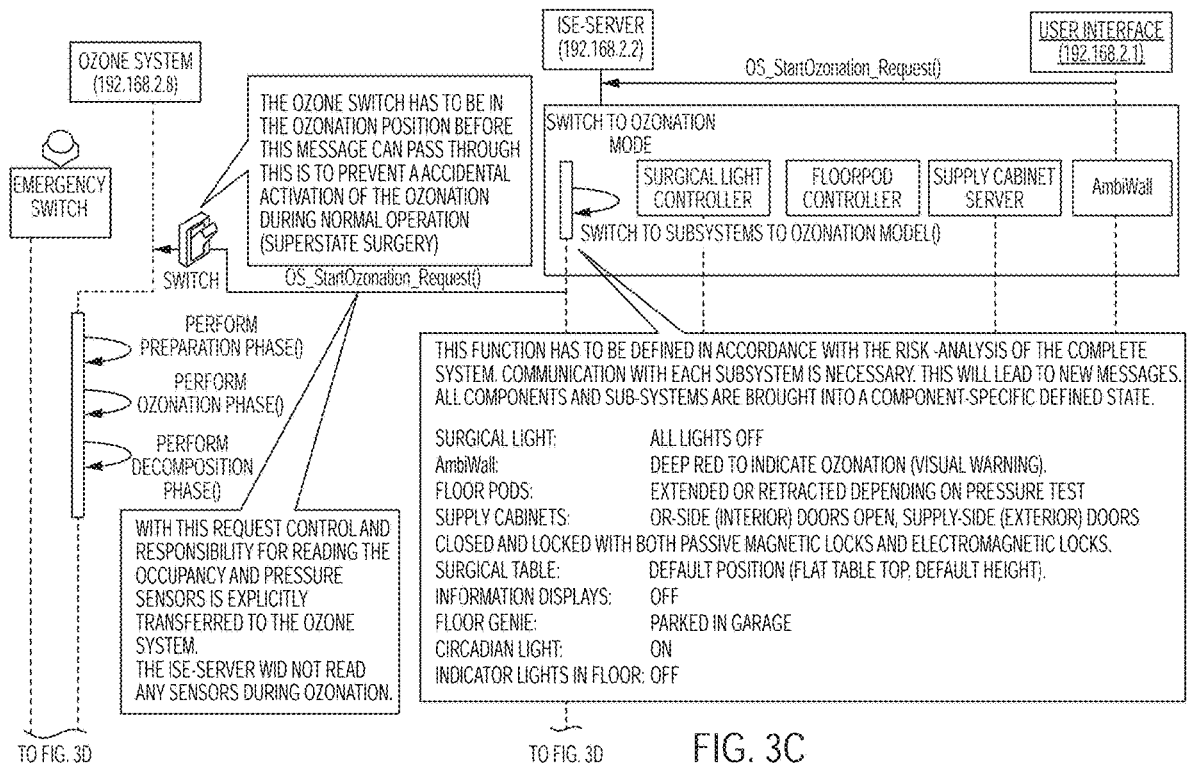
FIG. 3C-D shows a block diagram of control software that can be used to operate an ozone sterilization system including reference to activation and emergency switches, according to an illustrative embodiment of the invention.
Figure 3D:
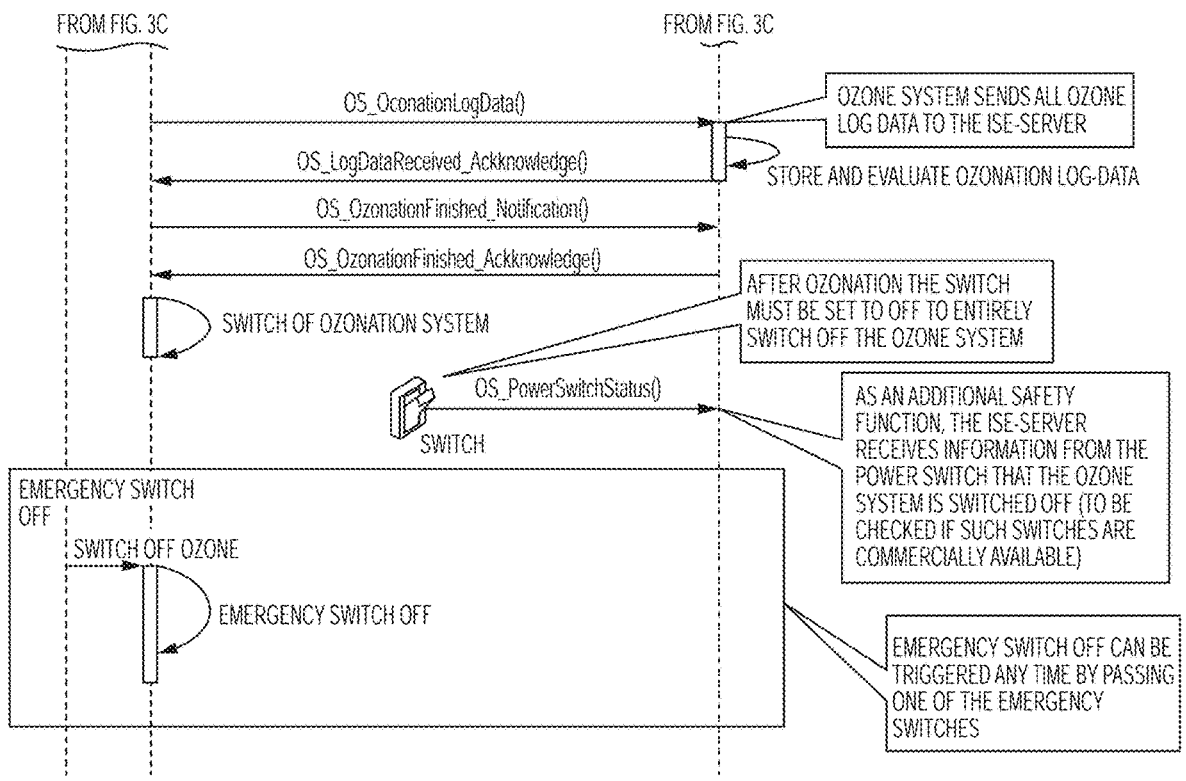
Figure 3F:
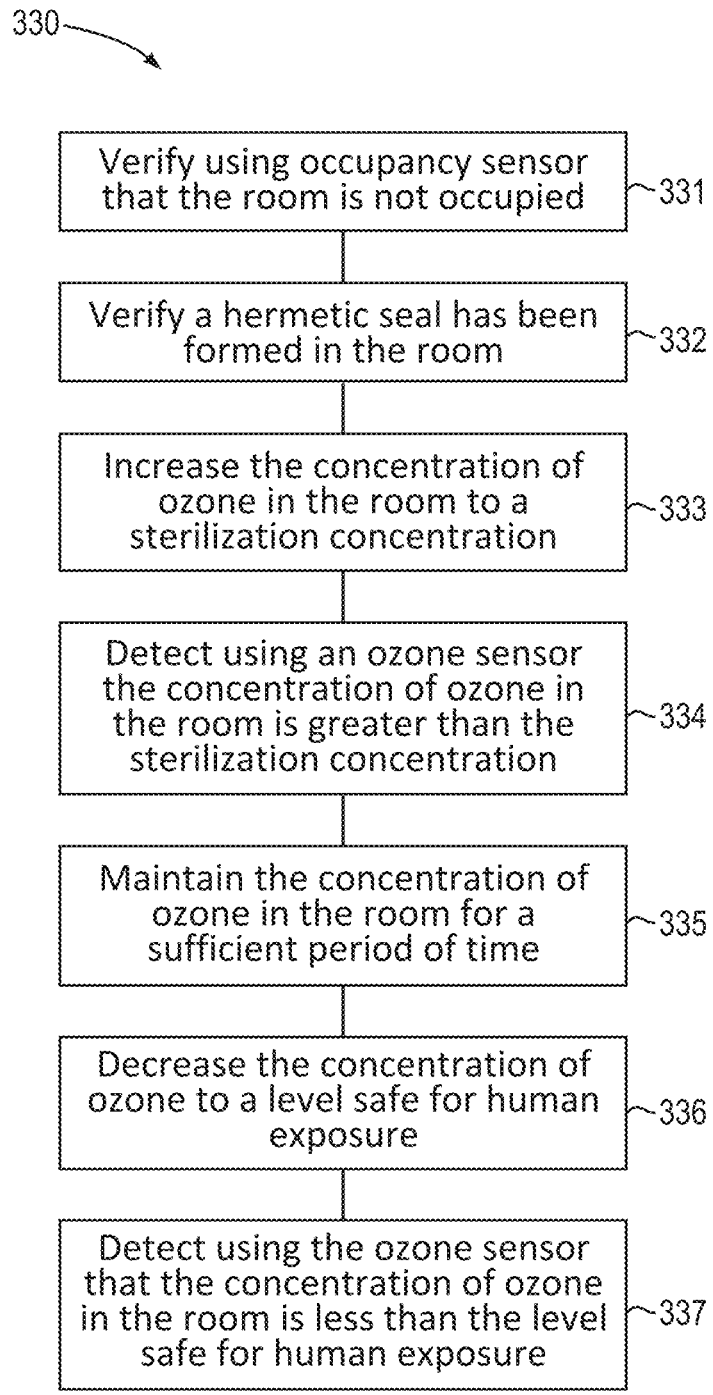
FIG. 3F shows a block diagram of a method of sterilizing one or more rooms, according to an illustrative embodiment of the invention.

In certain embodiments, described herein is a system for creating a sterilized setting in a healthcare environment using ozone gas, wherein the source of the ozone gas is integrated into the HVAC system for the setting. An ozone sterilization procedure may be run once a week or more frequently. In some embodiments, one ozone sterilization system can service up to 5 settings of a healthcare environment (e.g., 5 operating rooms) simultaneously. In some embodiments, when a sterilization procedure begins, control software causes the setting to enter what may be referred to as an "Ozone State," where no other systems in the setting are operable (e.g., doors cannot open, cabinets cannot be opened, lighting color cannot be changed) other than the independent ozone control system with a manual override to emergency exhaust the setting. This is schematically shown in FIG. 3C-D. In some embodiments, large main HVAC dampers are positioned into "closed" position after a positive pressure test has been performed to check for potential air leaks prior to continuation of the ozone sterilization procedure. The ozone control system can then take control of the setting and runs the ozone sterilization procedure. In some embodiments, the procedure is a 3 hour cycle of ozonation: 1 hour at elevated ozone concentration (e.g., 70 ppm ozone, 80 ppm ozone, 90 ppm ozone), and 2 hours of ozone catalysis until complete depletion of ozone to below ambient air levels. After completion of the procedure, doors are freed to open and other systems within the setting can be operated as normal.

In some embodiments, the system is designed to bring an operating room—with a typical volume of approximately 245 cubic meters—to ozone levels at or above 60 ppm, and then hold that level for a total of 2 hours. The system then automatically enters the deconstruct (decompose) phase, reducing ozone to safe levels of 0.030 ppm in approximately 1.5 hours. The associated blower, duct, and damper section can be designed such that ozonation is accomplished without raising room pressure levels above the capacity of the appropriate door seal or duct damper seals.

In certain embodiments, the ozone sterilization system consists of 10 subsystems: an ozone generator with oxygen supply, wall- and duct-mounted ozone sensors, room occupancy sensors, differential room pressure sensors, ozone decomposers, a computerized control and monitoring system, an emergency roof exhaust with ozone decomposer, an emergency stop button/procedure, a dual safety start-switch button/procedure, and a battery backup power supply to power decomposer fans, damper actuators, and the control system. FIG. 3A shows a simplified schematic representation of these components.

The ozone generator 306 can be a corona lamp discharge generator which converts a stream of oxygen gas into ozone, and mixes it into a moving air steam which is then ducted into the setting. The oxygen flow rate for ozone conversion is established during initial setup of the ozone system.

In some embodiments, an ozone sterilization system comprises an ozone generator 306 for generating ozone used in a sterilization procedure, wherein the ozone generator comprises a system for generating a corona discharge, a heat exchanger, a conduit for partially circulating a portion of the gas leaving the generation zone of the generator, and a circulation pump. In such an ozone generator, a portion of ozone-containing gas leaving the generation zone is circulated through the heat exchanger and combined with an oxygen-containing gas forming a feed gas. The cool feed gas is fed to the generation zone of the generator and used in the zone to form further ozone. The feed gas cools the interior of the generator and increases the concentration of ozone in the gas leaving the generator. The ozone generator has a first electrode and a second electrode. The electrodes are spaced from each other and define between them the ozone generation zone. The inlet of the zone receives the feed gas comprising oxygen, and the outlet of the zone releases a gas mixture of the feed gas and ozone which is generated in the zone. A first coolant is in heat exchange relation with one surface of the first electrode. The heat exchanger has a gas side and a first coolant side. The gas side is in fluid communication with the zone. A second coolant in the first coolant side acts to cool the gas circulated through the gas side of the heat exchanger. The conduit is in fluid communication between the zone and the gas side of the heat exchanger and is configured for receiving a portion of the gas mixture which leaves the outlet of the zone. The pump circulates the portion of the gas mixture through the conduit, the heat exchanger and the zone.

In a method for generating ozone, a feed gas comprising oxygen, as described above, is introduced into the ozone generation zone in an ozone generator. A corona discharge is created between a first and second electrode in the generator to form ozone within the zone from the oxygen in the feed gas. A surface of the first electrode is cooled with a first coolant. A mixture of ozone and feed gas is released from the zone, and a portion of that mixture is drawn through a heat exchanger to be cooled. The first portion of the mixture drawn through the heat exchanger is combined with a gas comprising oxygen to form the feed gas.

Ozone sensors may be located in the walls of the setting 302, adjacent rooms and/or in relevant ducts related to the setting. In some embodiments, there are low-level sensors that indicate safe levels of ozone as well as high-level sensors that assure the required levels for disinfection purposes. In addition there may be additional low-level sensors monitoring ozone levels behind one or more walls that form a façade in the setting (e.g., in rooms where there may be a first wall interior to a second wall). If there are leaks in areas where ozone is prohibited, the ozone control system instantly receives reports and can take appropriate action.

In some embodiments, there are ozone sensors in the ducts in key locations throughout the system to tell the ozone control system when there are leaks past damper seals, and when appropriate high levels are reached. These sensors were developed particularly for this application and tested and calibrated.

In some embodiments, a central ozone detector is used for all ozone detection, wherein conduit connects the sensor to ozone sniffers in or near the setting of intended sterilization (e.g., in the walls of the setting or the walls immediately outside of an entrance to the setting). For example, FIG. 3B shows a central ozone sensor 310 comprising an ozone sensing unit 314 and a plurality of gas inputs into the sensor 312 connected by conduit. The sensor may comprise a backup sensing unit to verify the readings of the primary sensing unit and/or to provide redundancy. The sniffers are used to draw ambient gas from the local environment into the conduit (e.g., by providing suction) for use with the sensing unit in detecting the concentration of ozone in the local environment around that sniffer. By testing each sniffer in sequential order, a profile of the ozone concentration in and around the setting can be developed such that the exact location of any leaks can be identified. Such a system of sniffers and a central sensing unit reduces the complexity of the system by reducing the number of sensors that need to be calibrated and monitored for functionality. It also simplifies the process of adding or repositioning sniffers throughout the setting and its surroundings.

In some embodiments, there are four room occupancy sensors mounted in the ceiling. Each sensor may have two redundant infrared sensing heads so that if one fails the unit is still viable. These sensors report to the control system to prohibit ozone system actuation if anyone is in the room.

In some embodiments, a differential pressure sensor is mounted in a wall and positioned close to the entrance to a setting for the purpose of indicating leaks either thru the closed doors, a closed pass-through logistics cabinet or past any relative closed damper. This may be done as follows: the ozone generator blower (without ozone generation) raises the room pressure slightly and the ozone control monitors the resultant pressure levels to determine if leaks are indicated. If so, the system start is halted and maintenance is called.

In some embodiments, there are two redundant decomposer units (304 in FIG. 3A) with associated blowers and ducts in a closed recirculation loop that deconstructs ozone back to ozone. The process is done at room temperature with special catalyst conversion materials, such as manganese dioxide and copper oxide. Ozone destruction efficiency is a function of residence time thru the length of catalyst material at its linear flow velocity. Residence time in the catalyst of 0.36 seconds or more reduces ozone to oxygen completely regardless of concentration. Lengths of catalyst paths can be specifically designed in the decomposer to assure 100% reduction for a single pass, for a chosen ozone-air mix flow rate. While, in some embodiments, one decomposer would suffice for the size of a given setting, another decomposer is added to handle a worst case unit failure scenario. The power to run the decompose system may be supplied by a smart power system's batteries to avoid risks associated with events where power from the healthcare environment's usual systems is not available (e.g., a main power failure and/or back-up power failure).

In certain embodiments, the external computerized ozone control system and user interface initiates a procedure upon appropriate user authentication and when safe conditions are noted by all the relevant sensors. The control system runs the sterilization cycles, turns off the system, and provide emergency shut down procedures. In some embodiments, the control system turns on the ozone generator, controls the supply of ozone to the generator, opens and closes respective ducts via associated dampers and blowers, controls the blowers feeding the decomposers, and receives information from door locks, latches and other associated equipment. Software associated with the computerized control system for the ozone sterilization system is written to meet IEC-62304 and IEC-14971 standards.

For added safety, a separate roof exhaust escape duct and blower is utilized with a third ozone decomposer/scrubber to remove ozone from the setting to the roof and out into the surrounding air at safe levels. In some embodiments, power for the emergency exhaust and associated dampers are supplied by a separate smart power system's batteries, similarly to the main ozone sterilization system. This allows the setting to be made safe for occupancy even in the event that a healthcare environment's power is unavailable while an ozone sterilization procedure is running. The emergency exhaust system is activated under a variety of abnormal conditions, including detection of ozone leakage into adjoining spaces. This emergency exhaust procedure is intended to restore the space to normal levels as fast as possible. The ozone levels at the exhaust can be measured in a test facility to ensure safety standards.

In some embodiments, there are three red emergency override stop buttons that an operator can press to initiate emergency system shut down procedures. This is part of an independent hardware-based override system that will lock the entire system into a predetermined configuration (e.g., which devices are on/off or open/closed), for a fixed period of time (normally 3 hours), following an emergency shutoff red button command. This ensures reduction of ozone concentration to safe levels if an emergency, such as a fire, should occur during an ozone generation period without relying on software. Red stop buttons may be located, for example, in a hallway, in an area opposite the a pass-through logistics cabinet, in a pre-anesthesia or other pre-operative room, or close to the position of an ozone control panel. In addition, a fire/smoke alarm condition may be used to trigger an emergency exhaust procedure.

In certain embodiments, dual safety start-key switches are located alongside the ozone system control panel a utility room. An operator may have to remove the key from one switch (e.g., one that enables normal operation of other room systems) and insert into the second switch to enable the ozone mode. This precludes an accidental activation of the ozone system by personnel.

In some embodiments, the entire system is controlled by a dedicated ozone server powered by its own redundant 24 V DC power supply system and supported by a separate dedicated local inverter, to ensure stack exhaust blower and decomposer operation. In addition, backed-up power is supplied to all related damper/actuators, ozone supply valves, sensors, and blowers.

Pass-Through Logistics Cabinet for Storage and Retrieval of Medical Supplies

Storing medical supplies that may be needed for treatment of a patient (e.g., in-patient and out-patient procedures and patient monitoring) presents several infrastructural risks that can be mitigated or eliminated with an engineered cabinet for storing the supplies. Risks or risk factors that can be reduced in embodiments of the cabinet of the present disclosure comprise: surgical delays induced by time spent locating supplies or resetting after staff bring in supplies not present in an operating room, increased contamination due to airflow in and out of a patient room, and misidentification of supplies based on their location on a shelf or in a cabinet.

In certain embodiments, described herein are pass-through cabinets that mount into the wall of a healthcare setting for storing and retrieving medical supplies such that the cabinets are accessible from both side (e.g., inside and outside a room in which they are installed). In certain embodiments, the pass-through logistics cabinets allow supplies to be introduced into an operating room without having to physically enter the operating room, especially during the time of an operation, thus reducing the number of disturbances to concentration of the surgical staff. In some embodiments, this can be accomplished by mounting the cabinet in a wall such that an interior door exists inside an operating room and an exterior door exists outside an operating room. Mounting the cabinets in a wall has additional benefits such as minimizing surface area exposed to a room, thus reducing surface area available for contamination and easing cleaning. Cabinet doors are engineered to have increased durability, compliance with sterilization protocols, and fire ratings. In certain embodiments, this means the doors are made of stainless steel and glass. In certain embodiments, one wall of a setting is filled by RFID-enabled pass-through supply cabinets. In certain embodiments, a slight overpressure of air within a healthcare setting ensures positive airflow out of the cabinets when opened from the supply side.

Each cabinet can have a number of shelves (e.g., up to six or more shelves) in order to allow better organization of the supplies. The cabinets shown in FIG. 4A have six shelves. The cabinets can be stocked and re-stocked from the outside. In some embodiments, interior lights illuminate shelves in the cabinet to provide better visibility when stocking and re-stocking. In certain embodiments, opening an interior or exterior door prevents the other door from being opened by one or more electromagnetic locks. This can reduce airflow through the cabinet in order to reduce the likelihood that contaminated air is allowed into or out of the room. In some embodiments, the cabinets are engineered to be modular to allow the shelves and associated electronics to be removed for servicing without compromising the functionality of the remaining modular components.

In certain embodiments, radio-frequency identification (RFID) readers are used to track supplies and update their status in a database. Removing or placing supplies on a shelf or in a cabinet equipped with an RFID tag would prompt the RFID reader for that shelf or cabinet, respectively, to update the database. In certain embodiments, the database can be viewed using a graphical user interface on a computing device (e.g., a tablet, a smartphone, a computer). Other known proximity sensors may be used as well, such as near field communication sensors. One or more sets of status indicator lights are used, in some embodiments, to alert a user of the status of supplies on a given shelf or in a given cabinet (404 in FIG. 4A). For example, an RFID equipped cabinet could be used to determine if all packages needed for an operation are present prior to the start of the operation, and to check which packages need to be replaced. In some embodiments, the ID of the packages is pseudo-random and can't be associated to the content by only looking at the ID. In certain embodiments, operations are planned using software not related the cabinet, and relevant IDs corresponding to supplies for procedures are correlated with the cabinet database in order to allow a common reference for those supplies to be used throughout the hospital. In some embodiments, near field communication (NEC), Bluetooth, or other similar known short-range data transfer protocols may be used for identification in place of RFID.

In some embodiments, to check if all of the supplies for the next operation are present, the packaging of the supplies comprises one or more passive RFID tags that comprise not only unique identity identifier numbers, but also a complete list of contents of each package of supplies, so that they can be seen on a user interface when queried. Alternatively, when individual supplies, either disposable or reusable, are queried for, it is possible to identify the particular package and location of the supply desired. In certain embodiments, these tags send out an ID when placed in proximity to an RFID antenna located on the top of each shelf. In some embodiments, the cabinets may have two antennae per shelf, thereby enabling the location of a package on the shelf in 2-dimensional space on the user interface.

The one or more sets of status indicator lights may be sets of colored LEDs (e.g., a red, green, and blue LED) in order to indicate a number of different equipment states, each state correlated with one LED in the set. The lights may be able to be turned on and off individually. In certain embodiments, three lights are used where one is red, one is blue, and is green such that supplies on a shelf needed for the next operation is indicated by a green light; newly passed-through packs or equipment queried for on operating software and subsequently delivered during an operation is indicated by a blue light; and a shelf where a necessary supply was present prior to surgery but removed without knowledge or consent of those in the operating room is indicated by a red light. A cabinet with such an indicator color scheme can assist operating room and re-stocking staff in finding packages and thus reduce delays in a surgical procedure. The status indicated by one or more of the lights as described above is only exemplary as the ability to indicate many other statuses could be incorporated in the cabinet by use of more lights with different colors, different intensities of light, or different durations of illumination (e.g., light flashes or pulses), for example. For example, an illuminated status indicator light could indicate that supplies are present on the shelf but relevant to a present query or surgical procedure; that supplies on a shelf have been present for a certain time without being used; or, that the number of a certain supply on a shelf is below a certain quantity. The pass-through logistics cabinets shown in FIG. 4A have some shelves which do not have a status indicator light illuminated, one with an illuminated red light, several with illuminated blue lights, and several with illuminated green lights. The exemplary state of the pass-through logistics cabinets shown in FIG. 4A would be typical for an operating room in the middle of a work day.

Figure 4A:
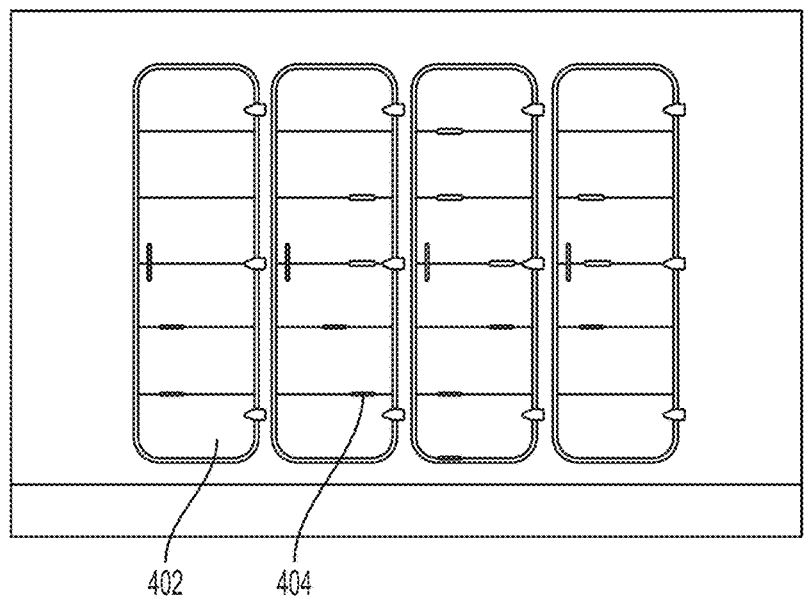
FIG. 4A shows pass-through logistics cabinets installed in a wall of a healthcare setting comprising a plurality of shelves, photochromic glass doors, and sets of status indicator lights for each shelf, according to an illustrative embodiment of the invention.

In some embodiments, the interior and/or exterior door comprises photochromic glass or equivalent materials to provide privacy at certain times in an operating room (402 in FIG. 4A). For example, the opacity of photochromic glass may be increased in order to protect a patient's identity and privacy or to reduce distractions to a surgeon during the procedure. In some embodiments, indicator lights remain visible when a door is in an opaque state. Control over the level of opacity of the photochromic glass can be integrated into software controlling the cabinet so that it can be changed from anywhere in the room on a mobile computing device. The photochromic glass may be made fully transparent to assist in locating supplies using the control software. The doors may revert back to high opacity after a preset time in order to eliminate the need to manually change the opacity again.

In some embodiments, one or more pass-through logistics cabinets are integrated into the rest of the hospital surgical logistics environment. The pass-through logistics cabinet can also allow for the capabilities needed to achieve the full-circle delivery of disposable and non-disposable sterilized packages of supplies being ordered as part of the operating room scheduling process, the packages being placed in the cabinets, being searched for by operation-room staff, and logistics queries back to the central supply area for replenishing and new scheduling requirements for upcoming days' surgeries. Such a system can allow operation-room staff to get an overview on what is stored where and search for certain packages. When found, the location of the package is indicated by visual feedback both on end user and logistics staff user interfaces, as well as the local indicators of LEDs built into the shelves of the cabinets in the operating room. For example, a graphical user interface accessible inside the operating room may display an icon, image, or text describing supplies as well as a corresponding location comprising shelf and cabinet numbers while the appropriate LED is lit.

In some embodiments, a server maintains a real-time overview of which IDs are present throughout the system, and where they are in relation to the readers both in the operating room but also in the logistics supply areas. The server communicates with a logistics-module (LM) that can tell it which packages should be present and what their IDs are, in relation to a logistics-scheduling module. The logistics module can also assist logistics personnel in re-stocking, as it knows which packages have been removed from the operating room, have moved out of the system, or require replenishment via new orders, as for example with disposable items and damaged instrumentation. A logistics-module can have various modules that can be interactively modified to communicate to the preexisting logistics systems present in hospitals (e.g., SAP). Those modules are designed, and can be expanded, to be implemented on a per-healthcare environment systems basis so that they can be re-used and re-configured for other hospitals with the same logistics product.

The interface between a server and a reader can be kept very simple. In some embodiments, communication between the server and the reader comprises one call to get all the IDs and location (e.g., cabinet number, shelf) of those IDs. The server can then communicate with the cabinets to highlight a certain ID. A predetermined colored light can then illuminate to indicate the status of the supplies on that shelf. The user can search for individual items, packs and trays, or all of the supplies for a specific surgery. As shown in FIG. 4S, the location sensors (e.g., RFID readers) 476 can provide data to the cabinet controller 480 about what supplies are located within sensing distance of the sensor. The controller 480 can send commands to the status indicator lights (e.g., LEDs) 478 as well as send data regarding the location of supplies to the controlling server (e.g., ISE) 484. The server 484 can communicate with the logistics module 482 to relay information regarding the supplies. The server is controlled by a graphical user interface (e.g., UI) 486.

In certain embodiments, the logistics module serves one file containing all information about an operation. This may include patient information, equipment and disposables needed for the operation as well as scheduling and personnel staffing specifics. In certain embodiments, the LM is the main interface to various healthcare environment data systems to combine the information stored there. The LM can interact with a healthcare environment information system (HIS) database to coordinate radiology (PACS), patient information (e.g., laboratory information), and surgical planning information in order to know the combined needs a next set of scheduled treatments or procedures, as diagramed in FIG. 4R. Different healthcare environments will have different systems covering one or more embodiments of those systems. Software plugins enable the LM to interact with a wide range of systems, with the goal that for installation of a server comprising the logistics module in a new healthcare environment, re-usable plugins can be provided that only need to be slightly configured or parameterized. As the development of such plugins should not involve deep knowledge of the control software on the server, being based on very simple interfaces, limited effort is required for an owner of such a hospital-wide logistics system to integrate the server that controls the pass-through cabinets. Communication to the local server is done over HTTP using a RESTful with JSON as payload. The server will only listen to requests coming from the server's LAN, to avoid data-leakage.

Plugins can be written in any programming-language necessary. Communication can be done bi-directionally using RESTful HTTP and JSON as payload. The plugins won't run directly in the LM process to ensure one malfunctioning plugin can't take down the entire service. Plugins can either be found by DNS entries or configuration. One plugin can offer one or many interfaces. If the logistics-plugin can also provide patient-records it will register itself twice with the LM. Before an operation starts the local server tells the LM the new operation-identifier. The LM then communicates with each plugin the new operation-identifier to initialize them. All calls must contain the operation-identifier to avoid having stateful plugins that consume old-data on start-up if they missed the initialization. In the information-gathering phase the plugins talk to their respective systems, and also communicate back to the LM for more information from other plugins. The local server also communicates with the LM to identify all surgical packs currently present in the cabinets. The logistics plugin type can translate an RFID-ID to a package ID. This package ID may then later be translated into a full record, including symbols and/or photos to use by the user-interface. In multilingual environments, localized names should be provided.

The server can operate completely autonomous from the healthcare environment network once the operation has started. It downloads patient-records, supply-information, as well as other information during an "information-gathering" state. Afterwards it enters a fixed "operation-in-progress" state, where no communication to any outside system other than logistics area queries when needed. At the end of each operation, the "operating in progress" state expires, and the ISE server resets its logistics information set to the current planned operation, and dumps the cached information from the prior procedure.

The RFID Search user interface can be operated from a wireless computing device. After secure login, the user can tap on a component in the home screen graphic or use the component dock at the bottom of the screen to select the desired UI for that component.

In certain embodiments, a user searches for supplies in the pass-through logistics cabinets of a setting of a healthcare environment using a graphical user interface on a wireless computing device that is connected to the control server for the room. An illustrative embodiment of such a user interface used in searching for supplies is shown in FIGS. 4B-4Q.

Figure 4B:
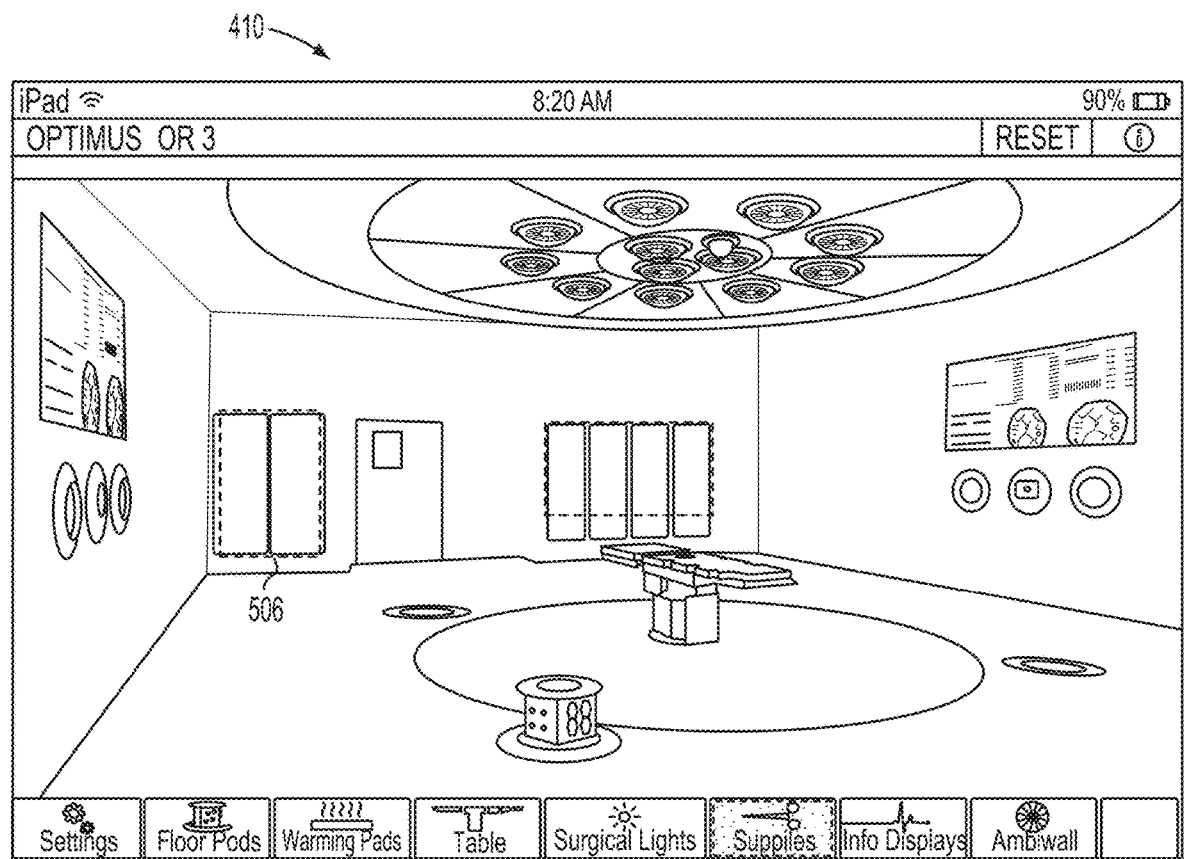
FIG. 4B shows a graphical user interface for controlling pass-through logistics cabinets where a search for supplies can be performed by selecting either one of the cabinets (highlighted in red) or the "Supplies" icon in the bottom row of icons, according to an illustrative embodiment of the invention.
Figure 4C:
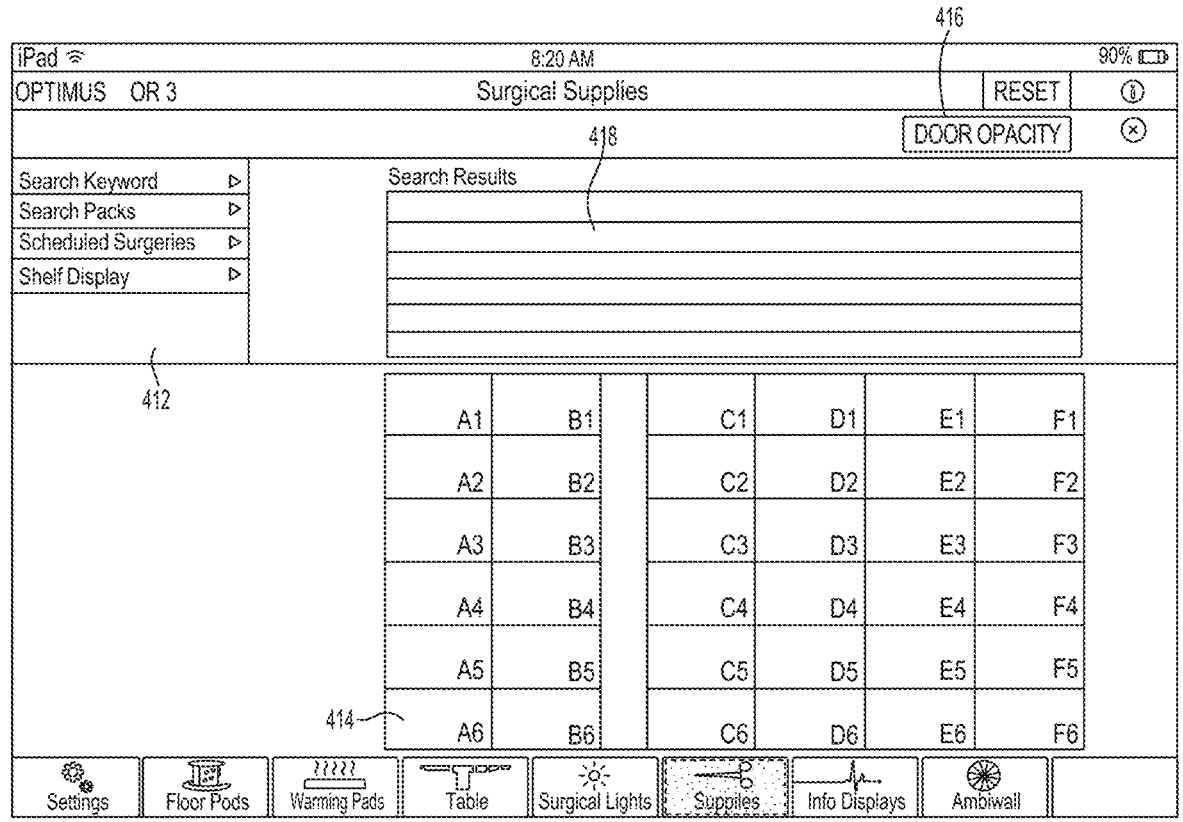
FIG. 4C shows a default search screen comprising a panel of search types (e.g., "Search Keyword," "Search Packs," "Scheduled Surgeries," and "Shelf Display"), a panel for displaying search results, a button to control the opacity of photochromic doors, and a two dimensional "cabinet view" array, according to an illustrative embodiment of the invention.

In the interface of FIG. 4B, the user can tap on either the cabinets 406 or the "Supplies" icon 408 at the bottom of the screen. Selecting either option brings up a search home screen of the type shown in FIG. 4C. The search screen comprises a search type panel 412, a search results panel 418, a "cabinet view" panel 414 comprising a two dimensional array of icons corresponding to different locations within the cabinets, and a door opacity icon 416 for controlling the opacity of photochromic doors. Each letter-number combination in the cabinet view panel corresponds to a unique location, wherein each letter corresponds to a unique cabinet and each number corresponds to a unique shelf. In some embodiments, the search type panel 412 offers the wireless computing device user four options to select from to search for needed surgical supplies: "Search Keyword," "Search Packs," "Scheduled Surgeries," and "Shelf Display."

Figure 4D:
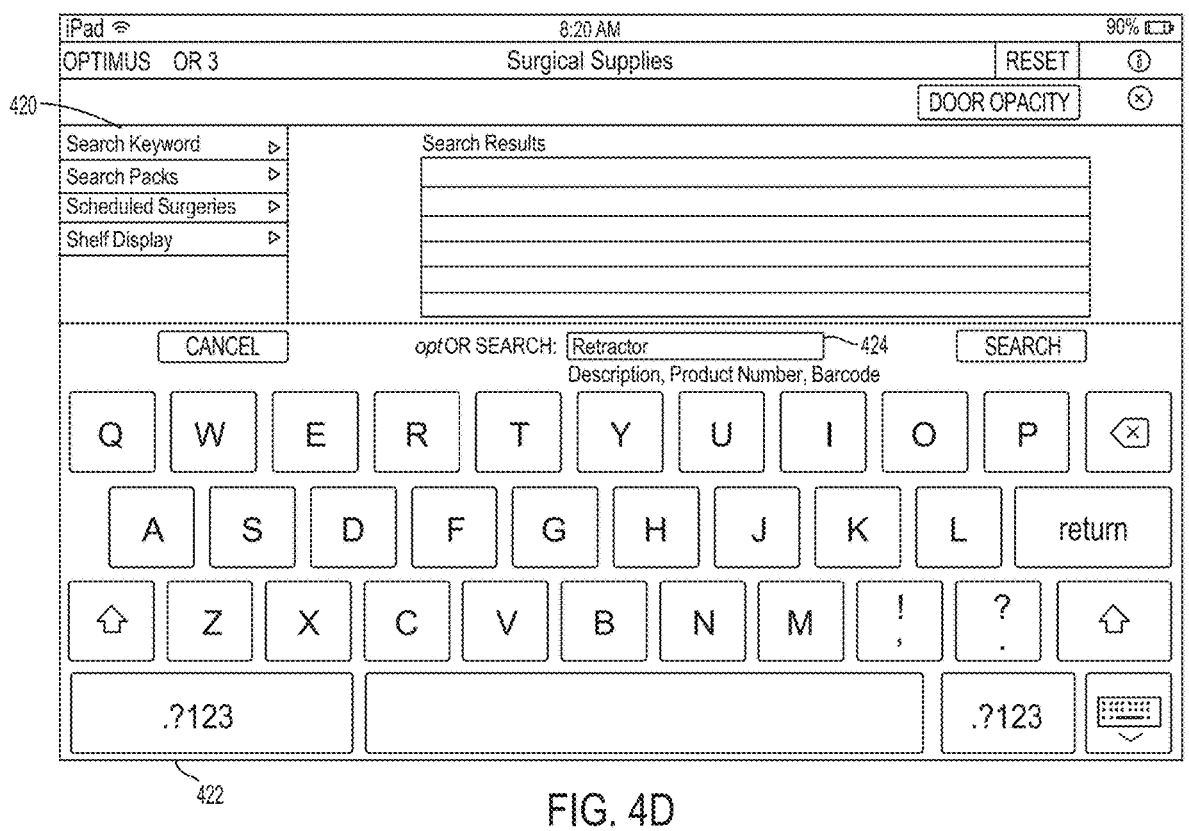
FIG. 4D shows a keyword search input provided by a graphical keyboard, according to an illustrative embodiment of the invention.
Figure 4E:
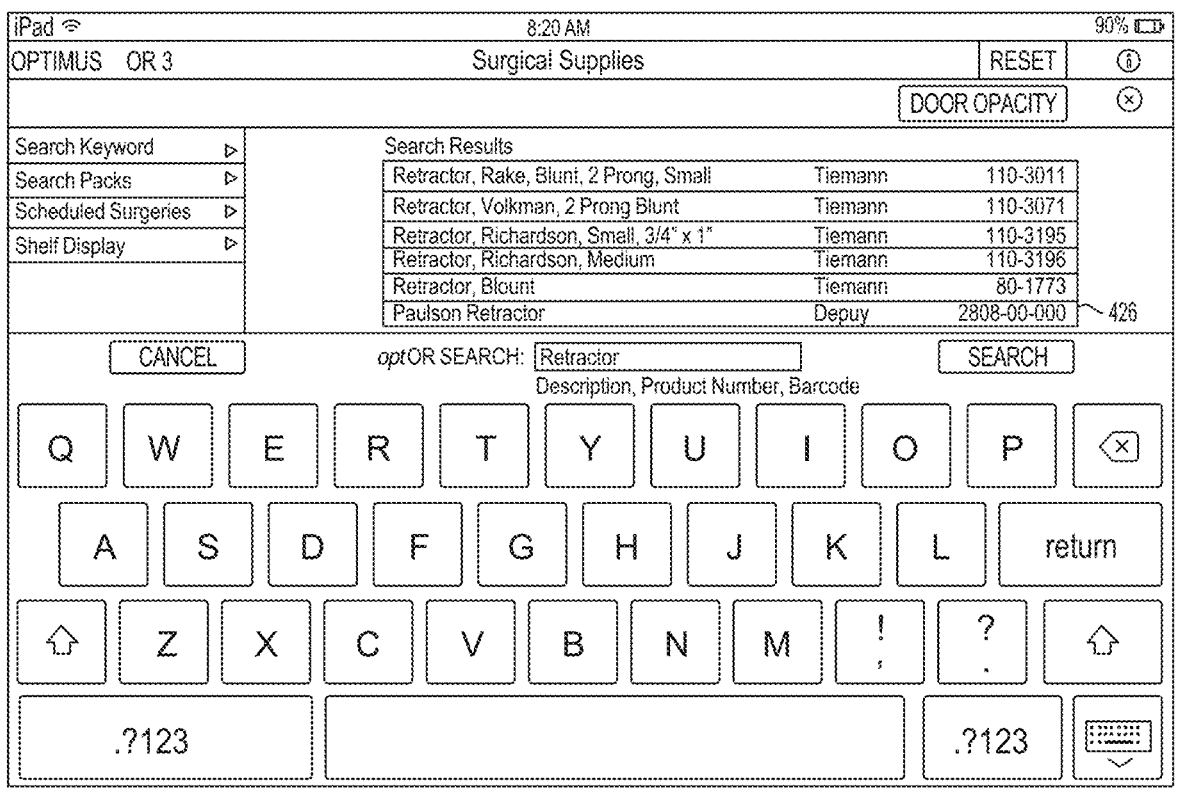
FIG. 4E shows the results of the keyword search of FIG. 4D, according to an illustrative embodiment of the invention.
Figure 4F:
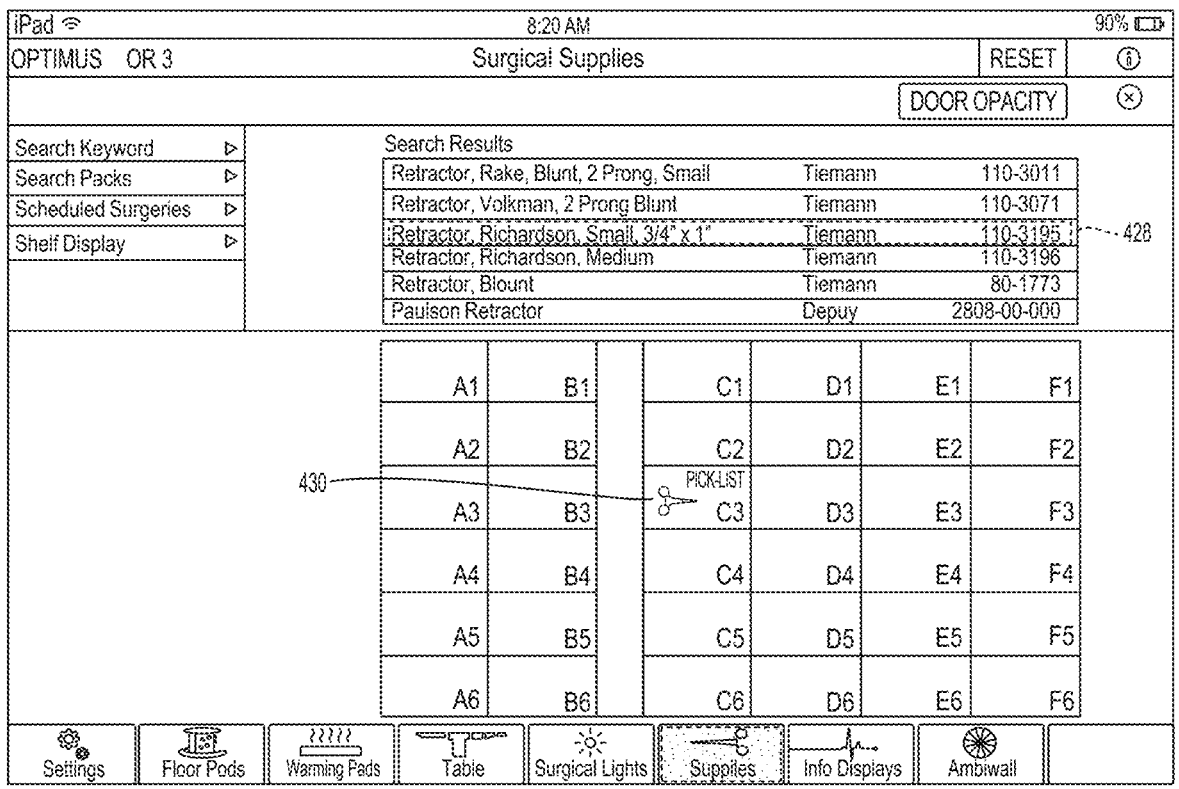
FIG. 4F shows the location of a selected supply using an icon in the two dimensional "cabinet view" array, wherein the selected supply is selected from the results shown in FIG. 4E and colored green upon selection, according to an illustrative embodiment of the invention.

As shown in FIGS. 4D and 4E, when selecting "Search Keyword," identifying criteria such as item description, product number, barcode number, or other descriptors are used to locate supplies by entering them into the entry field 424. Search criteria hints specific to the type of search may be shown beneath the entry field. The type of search selected 420 may change color (e.g., become green) to indicate what type of search is being performed. In some embodiments, selection of a search type brings up a graphical keyboard where search criteria can be entered 422. In some embodiments, a physical keyboard for providing input is connected to the wireless computing device. Tapping on the "SEARCH" button will display matching items as scrollable text in the "Search Results" panel 426. FIG. 4F shows a result of the keyword search being selected and highlighted in green 428. Upon selection, any graphical keyboard closes and the result is graphically shown in the two-dimensional "cabinet view" array 430. In this example, the result is located on shelf C3. Simultaneously, an indicator light on the physical cabinets will illuminate to show which shelf contains the item. In certain embodiments, a system comprising a plurality of cabinets distributed throughout a plurality settings in a healthcare environment is used. The location of supplies searched for by a user when a plurality cabinets are distributed throughout a plurality of settings additionally includes information identifying in which setting the supplies are located.

In certain embodiments, small surgical tools such as scalpels, forceps, retractors, for example, do not contain their own RFID tags. Their presence within the RFID Search system is known by their inclusion in packs or trays of supplies for which a contents list or pick-list exists. Therefore, the search result for such items will be a pick-list, peel-pack, or similar.

Figure 4G:
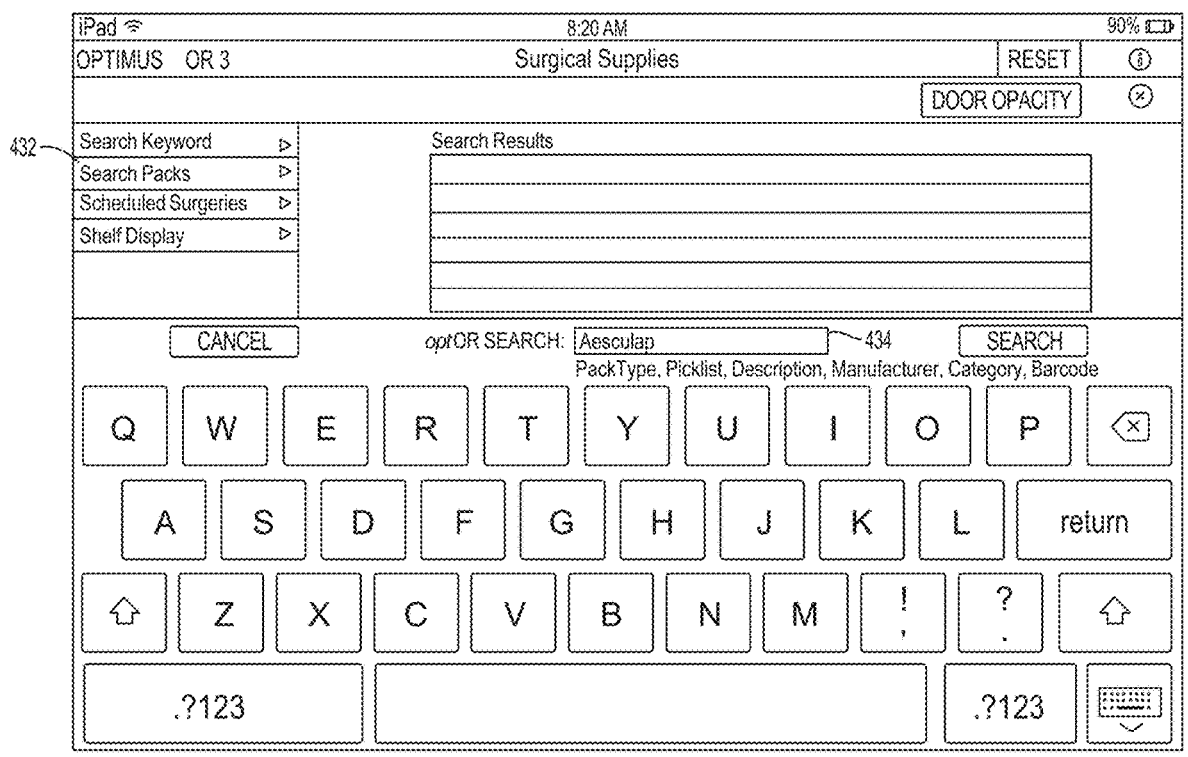
FIG. 4G shows a pack search input provided by a graphical keyboard, according to an illustrative embodiment of the invention.
Figure 4H:
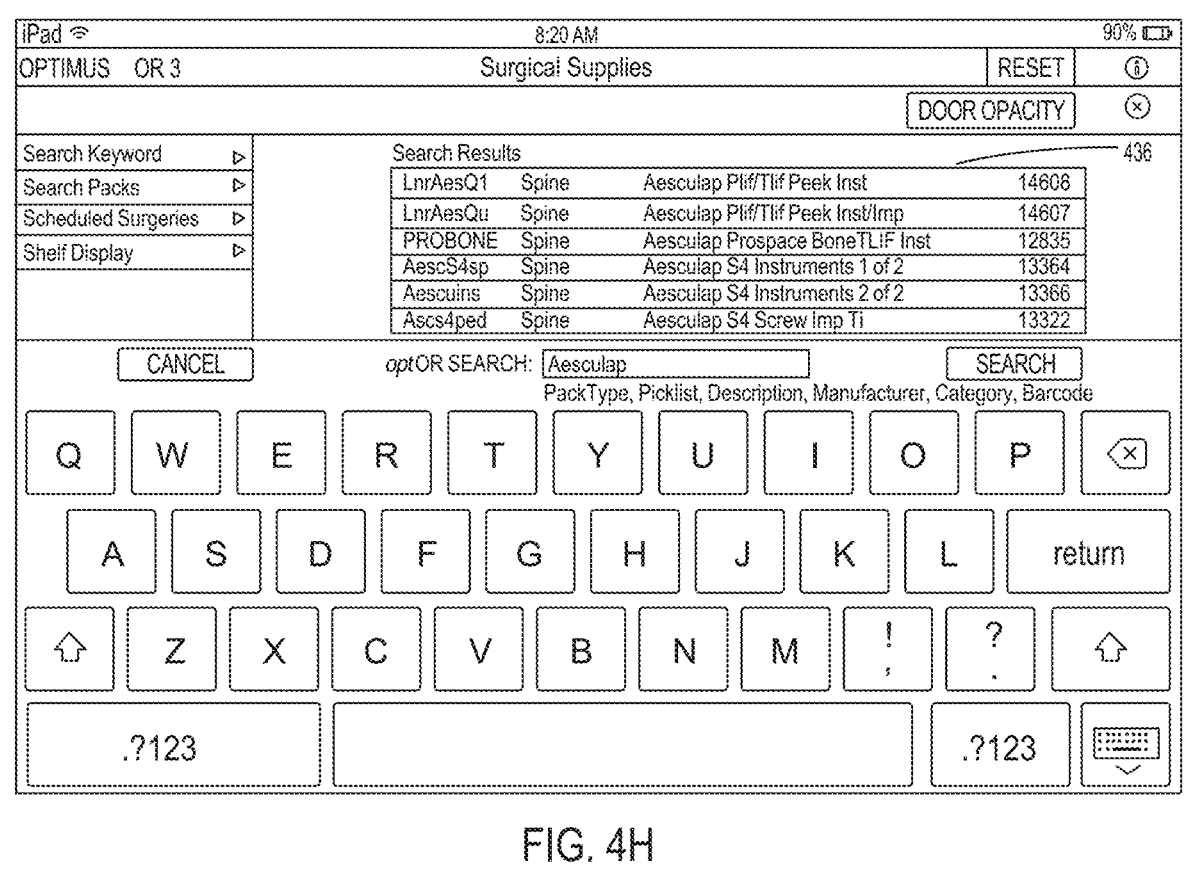
Figure 4I:
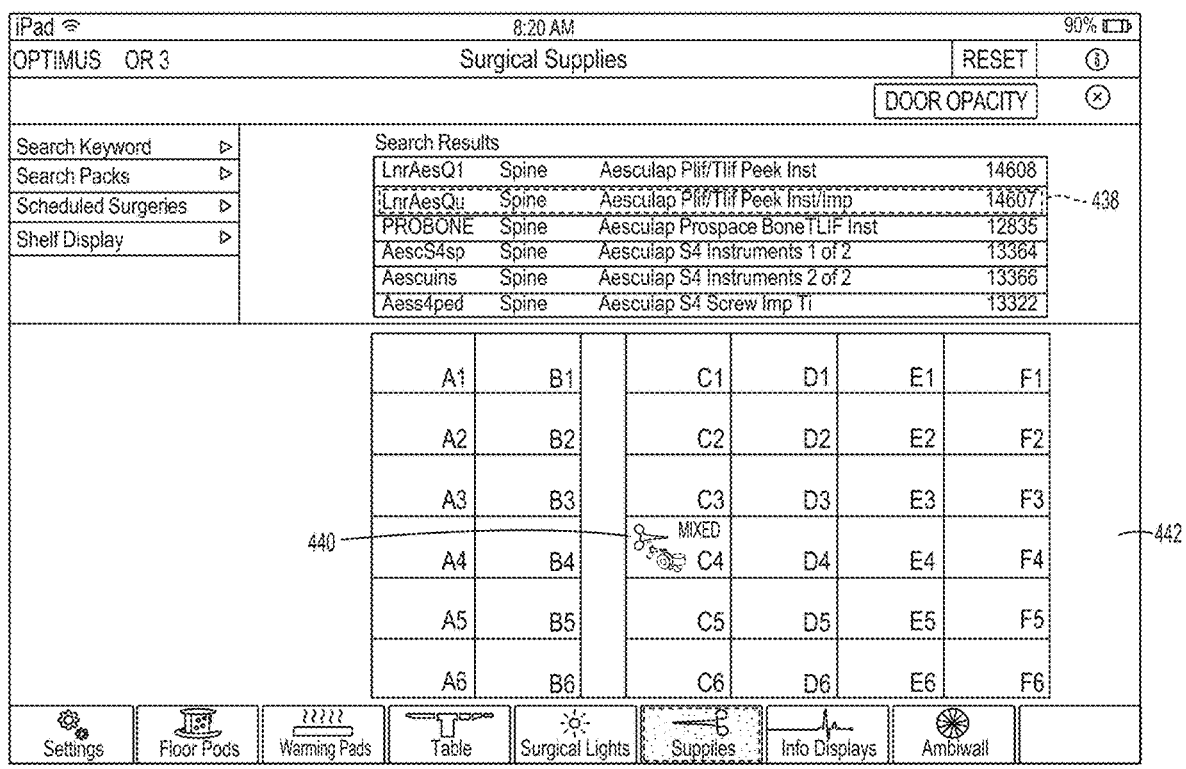
FIG. 4I shows the location of a selected pack using a "mixed" icon in the two dimensional "cabinet view" array, wherein the selected pack is selected from the results shown in FIG. 4H and colored green upon selection, according to an illustrative embodiment of the invention.

FIGS. 4G and 4H show the interface layout for initiating a "Search Packs" inquiry with the search type 432 in green and a search for "Aesculap" entered into the entry field 434. "Search Packs" is used for searches for items that are packaged together due to their similarity in function or frequent common use in a procedure, for example. Such co-packaged items may be picklists, preference cards, or trays. The user can enter search criteria such as pack type, picklist name, category, or barcode, for example, into the entry field 434 to bring up search results 436. FIG. 4I shows the graphical interface after a "Search Packs" search and subsequent selection of a surgical pack. Once the user selects the specific item 438 from within the Search Results panel, any graphical keyboard will close and the item location for the selected item 440 will be displayed in the cabinet view panel 442. If the item is in a compartment along with other supplies a "mixed" icon will appear in the cabinet grid view. Simultaneously, an indicator light on the physical cabinets will illuminate to show which compartment contain the item.

Figure 4J:
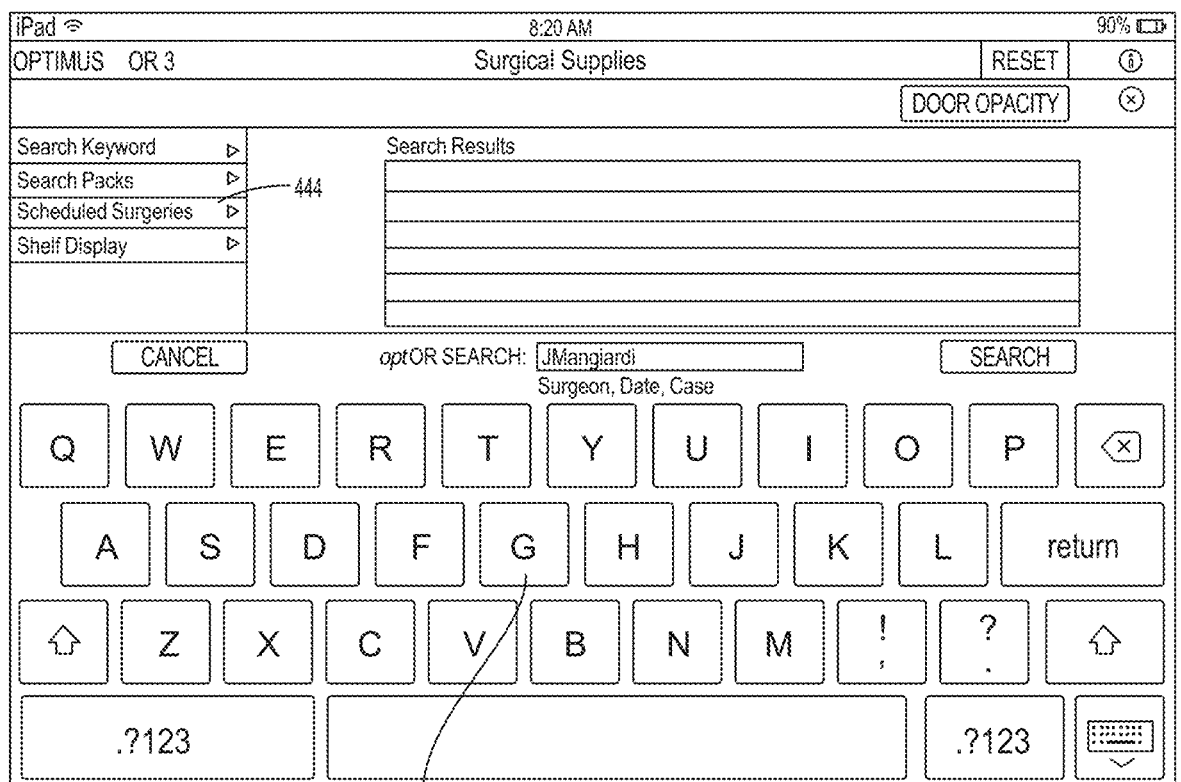
FIG. 4J shows a scheduled surgeries input provided by a graphical keyboard, according to an illustrative embodiment of the invention.
Figure 4K:
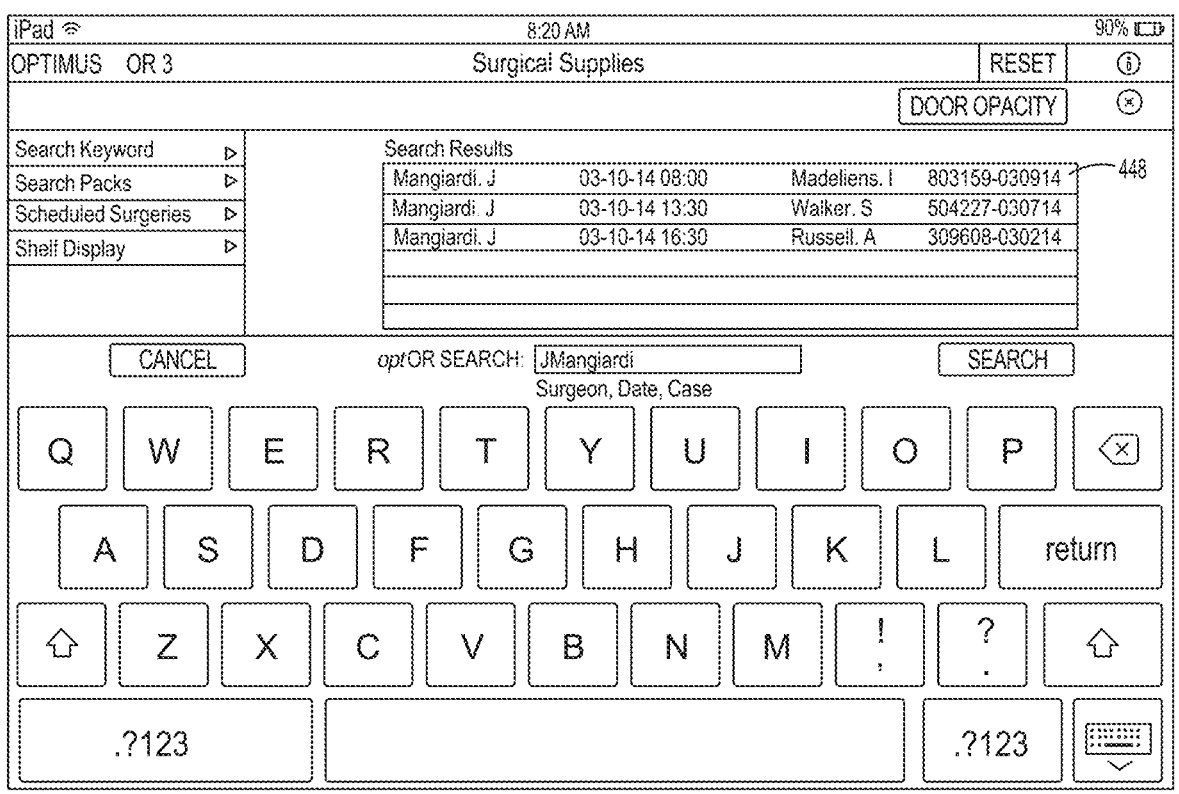
FIG. 4K shows the results of the scheduled surgeries search of FIG. 4J, according to an illustrative embodiment of the invention.
Figure 4L:
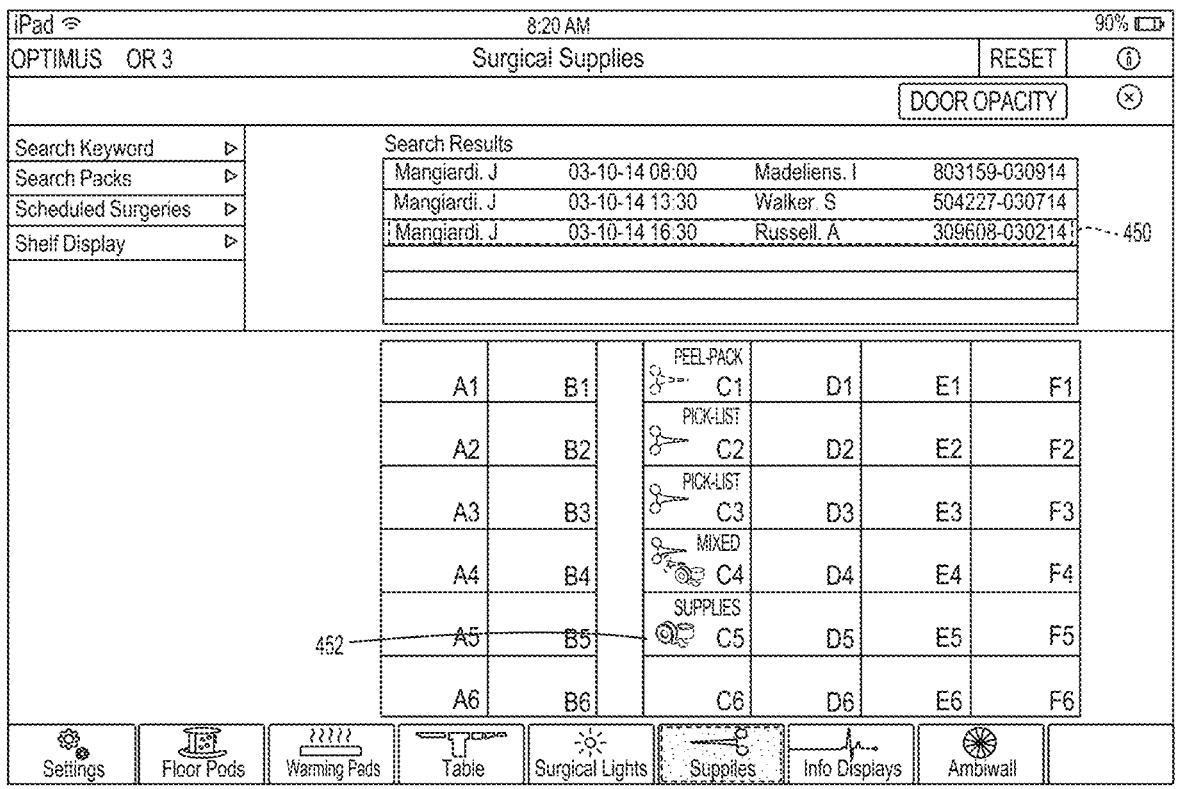
FIG. 4L shows the location of supplies relevant to the selected surgery using a icons in the two dimensional "cabinet view" array, wherein the selected surgery is selected from the results shown in FIG. 4K and colored green upon selection, according to an illustrative embodiment of the invention.

As shown in FIG. 4J and 4K, a "Scheduled Surgery" query type may be selected 444 to perform a search for all supplies related to a particular planned surgery. Search criteria entered into the entry field 446 comprises information about the surgeon or surgery such as doctor's name, date, or case number. For example, a user could search for all supplies to be used in surgeries planned by a particular surgeon in a particular operating room or all supplies to be used in that operating room on a particular day. The results show in the results panel 448. FIG. 4L shows the graphical user interface after a "Scheduled Surgeries" search and subsequent selection of a surgery, which results in a highlighted selected result 450 in the search results panel. Once the user selects the specific surgery from within the Search Results panel any graphical keyboard closes and the locations of all supplies for that surgery are displayed on a graphical grid on the UI screen. In FIG. 4L, all supplies 452 are located in the "C" cabinet on shelves 1-5. Simultaneously, indicator lights on the physical cabinets will illuminate to show which compartments contain the supplies. Color-coding of a successful search request links the original search category, in this case Scheduled Surgeries, with a highlighted search result selection and ultimately the cabinet number in the grid view. This also extends to the green indicator light on the physical cabinet.

Figure 4M:
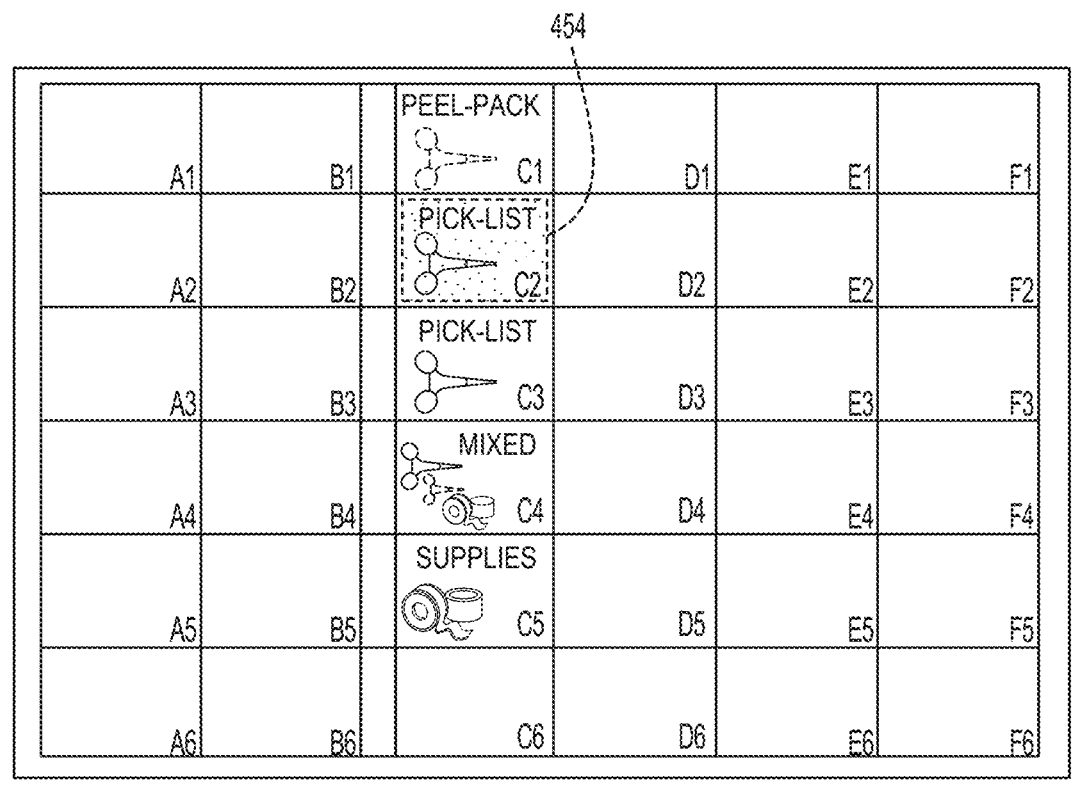
Figure 4N:
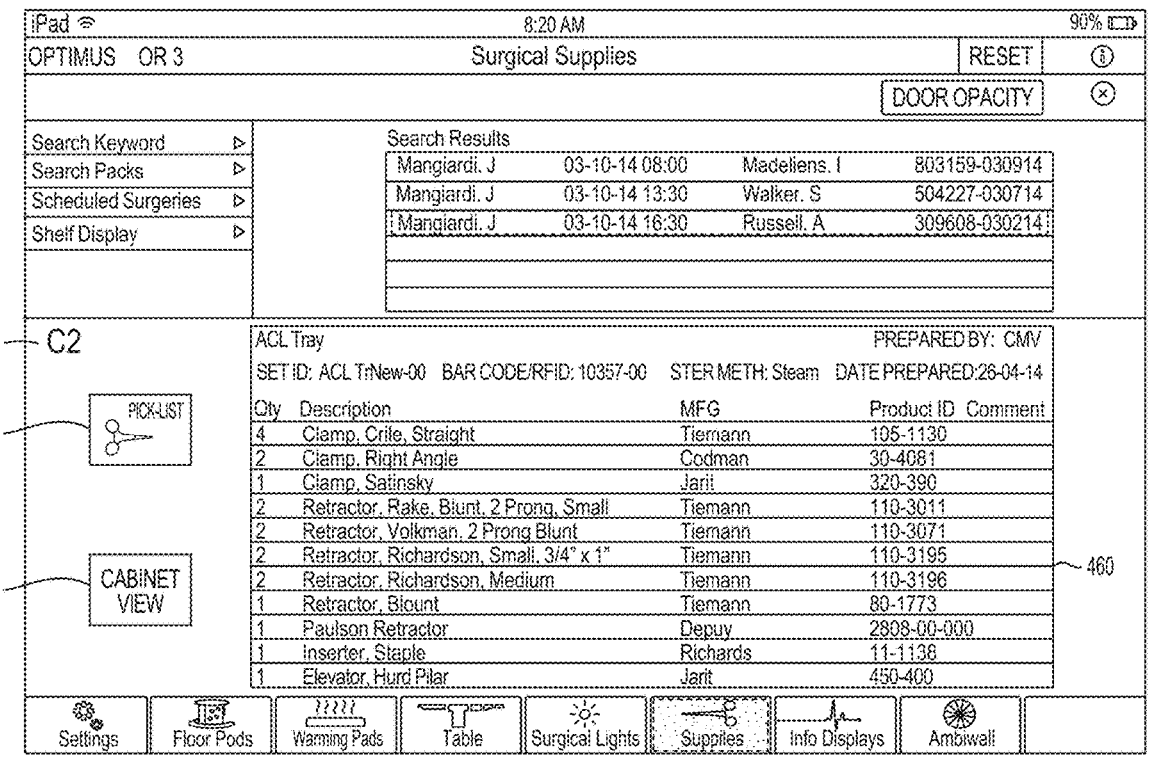
FIG. 4N shows the graphical user interface of FIG. 4M after the supply in location C2 is selected, according to an illustrative embodiment of the invention.
Figure 40:
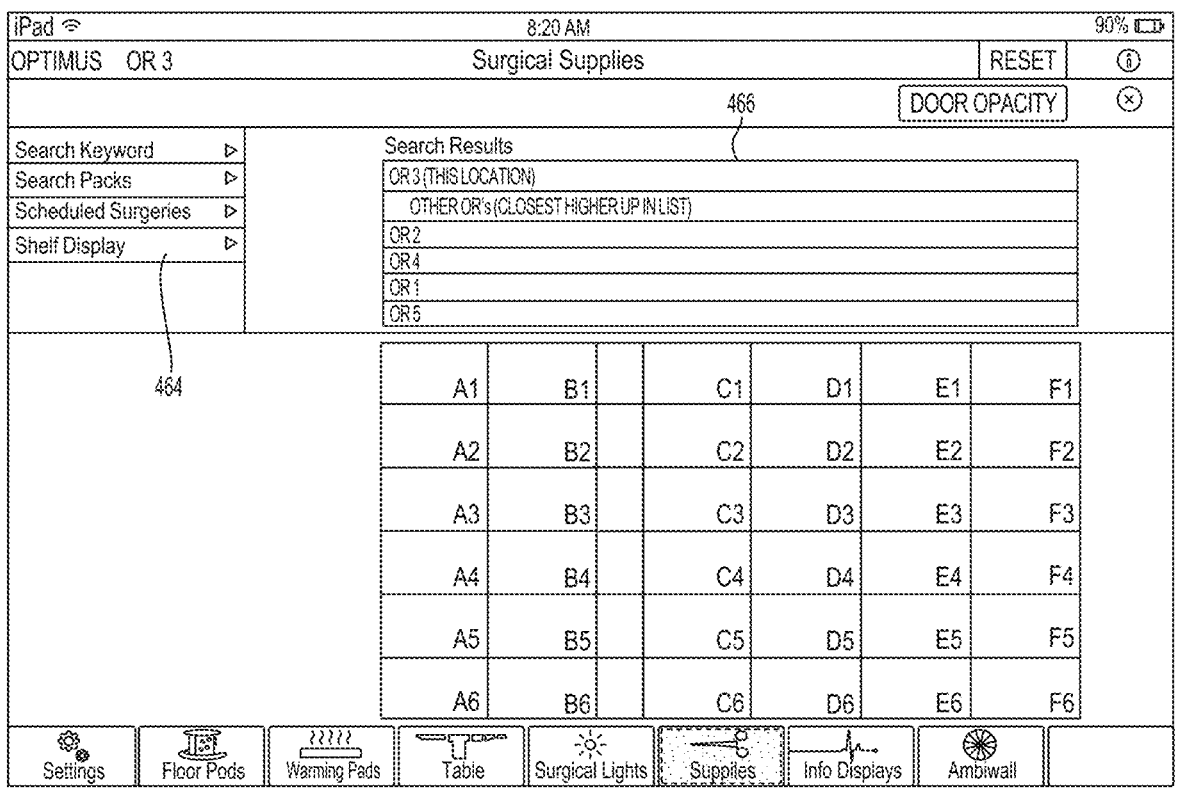

As shown in FIGS. 4M and 4N, a specific supply may be selected from the cabinet view to display details about its contents. When the results of any search are displayed within the cabinet grid view the user may tap on a specific icon to open a list of that item's contents. In the case of supply packs, a listing of each item in the pack will be provided. FIG. 4M shows a detail view of the cabinet view panel where location C2 454 is selected, causing it to be highlighted in blue. In FIG. 4N, the picklist that is located on shelf C2 has been selected, opening a list view of the picklist's contents 460. The shelf number 456 and the type of item 458 on the shelf are shown to the left of the list view for reference. The list can be scrolled within its panel to see the entire contents. In the case of a compartment with mixed contents (e.g., more than one tray or pack) the list will have a header for each individual package. If the user wants to see the contents of another package they would tap on the "Cabinet View" icon 462 to return to the cabinet view panel.

Figure 4P:
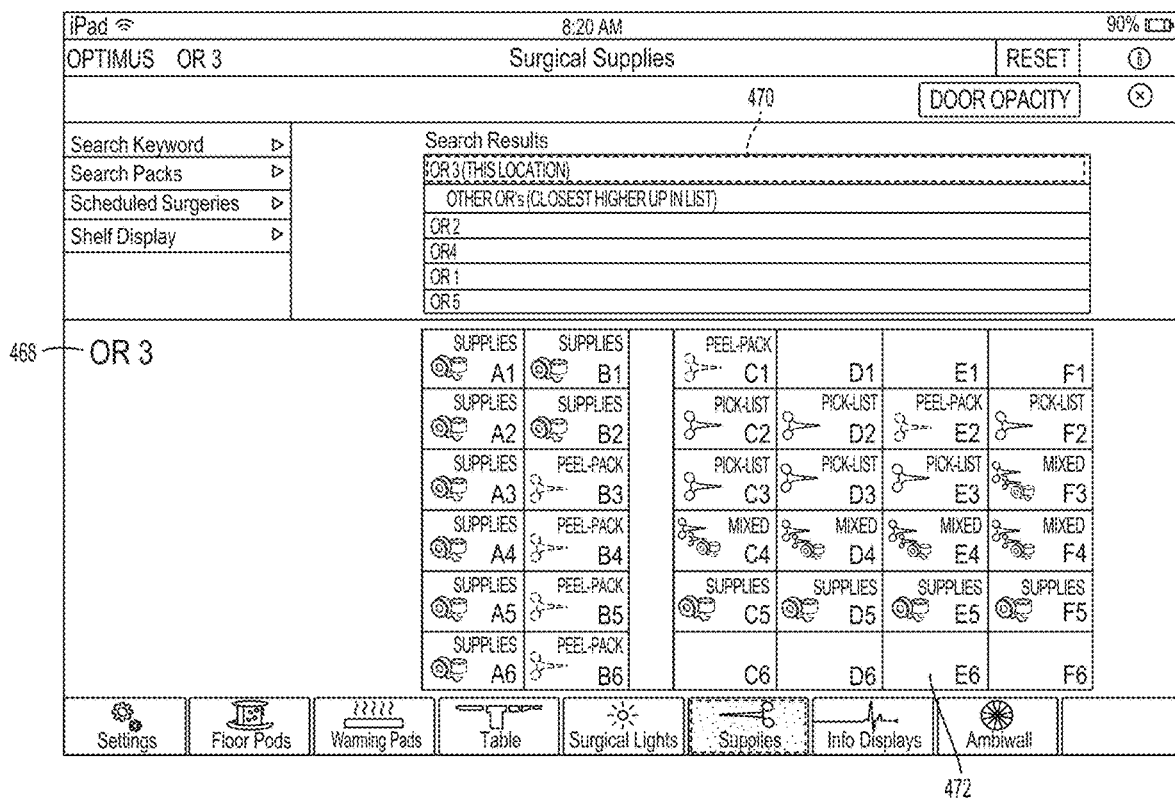
FIG. 4P shows the graphical user interface of FIG. 4O after "OR 3" has been selected from the search results panel, wherein a plurality of supplies and packs are shown in the two dimensional "cabinet view" array by a plurality of icons, according to an illustrative embodiment of the invention.
Figure 4Q:
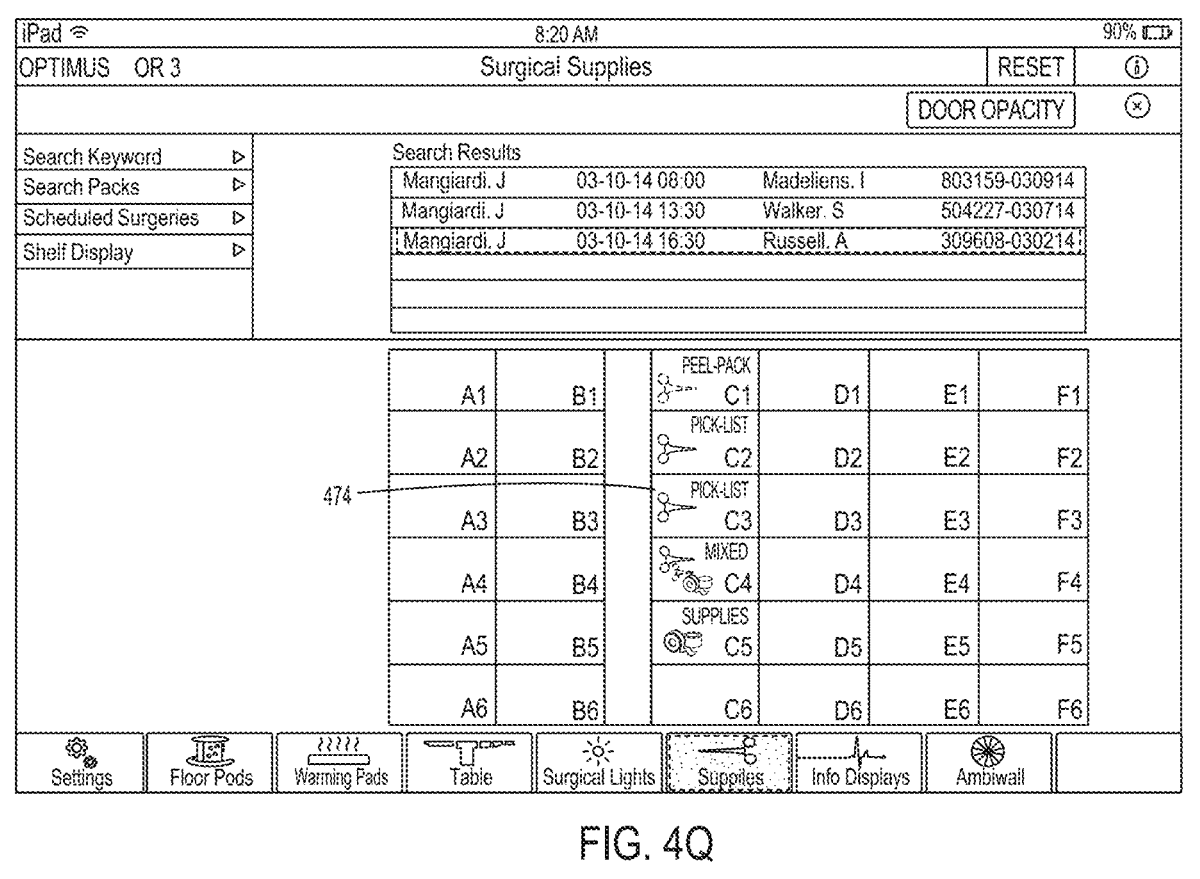
Figure 4R:
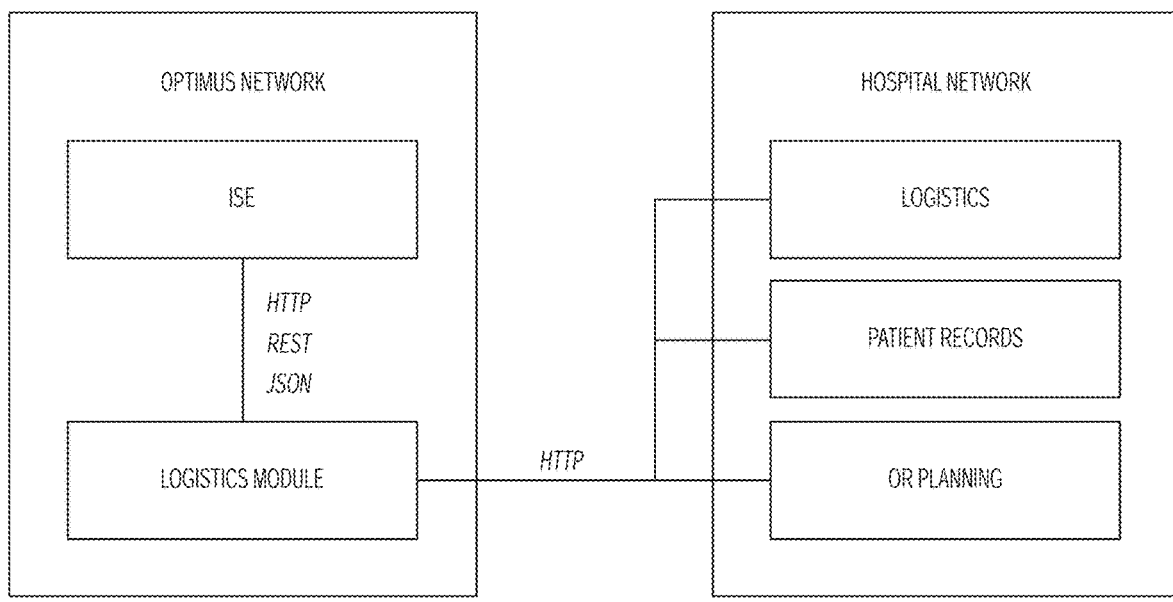
FIG. 4R shows a block diagram detailing the connection between the logistics module that is used to control the pass-through logistics cabinets of a healthcare environment and various healthcare environment information systems, according to an illustrative embodiment of the invention.
Figure 4S:
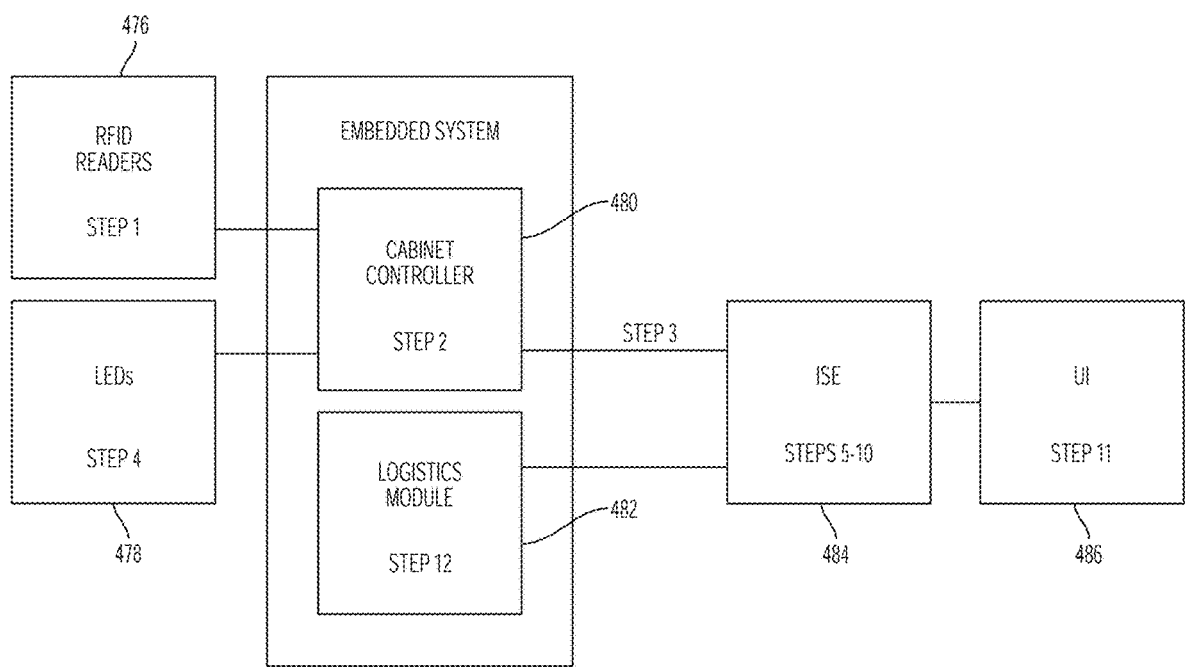
FIG. 4S shows a block diagrams demonstrating the relationship between the location sensors (e.g., RFID readers) and status indicator lights (e.g., LEDs) of a pass-through logistics cabinet, the controller and logistics module for the cabinets, the server used to control the cabinets (e.g., ISE), and its corresponding user interface, according to an illustrative embodiment of the invention.
Figure 4U:
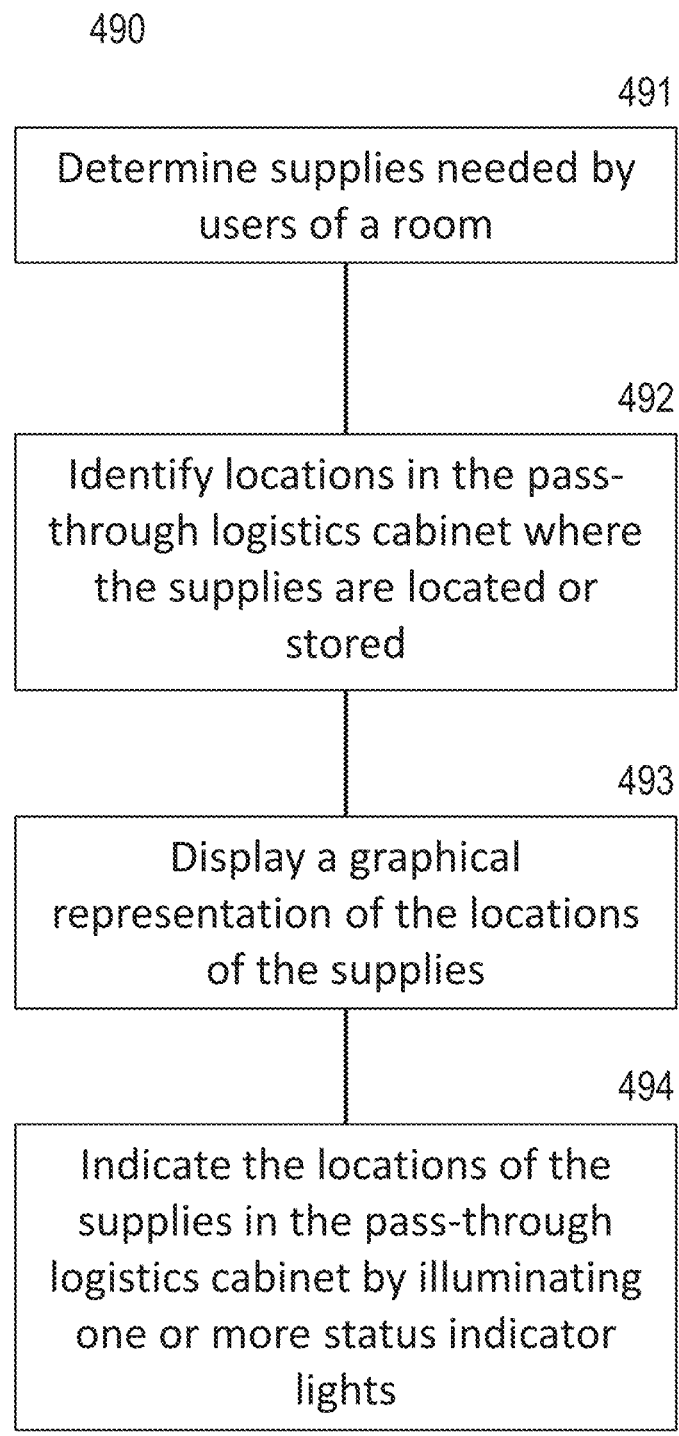
FIG. 4U shows a block diagram of a method for identifying a location to store or retrieve desired supplies in a pass-through logistics cabinet comprising one or more status indicator lights, according to an illustrative embodiment of the invention.
Figure 4V:
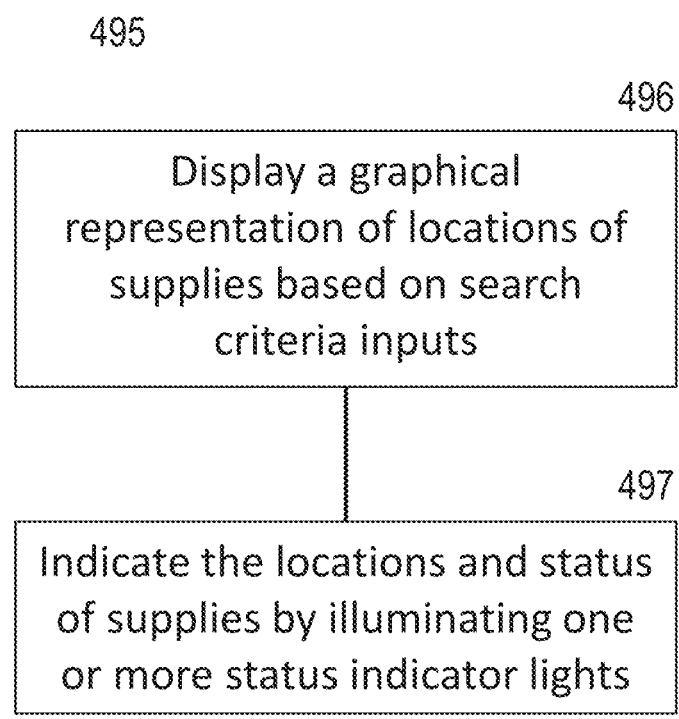
FIG. 4V shows a block diagram of a method for searching for one or more desired supplies in a pass-through logistics cabinet, according to an illustrative embodiment of the invention.

As shown in FIGS. 4O and 4P, "Shelf Display" 464 allows the user to select a setting of the healthcare environment from a list in the "Search Results" panel in order to display all shelves currently storing supplies in the cabinet view panel. As a default, the shelf display shows results for the setting in which the user is presently located. Other settings configured to run the RFID Search system are also available to select from in the search results panel. Those locations are listed by distance proximity, with those closest higher up in the search results list. A selected setting 466 is highlighted in the search results panel. All shelves storing supplies are indicated with icons 472 in the cabinet view panel. Since a "Shelf Display" search is not specific to a particular item there is no color-coding of the compartment ID numbers (e.g., C1, C2, C3) in the cabinet view panel. The selected setting for which a shelf display is being presented is displayed to the left of the cabinet view panel (Operating Room 3 ("OR 3") 468 is shown in FIG. 4P). On the physical cabinets, the blue indicator lights would illuminate to show which compartments contain supplies. Status indicator lights would only illuminate for the setting the user is in and not in any other location.

If, during a scheduled surgery search, a supply item which was requested had been delivered but then subsequently removed before that surgery, the shelf that had stored the missing item will show a red indicator in both the cabinet view panel 474 when searched for as shown in FIG. 4Q. In some embodiments, the corresponding cabinet shelf shows a red status indicator light to indicate the missing item.

Note that a wider variety of icons, which represent various categories of surgical supplies, may be utilized to indicate more specific types of supplies.

In some embodiments, preferences for functionalities of the pass-through logistics cabinets and related search interface may be modified. For example, search results identifying supplies located within the current setting may trigger illumination of corresponding cabinet shelves. Additionally, search results leading to supplies located within the present setting may trigger activation of electrochromic glass in specific cabinets causing glass to turn transparent.

In certain embodiments, a user confirms the current surgery of an operating room during login, which automatically pushes that surgery's search results to the UI so that the interface and status indicator lights mirror the actual cabinet status of one or more cabinets as it relates to the current surgery. If the user were to initiate a different search on the UI, the search would potentially result in different indicators being displayed. The user can do a Scheduled Surgeries search to bring up the supplies location result for the current surgery again. When the user or other staff, retrieves items from the cabinet compartments the RFID tracking system will report this action back to the inventory tracking database. This will change the status indicator lights in the respective cabinet compartments. In some embodiments, if supplies are removed during the normal time-slot for a scheduled surgery, then the indicator light will go off, indicating that the compartment is empty. Whereas, if the supplies are removed outside of the time-slot for the scheduled surgery, the indicator light will turn red, alerting surgical staff that supplies were requested and delivered but are now missing. A software or system crash will not initiate a reset to default mode. In particular, the status lights on the respective cabinet shelves will still indicate positive status for items belonging to a scheduled surgery in order to limit the impact of a software malfunction during a treatment or procedure.

Floor Sterilization Robot for Settings of Healthcare Environments

Typically operating room turnover time" (e.g., the time needed to change the room from an operation completed to the start of the following operation) averages approximately 39 minutes. The range for this varies from hospital to hospital, and can extend to well over an hour. The concept of fixing turnover time to under 15 minutes on a consistent basis is one that fulfills design criteria for "efficiency by design." Another issue is the standard re-use of cleaning devices, such as hand cloths, swipes, mops and others, to clean the room manually between operations, without any sterilization of the devices. Previous separate embodiment of this concept is outlined in U.S. Pat. No. 8,127,396, utilizing sterile disposable cartridges.

In certain embodiments, described herein is a robotic floor cleaner used to sterilize the floor of a setting using cleaning pads and follow-on swipe device using a combination of hot (e.g., 90 degrees centigrade) disposable water and direct ultraviolet light, respectively. In certain embodiments, the robot comprises a positioning laser or other sensor device, drive motors, a battery, wheels, control, a wastewater tank, a freshwater tank, an obstacle laser, cleaning pads, and a UV light.

Figure 5A:
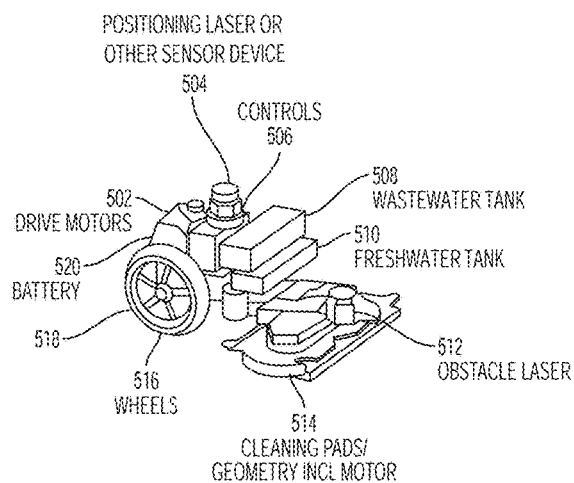
FIG. 5A shows a floor cleaning and sterilization robot for sterilization of a floor of a healthcare setting, wherein the robot comprises drive motors, a positioning laser, controls, a wastewater tank, a freshwater tank, a battery, wheels, an obstacle laser (for avoiding obstacles on the floor), and cleaning pads, according to an illustrative embodiment of the invention.

FIG. 5A shows an illustrative embodiment of a floor cleaning and sterilization robot. In some embodiments, the robot can clean and sterilize the floor of an approximately 80 square meter setting in approximately 12 minutes.

The battery 520, drive motors 502, positioning laser or other sensor device 504, wheels 516, controls 506, and obstacle laser 512 are used to maneuver the robot throughout a healthcare setting. The positioning laser or other similar sensor is used for the robot to locate itself within the setting in order to precisely follow a path throughout the room. In certain embodiments, the path is preplanned using a wireless computing device and relayed to the robot from a server after which the positioning laser and controls maintain the robot on the path. In some embodiments, the positioning laser or other sensor device and controls are able to analyze the room and then determine the an optimal path for the robot to follow. The obstacle laser is used for rerouting the robot in the case that unexpected obstacles are present in the setting that must be navigated around. In some embodiments, software allows for the robot to recognize the layout of an individual room (e.g., size, fixed obstructions, flooring characteristics). Such software may be configurable to allow the unit to plot the most efficient algorithm in order to minimize the time-to-clean.

Figure 5B:
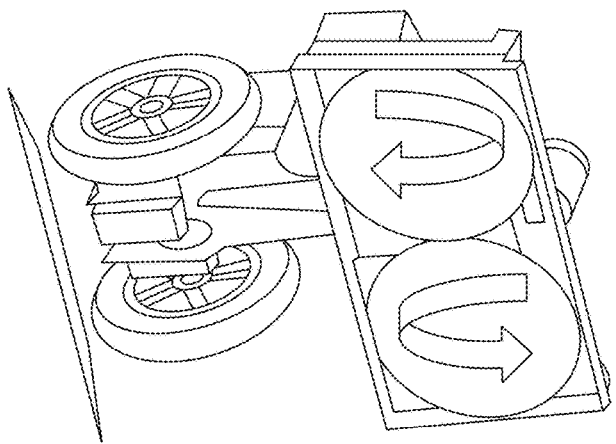
FIG. 5B shows a bottom view of the robot of FIG. 5A with arrows indicating the direction of motion of the cleaning pads when in use, according to an illustrative embodiment of the invention.

The battery 520, cleaning pads 514, wastewater tank 508, freshwater tank 510, controls 506, follow-on squeegee 518, and optional UV light (not shown) are used to clean and sterilize the floor. The freshwater tank holds a cleaning fluid used with the cleaning pads to clean the floor. The cleaning fluid may be hot (e.g., >90° C.) water, an anti-bacterial chemical, or other similar anti-microbial fluid. Fluid is released onto the floor in proximity to the cleaning pads, which rotate to apply rotational forces to clean the floor, as graphically shown in FIG. 5B. Used fluid is pulled from the floor up into the wastewater tank as the robot moves across the floor. A follow-on squeegee may be used to capture loose fluid on the floor before the fluid is pulled into the wastewater tank using a suction device. A UV light may be optionally mounted behind the cleaning pads, relative to the direction of travel, for additional sterilization after cleaning. In certain embodiments, the UV light interacts with the cleaning fluid (e.g., a residual film of cleaning fluid) to sterilize the floor faster than by UV light alone.

Figure 5C:
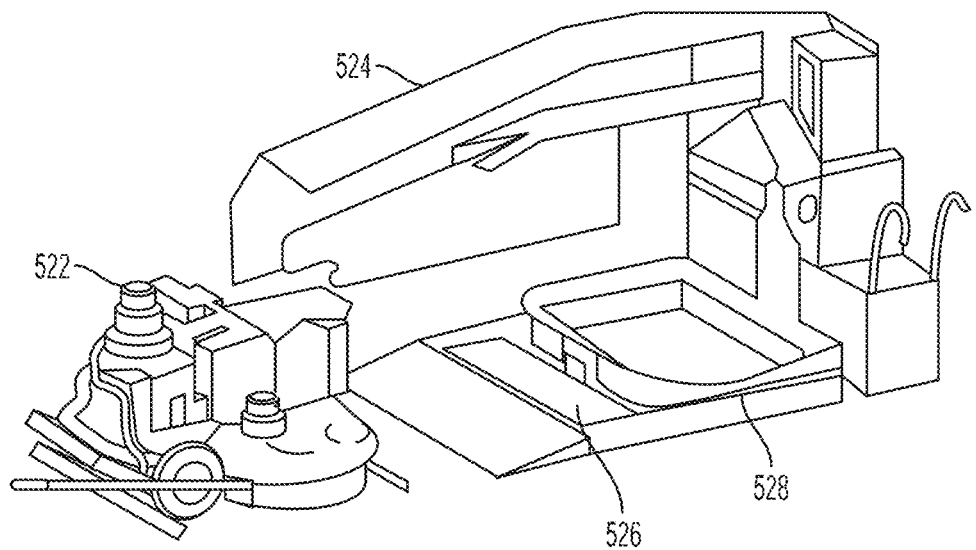
FIG. 5C shows a schematic of an in-wall garage for storing a floor cleaning and sterilization robot, wherein the garage is capable of sterilizing the cleaning pads, removing and replenishing cleaning fluids, and exchanging the robot's battery, according to an illustrative embodiment of the invention.

After cleaning and/or sterilizing the floor of the setting, the robot can return to a configurable recharging, restocking and sterilization garage. FIG. 5C shows an illustrative embodiment of such a garage 524. In some embodiments, the garage is located between an interior and exterior wall of a setting in order to maximize the useable space of the setting. The configurable garage unit automatically performs one or more of several functions when the robot is docked inside.

Figure 5D:
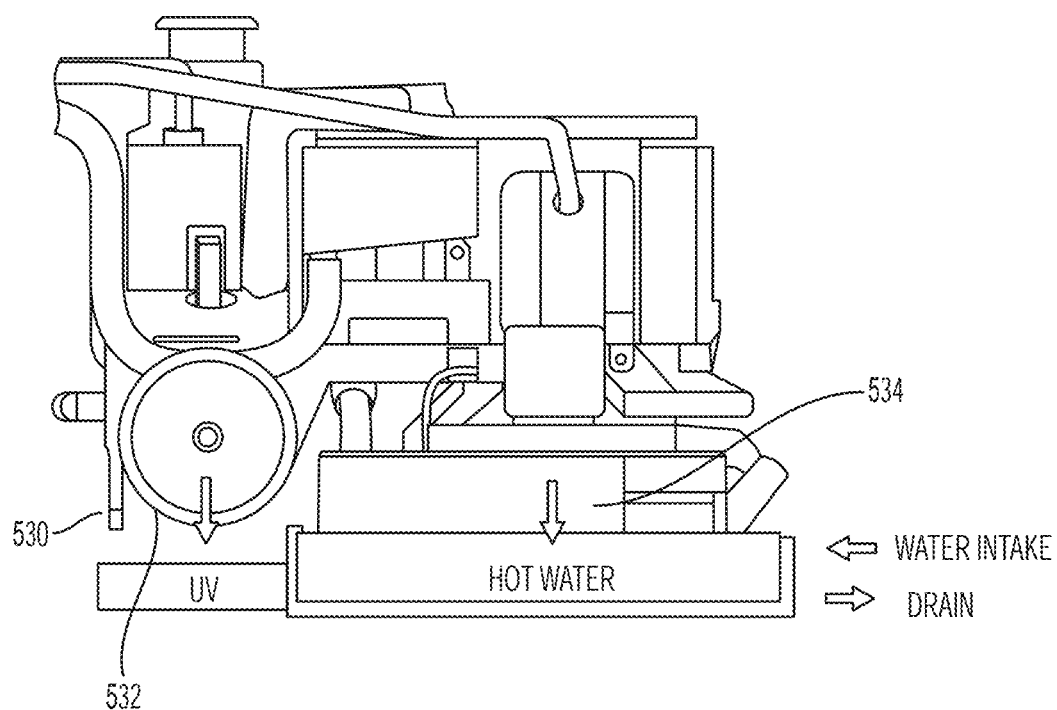
FIG. 5D shows a schematic of the process for sterilizing a robot when parked in a garage, according to an illustrative embodiment of the invention.
Figure 5E:
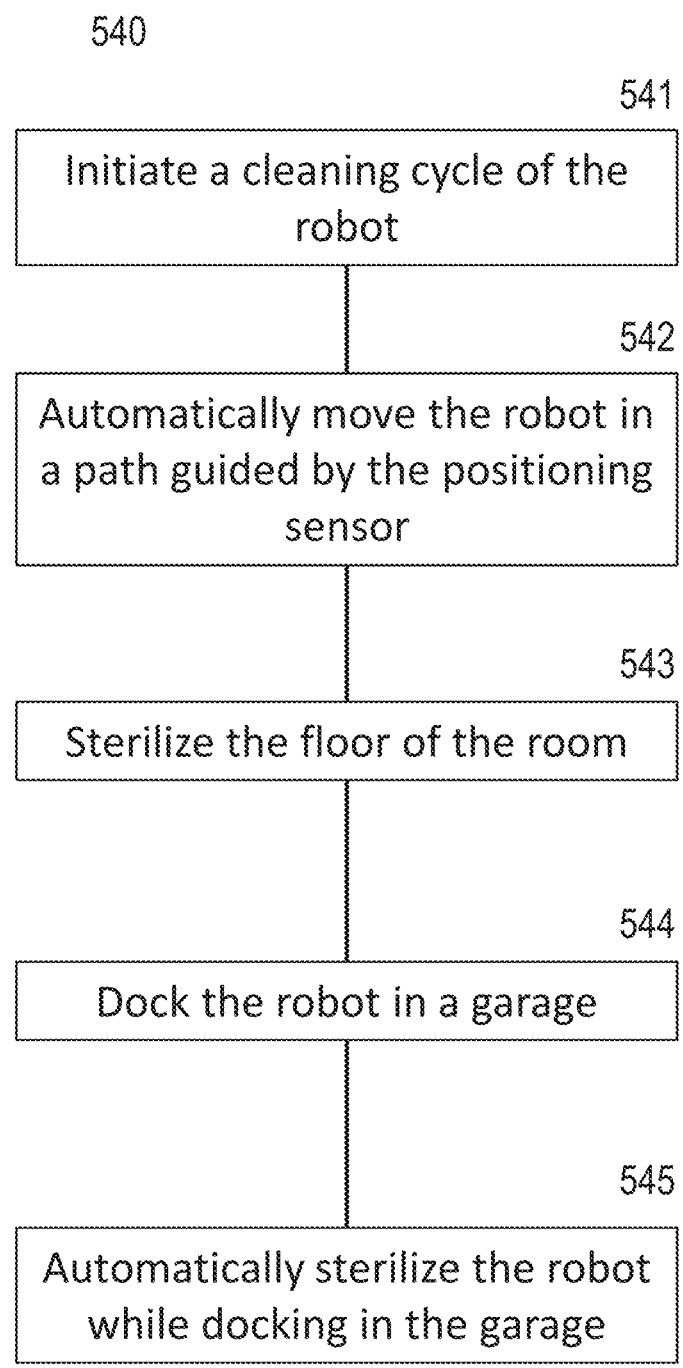
FIG. 5E shows a block diagram of a method of using a floor cleaning robot to sterilize a floor of a room in a healthcare environment, according to an illustrative embodiment of the invention.

The robot's battery may be recharged or replaced with a charged battery. The cleaning pads and follow-on squeegee may be sterilized to inhibit the spread of contaminants on the robot 522 present after a cleaning cycle in future cleaning cycles. The sterilization of the pads is done by immersion in hot (e.g., 90° C.) water in a basin 528. In certain embodiments, the cleaning pads are sterilized by immersion in a 90 degree water bath for 20 minutes. A UV light 526 is additionally utilized for sterilization of the robot cleaning surfaces and/or drive components that contact the floor (e.g., the wheels). The fluids in the freshwater and wastewater tanks may be replenished, replaced, and/or drained. For example, the wastewater tank may be drained while fluid is added to the freshwater tank until it is full. In certain embodiments, automatically the battery is recharged, the cleaning pads are sterilized using hot water, the follow-on squeegee is sterilized using a UV light, and fluids are drained and replaced when the robot docks in the garage. FIG. 5D shows a side view of the robot 522 parked in the garage 524 where the follow-on squeegee 530 and wheels 532 are sterilized using the UV light and the cleaning pads 534 are sterilized using hot water. The garage can be configured for best solutions for various floor surfaces, and volumes of cleaning fluids and aqueous solutions for a particular room size and configuration.

Integrated Control of Room Components, Systems, and Medical Equipment in a Healthcare Setting While a number of medical device and audiovisual companies offer partial integrations solutions for the management of proprietary single devices (e.g. endoscopic surgical equipment) and management of in-room audiovisual devices, such as controllers, video management units and processing systems, as well as video recording and signal modification devices, none has developed a solution that will allow for the control of all devices, including medical devices, in an operating room. The net result has been an increase in the number of video displays (up to 8 per room), audiovisual management devices and complexity of both variety of devices and number of manufacturers' user interfaces. The amount of clutter accumulates, line-of-site is limited, and the number of potential systems failure events increases. Finally, because there is no standardization of medical user interfaces (MUI) and non-medical user interfaces in the modern operating room, the number of risk events for MUI errors increases proportionately.

A significant obstacle to holistic integration of an operating room, and the various devices utilized within it, is the insistence of medical device companies upon maintaining proprietary control of their user interfaces, look-and-feel, and control software. Also, a big disincentive to change medical user interfaces (MUI), application programming interfaces (APIs) and/or communications protocols, is that each company that offers an integration solution for its own medical devices (e.g. endoscopy devices and audio/video units) is required to recertify and undergo a repeat certification audit (the larger the company, the longer it takes both in time and cost) for its integration software every time a new device, MUI or functionality is introduced.

In some embodiments, described herein is a control system for controlling all electronic and electromechanical components of a healthcare setting (e.g., all of the electronic and electromechanical components disclosed herein) using a custom operating software. In some embodiments, a server comprising the custom operating software is used as a central communication hub. A non-exhaustive list of components and systems that may be controlled by the control system includes:

Medical devices (both proprietary and any $3^{rd}$ party devices)

Electromechanical devices (e.g., robotic floor cleaner, ozone sterilization system, ambient lighting solutions etc.)

Healthcare environment information systems ("HIS")

Radiology picture archiving and communications systems ("PACS")

Audiovisual displays, control systems and conferencing systems

HVAC (e.g., air conditioning, heating and humidity controls)

Figure 6A:
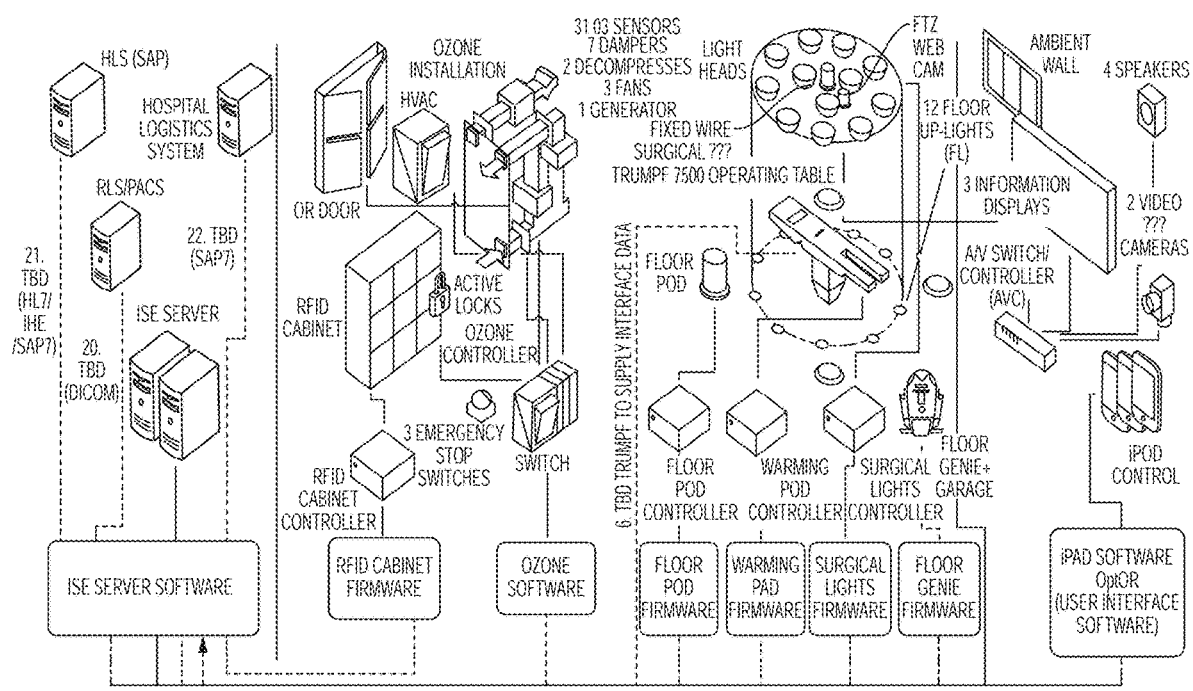
FIG. 6A shows a schematic diagram of the systems and components that can be controlled by a common server that integrates with pre-existing healthcare information systems of a healthcare environment, according to an illustrative embodiment of the invention.

The components described herein may be connected to a common control system (e.g., a central server or control software). As shown in FIG. 6A, several major components of an integrated operating room are connected to the control server (the "ISE Server") using the ISE Server Software. The "Ozone Installation" ozone sterilization system, comprising 32 ozone sensors, 7 dampers, 2 decomposers, 3 fans, and 1 generator, connects to the Ozone Controller running Ozone Software that communicates with the ISE Server Software through a plurality of switches. The RFID Cabinet connects to the RFID Cabinet Controller running RFID Cabinet Firmware that communicates with the ISE Server Software. One or more Floor Pods are connected to the Floor Pod Controller running Floor Pod Firmware that connects with the ISE Server Software. The Trumpf 7500 Operating Table comprises firmware that interfaces directly with the ISE Server Software. A patient warming pad system on the operating table connects to the Warming Pad Controller running the Warming Pad Firmware that communicates with the ISE Server Software. The integrated lighting and air plenum ("Light Heads") comprising a surgical light camera and web cam and a plurality of surgical lights connects to the Surgical Lights Controller running the Surgical Lights Firmware that communicates with the ISE Server Software. The Floor Genie and Garage run the Floor Genie Firmware that communicates with the ISE Server Software. The general audiovisual components such as 3 Information Displays, Ambient Walls comprising backlights, 4 Speakers, 2 Video Conference Cameras, and 32 Floor Up-Lights connect to an A/V Switch/Controller (AVC) that communicates with the ISE Server Software. The wireless computing devices (i.e., iPods™) run User Interface Software that communicates with the ISE Server Software such that all the other connected components may be controlled using the wireless computing devices. The ISE Server Software is additionally connected to external systems such as the Hospital Logistics System, HIS, and PACS. Other embodiments may comprise components and systems connected to a central control server in different arrangements or using different protocols than schematically represented in FIG. 6A. In some embodiments, components are controlled without the use of a central server. For example, a user interface software may be configured to communicate directly with each component or system.

Figure 6B:
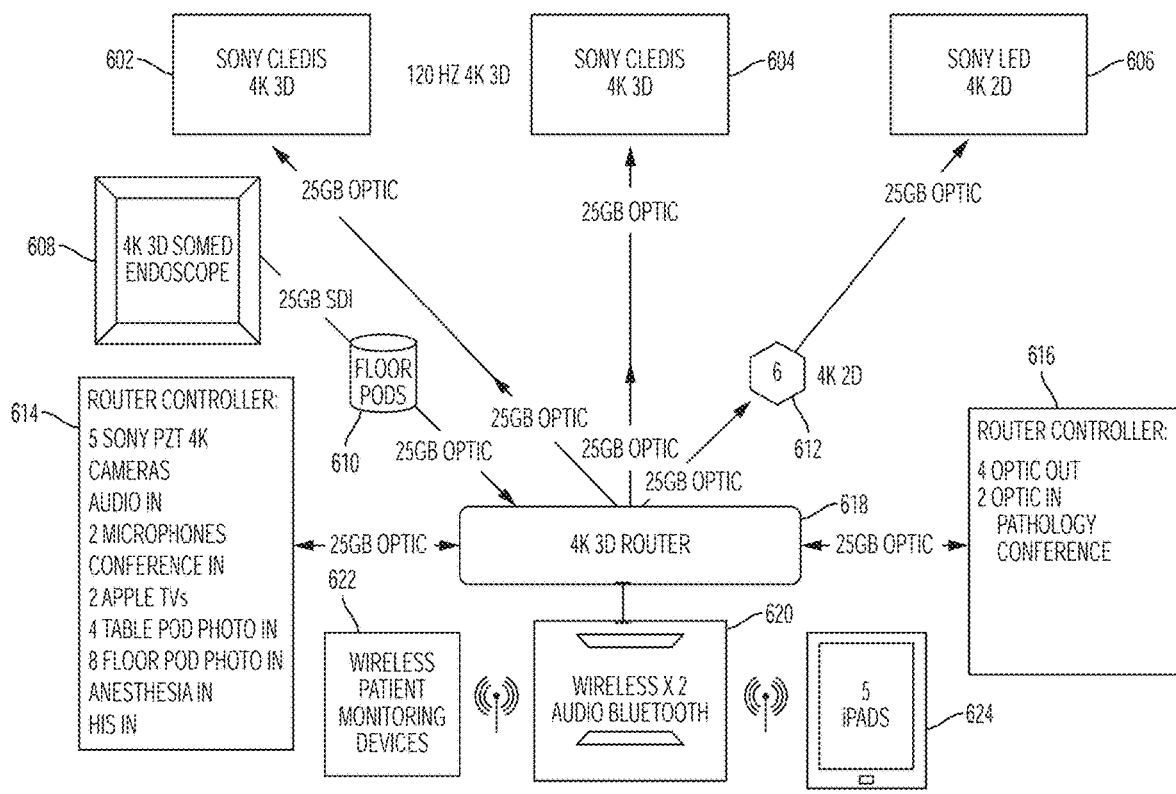
FIG. 6B shows a block diagram of a system for displaying video or data feeds transmitted and received from several systems and components of a setting and its healthcare environment across three 4K HD monitors, according to an illustrative embodiment of the invention.

FIG. 6B is a block diagram showing connections between the audiovisual components of an integrated setting according to an illustrative embodiment. Three high definition (i.e., 4K) 3D monitors 602-606 are connected to, sometimes via 4K 3D splitters 612, a 4K 3D Router 618. In some embodiments, there may be more or less monitors, more or less splitters, and/or more or less routers. In certain embodiments, the number of the number of monitors is the same as the number of splitters in the system. The router routes a plurality of input medical data feeds to at least one of the splitters such that each splitter combines the medical data feeds received as input into one data output feed that is displayed on the connected monitor. Use of the router 618 and splitters 612 allows up to 6 different video or data feeds to be displayed on each of the 4K 3D monitors 602-606 for a total of up to 18 unique feeds being displayed simultaneously. In some embodiments, the number of feeds able to be simultaneously displayed may be higher or lower.

The 4K 3D router 618 receives and transmits data between a number of systems also present in the integrated setting of FIG. 6B. Router Controller 614 provides interfaces with 4K 3D router 618 to receive and transmit data or video feeds between 5 4K cameras, an audio in line, 2 microphones, a conference in line, 2 Apple TVs, an anesthesia in data feed, 5 iPad™ mirror in feeds, and an HIS in feed and the 4K 3D monitors 602-606. A separate router controller 616 provides additional interfaces with 4K 3D router 618 to receive pathology and conference data feeds and transmit data via 4 SDI out feeds. The 4K 3D router 618 is additionally indirectly connected to a 4K 3D endoscope 608 via a floor equipment 610 in order to transmit a video feed to one or more of the 4K 3D monitors 602-606 during endoscopic procedures. All of the audiovisual components shown in FIG. 6B interface using 25 GB optical transceiver. Other equivalent interfaces known in the art may be used. In some embodiments, the 4K 3D router 618 connects to an audiovisual controller that connects to a control system (e.g., by the "ISE Server Software" in FIG. 6A). In some embodiments, the 4K 3D router 618 connects directly to the control system. A 4K 3D router may receive and transmit through one or more router controllers all possible video and data feeds from the components and systems of an integrated healthcare setting and its healthcare environment or it may receive and transmit only a preferred subset of video and data feeds. In some embodiments, the 4k 3D router 618 connects to an appropriate wireless technologies 620 that connects to multiple wireless patient monitoring devices 622-624. In some embodiments a wireless technology is Bluetooth, Wifi, Bluetooth Low Energy (BLE), and so forth. Other equivalent wireless technologies known in the art may be used.

In certain embodiments, the control system comprises a software integration package that is capable of integrating all medical devices without requiring medical device vendors to modify their proprietary software to be able to be controlled by the system. The software integration package uses a generalized software, referred to herein as the Operating Room Integration Model (ORIM), as its core component. The ORIM stands alone, and does not change when a new medical device is introduced in a particular class. The same is true for non-medical devices, such as electromechanical systems, logistics systems, healthcare environment information systems (HIS), HVAC, for example. In this sense the ORIM software is vendor agnostic as there is no need to modify existing proprietary MUI, API's or communication protocols in order to integrate new devices from a 3$^{rd}$ party vendor.

On either side of the ORIM are the user interface on the input side, and the medical device on the output side. Each of these is tied to the ORIM by a VMB (View Model Bridge) and an ODB (ORIM Device Bridge), respectively. In certain embodiments, all communication from the user interface and the device works through the ORIM, both to and from the device, so that both the VMB and ODB are standardized to the logic of the ORIM.

On the user interface side, the standard logic of the VMB allows for standardization of medical user interfaces. The differences between MUIs from different vendors are a growing cause for medical errors in the operating room space, as devices and their user interfaces proliferate both in number and complexity. Using a standardized MUI provides clarity to medical staff on the inputs they are providing to medical equipment without requiring the staff to acclimate themselves to the particular equipment being used (and controlled using the MUI). For example, errors that result from misinterpreting or misremembering what happens when an "up" icon, "down" icon, "left" icon, or "right" icon are selected for a particular piece of equipment are eliminated if "up," "down," "left," and "right" are always represent the same action and are selected in the same way. If a vendor's equipment uses a different convention, the standardized interface will be mapped to the vendor's convention for proper communication.

In certain embodiments, a tool is provided that gives the manufacturer the ability to maintain their MUI, APIs and communication software protocols without modification for use in the software integration package, referred to herein as the Device Bridge Tool (DBT). The device bridge tool acts as an ODB software generator. The DBT uses a user interface comprising a dropdown menu of questions that pertain to the class of device that is to be controlled, and the type of communications protocol that the medical or other device manufacturer uses to typically communicate with their proprietary MUI or other user interface modality. Once the ODB has organized the software protocols for communication, the VBM can be modified by an end user technician to comply with the standardized MUI or UI protocols established in the ISE design directives.

Figure 6C:
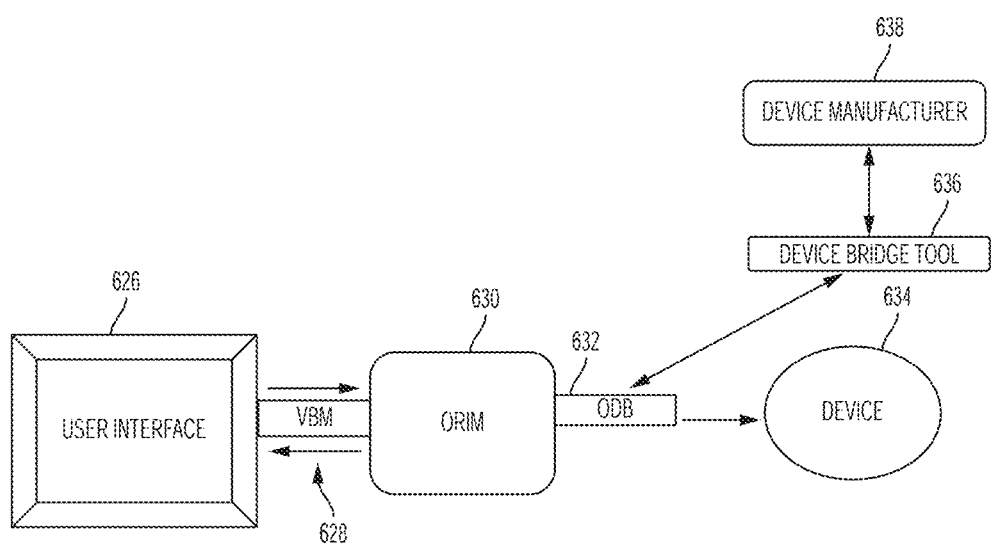
FIG. 6C shows a block diagram of the communication modules that allow a medical device or medical equipment to be controlled by a standardized user interface regardless of the vendor of the device or equipment, according to an illustrative embodiment of the invention.

A block diagram of the interaction between the user interface, VBM, ORIM, ODB, and DBT in allowing a user to control a medical device made by any vendor is shown in FIG. 6C. The VBM 628 standardizes communication between a graphical user interface 626 and the ORIM software 630 using a standardized MUI. The ODB 632 allows the ORIM 630 to communicate with medical devices regardless of the particular API that may be used by a vendor in the software or firmware of their device. When integrating new devices into a setting controlled by the control system, the DBT 636 is used to generate an appropriate module within the ODB that allows the new device 634 to communicate properly with ORIM 630. The ODB module is generated based on device manufacturer information 638 supplied by a user.

In some embodiments, the control server comprises a plurality of different server states (e.g., operational state, systems configuration state, systems testing state). These server states can be used to limit some functionalities of the system control for various purposes. For example, when testing the system, many functionalities of the components should remain operational, while some should be inhibited. During testing, the ozone sterilization system can be tested by checking the functionality of the sensors, dampers, and other relevant parts. However, the ability of the ozone generator to produce ozone may be inhibited. As another example, during a configuration state, functionalities related to physically moving one of the components (e.g., raising and lowering a floor pod) may be inhibited.

Figure 7:
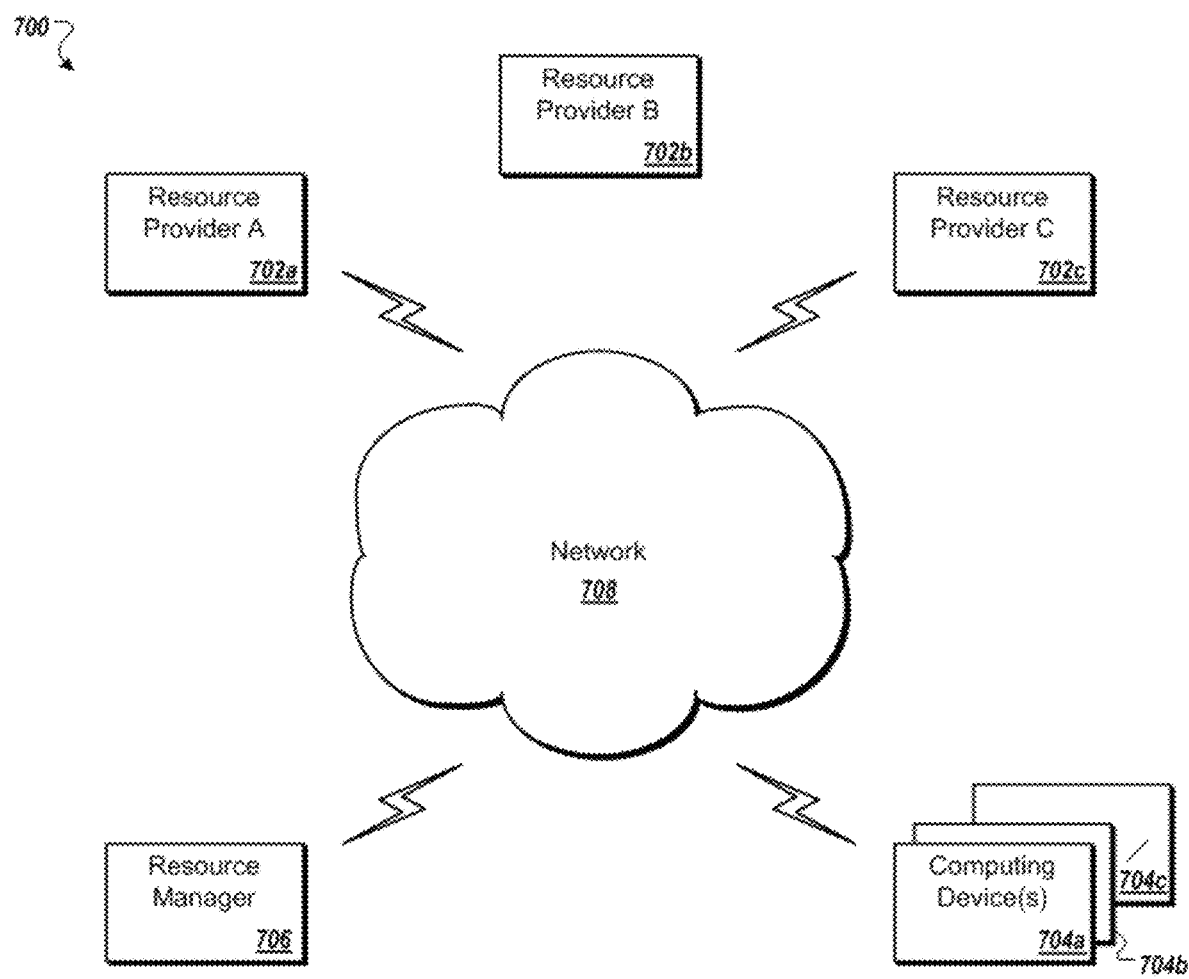
FIG. 7 is a block diagram of an example network environment for use in the methods and systems described herein, according to an illustrative embodiment.

FIG. 7 shows an illustrative network environment 700 for use in the methods and systems described herein. In brief overview, referring now to FIG. 7, a block diagram of an exemplary cloud computing environment 700 is shown and described. The cloud computing environment 700 may include one or more resource providers 702a, 702b, 702c (collectively, 702). Each resource provider 702 may include computing resources. In some implementations, computing resources may include any hardware and/or software used to process data. For example, computing resources may include hardware and/or software capable of executing algorithms, computer programs, and/or computer applications. In some implementations, exemplary computing resources may include application servers and/or databases with storage and retrieval capabilities. Each resource provider 702 may be connected to any other resource provider 702 in the cloud computing environment 700. In some implementations, the resource providers 702 may be connected over a computer network 708. Each resource provider 702 may be connected to one or more computing device 704a, 704b, 704c (collectively, 704), over the computer network 708.

The cloud computing environment 700 may include a resource manager 706. The resource manager 706 may be connected to the resource providers 702 and the computing devices 704 over the computer network 708. In some implementations, the resource manager 706 may facilitate the provision of computing resources by one or more resource providers 702 to one or more computing devices 704. The resource manager 706 may receive a request for a computing resource from a particular computing device 704. The resource manager 706 may identify one or more resource providers 702 capable of providing the computing resource requested by the computing device 704. The resource manager 706 may select a resource provider 702 to provide the computing resource. The resource manager 706 may facilitate a connection between the resource provider 702 and a particular computing device 704. In some implementations, the resource manager 706 may establish a connection between a particular resource provider 702 and a particular computing device 704. In some implementations, the resource manager 706 may redirect a particular computing device 704 to a particular resource provider 702 with the requested computing resource.

Figure 8:
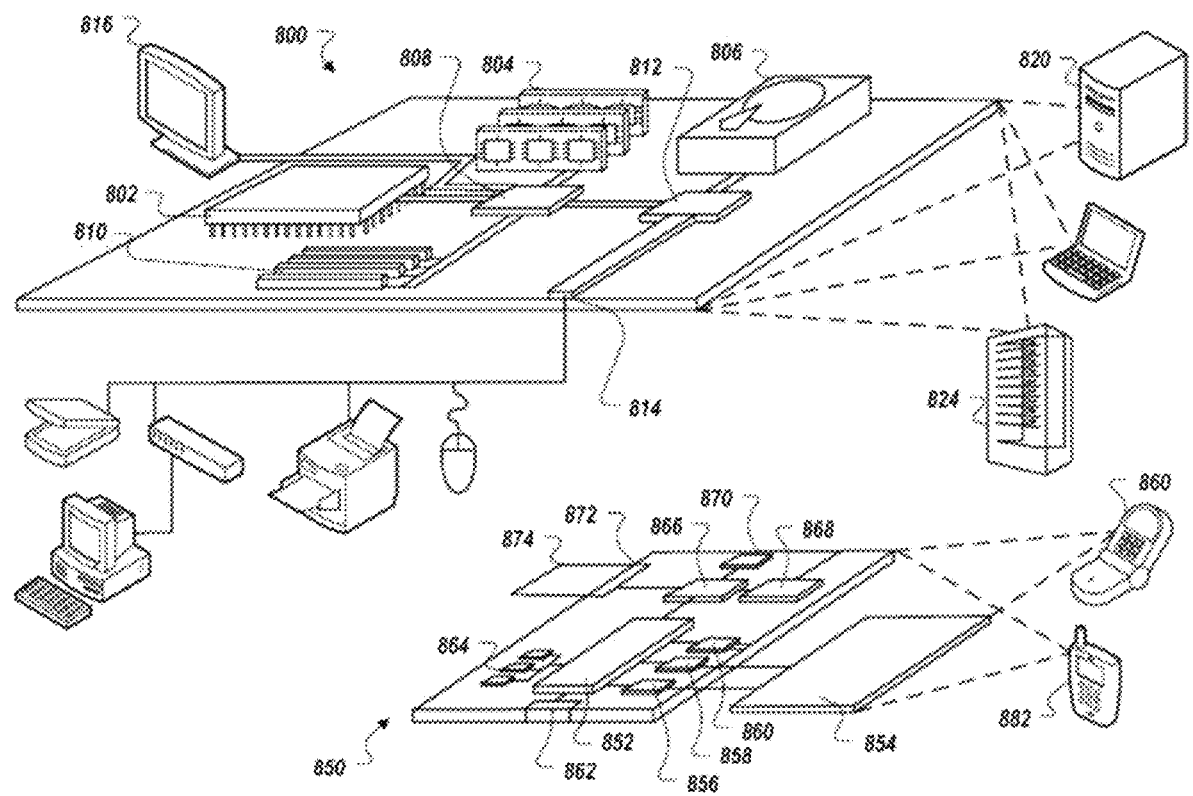
FIG. 8 is a block diagram of an example computing device and an example mobile computing device, for use in illustrative embodiments of the invention.

FIG. 8 shows an example of a computing device 800 and a mobile computing device 850 that can be used in the methods and systems described in this disclosure. The computing device 800 is intended to represent various forms of digital computers, such as laptops, desktops, workstations, personal digital assistants, servers, blade servers, mainframes, and other appropriate computers. The mobile computing device 850 is intended to represent various forms of mobile devices, such as personal digital assistants, cellular telephones, smart-phones, and other similar computing devices. The components shown here, their connections and relationships, and their functions, are meant to be examples only, and are not meant to be limiting.

The computing device 800 includes a processor 802, a memory 804, a storage device 806, a high-speed interface 808 connecting to the memory 804 and multiple high-speed expansion ports 810, and a low-speed interface 812 connecting to a low-speed expansion port 814 and the storage device 806. Each of the processor 802, the memory 804, the storage device 806, the high-speed interface 808, the high-speed expansion ports 810, and the low-speed interface 812, are interconnected using various busses, and may be mounted on a common motherboard or in other manners as appropriate. The processor 802 can process instructions for execution within the computing device 800, including instructions stored in the memory 804 or on the storage device 806 to display graphical information for a GUI on an external input/output device, such as a display 816 coupled to the high-speed interface 808. In other implementations, multiple processors and/or multiple buses may be used, as appropriate, along with multiple memories and types of memory. Also, multiple computing devices may be connected, with each device providing portions of the necessary operations (e.g., as a server bank, a group of blade servers, or a multi-processor system).

The memory 804 stores information within the computing device 800. In some implementations, the memory 804 is a volatile memory unit or units. In some implementations, the memory 804 is a non-volatile memory unit or units. The memory 804 may also be another form of computer-readable medium, such as a magnetic or optical disk.

The storage device 806 is capable of providing mass storage for the computing device 800. In some implementations, the storage device 806 may be or contain a computer-readable medium, such as a floppy disk device, a hard disk device, an optical disk device, or a tape device, a flash memory or other similar solid state memory device, or an array of devices, including devices in a storage area network or other configurations. Instructions can be stored in an information carrier. The instructions, when executed by one or more processing devices (for example, processor 802), perform one or more methods, such as those described above. The instructions can also be stored by one or more storage devices such as computer- or machine-readable mediums (for example, the memory 804, the storage device 806, or memory on the processor 802).

The high-speed interface 808 manages bandwidth-intensive operations for the computing device 800, while the low-speed interface 812 manages lower bandwidth-intensive operations. Such allocation of functions is an example only. In some implementations, the high-speed interface 808 is coupled to the memory 804, the display 816 (e.g., through a graphics processor or accelerator), and to the high-speed expansion ports 810, which may accept various expansion cards (not shown). In the implementation, the low-speed interface 812 is coupled to the storage device 806 and the low-speed expansion port 814. The low-speed expansion port 814, which may include various communication ports (e.g., USB, Bluetooth®, Ethernet, wireless Ethernet) may be coupled to one or more input/output devices, such as a keyboard, a pointing device, a scanner, or a networking device such as a switch or router, e.g., through a network adapter.

The computing device 800 may be implemented in a number of different forms, as shown in the figure. For example, it may be implemented as a standard server 820, or multiple times in a group of such servers. In addition, it may be implemented in a personal computer such as a laptop computer 822. It may also be implemented as part of a rack server system 824. Alternatively, components from the computing device 800 may be combined with other components in a mobile device (not shown), such as a mobile computing device 850. Each of such devices may contain one or more of the computing device 800 and the mobile computing device 850, and an entire system may be made up of multiple computing devices communicating with each other.

The mobile computing device 850 includes a processor 852, a memory 864, an input/output device such as a display 854, a communication interface 866, and a transceiver 868, among other components. The mobile computing device 850 may also be provided with a storage device, such as a micro-drive or other device, to provide additional storage. Each of the processor 852, the memory 864, the display 854, the communication interface 866, and the transceiver 868, are interconnected using various buses, and several of the components may be mounted on a common motherboard or in other manners as appropriate.

The processor 852 can execute instructions within the mobile computing device 850, including instructions stored in the memory 864. The processor 852 may be implemented as a chipset of chips that include separate and multiple analog and digital processors. The processor 852 may provide, for example, for coordination of the other components of the mobile computing device 850, such as control of user interfaces, applications run by the mobile computing device 850, and wireless communication by the mobile computing device 850.

The processor 852 may communicate with a user through a control interface 858 and a display interface 856 coupled to the display 854. The display 854 may be, for example, a TFT (Thin-Film-Transistor Liquid Crystal Display) display or an OLED (Organic Light Emitting Diode) display, or other appropriate display technology. The display interface 856 may comprise appropriate circuitry for driving the display 854 to present graphical and other information to a user. The control interface 858 may receive commands from a user and convert them for submission to the processor 852. In addition, an external interface 862 may provide communication with the processor 852, so as to enable near area communication of the mobile computing device 850 with other devices. The external interface 862 may provide, for example, for wired communication in some implementations, or for wireless communication in other implementations, and multiple interfaces may also be used.

The memory 864 stores information within the mobile computing device 850. The memory 864 can be implemented as one or more of a computer-readable medium or media, a volatile memory unit or units, or a non-volatile memory unit or units. An expansion memory 874 may also be provided and connected to the mobile computing device 850 through an expansion interface 872, which may include, for example, a SIMM (Single In Line Memory Module) card interface. The expansion memory 874 may provide extra storage space for the mobile computing device 850, or may also store applications or other information for the mobile computing device 850. Specifically, the expansion memory 874 may include instructions to carry out or supplement the processes described above, and may include secure information also. Thus, for example, the expansion memory 874 may be provided as a security module for the mobile computing device 850, and may be programmed with instructions that permit secure use of the mobile computing device 850. In addition, secure applications may be provided via the SIMM cards, along with additional information, such as placing identifying information on the SIMM card in a non-hackable manner.

The memory may include, for example, flash memory and/or NVRAM memory (non-volatile random access memory), as discussed below. In some implementations, instructions are stored in an information carrier and, when executed by one or more processing devices (for example, processor 852), perform one or more methods, such as those described above. The instructions can also be stored by one or more storage devices, such as one or more computer- or machine-readable mediums (for example, the memory 864, the expansion memory 874, or memory on the processor 852). In some implementations, the instructions can be received in a propagated signal, for example, over the transceiver 868 or the external interface 862.

The mobile computing device 850 may communicate wirelessly through the communication interface 866, which may include digital signal processing circuitry where necessary. The communication interface 866 may provide for communications under various modes or protocols, such as GSM voice calls (Global System for Mobile communications), SMS (Short Message Service), EMS (Enhanced Messaging Service), or MMS messaging (Multimedia Messaging Service), CDMA (code division multiple access), TDMA (time division multiple access), PDC (Personal Digital Cellular), WCDMA (Wideband Code Division Multiple Access), CDMA2000, or GPRS (General Packet Radio Service), among others. Such communication may occur, for example, through the transceiver 868 using a radio-frequency. In addition, short-range communication may occur, such as using a Bluetooth®, Wi-Fi™, or other such transceiver (not shown). In addition, a GPS (Global Positioning System) receiver module 870 may provide additional navigation- and location-related wireless data to the mobile computing device 850, which may be used as appropriate by applications running on the mobile computing device 850.

The mobile computing device 850 may also communicate audibly using an audio codec 860, which may receive spoken information from a user and convert it to usable digital information. The audio codec 860 may likewise generate audible sound for a user, such as through a speaker, e.g., in a handset of the mobile computing device 850. Such sound may include sound from voice telephone calls, may include recorded sound (e.g., voice messages, music files, etc.) and may also include sound generated by applications operating on the mobile computing device 850.

The mobile computing device 850 may be implemented in a number of different forms, as shown in the figure. For example, it may be implemented as a cellular telephone 880. It may also be implemented as part of a smart-phone 882, personal digital assistant, or other similar mobile device.

Various implementations of the systems and techniques described here can be realized in digital electronic circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications or code) include machine instructions for a programmable processor, and can be implemented in a high-level procedural and/or object-oriented programming language, and/or in assembly/machine language. As used herein, the terms machine-readable medium and computer-readable medium refer to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term machine-readable signal refers to any signal used to provide machine instructions and/or data to a programmable processor.

To provide for interaction with a user, the systems and techniques described here can be implemented on a computer having a display device (e.g., a CRT (cathode ray tube) or LCD (liquid crystal display) monitor) for displaying information to the user and a keyboard and a pointing device (e.g., a mouse or a trackball) by which the user can provide input to the computer. Other kinds of devices can be used to provide for interaction with a user as well; for example, feedback provided to the user can be any form of sensory feedback (e.g., visual feedback, auditory feedback, or tactile feedback); and input from the user can be received in any form, including acoustic, speech, or tactile input.

The systems and techniques described here can be implemented in a computing system that includes a back end component (e.g., as a data server), or that includes a middleware component (e.g., an application server), or that includes a front end component (e.g., a client computer having a graphical user interface or a Web browser through which a user can interact with an implementation of the systems and techniques described here), or any combination of such back end, middleware, or front end components. The components of the system can be interconnected by any form or medium of digital data communication (e.g., a communication network). Examples of communication networks include a local area network (LAN), a wide area network (WAN), and the Internet.

The computing system can include clients and servers. A client and server are generally remote from each other and typically interact through a communication network. The relationship of client and server arises by virtue of computer programs running on the respective computers and having a client-server relationship to each other.

The various described embodiments of the invention may be used in conjunction with one or more other embodiments unless technically incompatible.

The invention claimed is:

1. A patient warming system for stabilizing and/or heating and cooling a patient, comprising:
   a plurality of solid-surface sections arranged for attachment to a surgical table, that form a solid-surface layer, wherein at least one of the plurality of solid-surface sections comprises a power connector for connection to an external power source; and
   a warming pad layer comprising a plurality of warming pads configured for removable connection to the plurality of solid-surface sections, wherein each warming pad of the plurality of warming pads comprises:
   a foam insulation layer;
   a distributed heating element layer having a warming-pad power connection for connection to the power connector;
   an isothermal layer for maintaining uniform temperature across a surface area of the warming pad; and
   a flexible waterproof layer that covers the foam insulation layer, distributed heating element layer, and isothermal layer, wherein power supplied to the warming-pad power connection of the distributed heating element layer of the respective warming pad is used to provide a user-selected uniform temperature over the surface of the flexible waterproof layer in order to prevent hot spots.

2. The patient warming system according to claim 1, comprising:
   a heat sensor embedded in each warming pad of the plurality of warming pads for detecting temperature, wherein the heat sensor is adjacent to the isothermal layer;
   a heat sensor data connector connected to the heat sensor, wherein the heat sensor data connector is located on a side of the one of the plurality of warming pads; and
   a data connector in the solid-surface layer for connection to the heat sensor data connector for obtaining temperature data about the isothermal layer for use in adjusting the temperature of the respective warming pad.

3. The patient warming system according to claim 1, wherein each warming pad of the plurality of warming pads comprises a cooling layer comprising an arrangement of cooling liquid conduit.

4. The patient warming system according to claim 1, comprising:
   one or more sensors for attaching to the patient's skin in order to monitor the patient's skin temperature for a reduced likelihood of the patient developing skin burns.

5. A patient warming pad for stabilizing and/or heating and cooling a patient, the patient warming pad comprising:
   a foam insulation layer for contacting a surgical table;
   a heating element layer coupled to the foam insulation layer, the heating element layer comprising a heater power connector;
   an isothermal layer for maintaining uniform temperature across its surface area, wherein the isothermal layer is configured to be positioned between the heating element layer and the patient when the patient is laying on the patient warming pad; and
   a flexible waterproof cover layer coupled to the isothermal layer.

6. The patient warming pad according to claim 5, comprising an electronic insulation layer located at a location of at least one of above and below the isothermal layer.

7. The patient warming pad according to claim 5, comprising a disposable cover configured to fit around the patient warming pad.

8. The patient warming pad according to claim 5, comprising a cooling layer comprising an arrangement of cooling liquid conduit.

* * * * *